United States Patent
Frank et al.

(10) Patent No.: US 7,977,360 B2
(45) Date of Patent: *Jul. 12, 2011

(54) BENZO[D]ISOXAZOL-3-YL-AMINE COMPOUNDS AND THEIR USE AS VANILLOID RECEPTOR LIGANDS

(75) Inventors: Robert Frank, Aachen (DE); Beatrix Merla, Aachen (DE); Melanie Reich, Aachen (DE); Ruth Jostock, Stolberg (DE)

(73) Assignee: Gruenenthal GmbH, Aachen (DE)

( * ) Notice: Subject to any disclaimer, the term of this patent is extended or adjusted under 35 U.S.C. 154(b) by 64 days.

This patent is subject to a terminal disclaimer.

(21) Appl. No.: 11/914,636

(22) PCT Filed: May 18, 2006

(86) PCT No.: PCT/EP2006/004698
§ 371 (c)(1),
(2), (4) Date: Aug. 8, 2008

(87) PCT Pub. No.: WO2006/122799
PCT Pub. Date: Nov. 23, 2006

(65) Prior Publication Data
US 2009/0042945 A1    Feb. 12, 2009

(30) Foreign Application Priority Data

May 18, 2005  (DE) .......................... 10 2005 023 589
Aug. 16, 2005  (DE) .......................... 10 2005 038 947

(51) Int. Cl.
*A61K 31/423*  (2006.01)
*A61K 31/443*  (2006.01)
*A61K 31/4439* (2006.01)
*C07D 401/04*  (2006.01)
*C07D 413/04*  (2006.01)

(52) U.S. Cl. ............... 514/338; 514/379; 546/272.1; 548/241

(58) Field of Classification Search ................. None
See application file for complete search history.

(56) References Cited

U.S. PATENT DOCUMENTS

| | | | | |
|---|---|---|---|---|
| 2003/0176454 A1 * | 9/2003 | Yamada et al. | ................ | 514/284 |
| 2007/0185324 A1 * | 8/2007 | De Morin et al. | ................ | 544/60 |

FOREIGN PATENT DOCUMENTS

| | | |
|---|---|---|
| WO | WO 00/27199 A1 | 5/2000 |
| WO | WO 00/27627 A1 | 5/2000 |
| WO | WO 01/05784 A1 | 1/2001 |
| WO | WO 01/87845 A2 | 11/2001 |
| WO | WO 0187845 A2 * | 11/2001 |
| WO | WO 2004/002477 A1 | 1/2004 |
| WO | WO 2004/010995 A1 | 2/2004 |
| WO | WO 2004/113304 A1 | 12/2004 |
| WO | WO 2005/016915 A1 | 2/2005 |

OTHER PUBLICATIONS

Byrn et al. Solid-State Chemistry of Drugs, 2d, Chapter 11 Hydrates and Solvates, 233-247 (1999).*
Morissette et al. Adv. Drug Delivery Rev. 2004, 56, 275-300 (2004).*
Rouhi, Chem. & Eng. News, Feb. 24, 2003, 81(8), 32-35 (2003).*
U.S. Appl. No. 11/941,331, filed Nov. 2007, Merla et al.*
Form PCT/IPEA/416 and Form PCT/IPEA/409 with amended claims with English translation of relevant portion (Eighty-four (84) Pages).
International Search Report dated Aug. 16, 2006 with English translation of relevant portion (Twelve (12) Pages).
German Search Report dated Mar. 9, 2006 with English translation (Nine (9) Pages).
Form PCT/IB/338 and Form PCT/IPEA/409 (Five (5) Pages), (Apr. 2, 2008).

* cited by examiner

*Primary Examiner* — Yong Chu
*Assistant Examiner* — Michael Barker
(74) *Attorney, Agent, or Firm* — Crowell & Moring LLP

(57) ABSTRACT

The present invention relates to substituted benzo[d]isoxazol-3-yl-amine compounds, methods for their production, medicaments containing these compounds and the use of these compounds to produce medicaments.

18 Claims, No Drawings

BENZO[D]ISOXAZOL-3-YL-AMINE COMPOUNDS AND THEIR USE AS VANILLOID RECEPTOR LIGANDS

The present invention relates to substituted benzo[d]isoxazol-3-yl-amine compounds, methods for their production, medicaments containing these compounds and the use of these compounds for producing medicaments.

The treatment of pain, in particular neuropathic pain, is very important in medicine. There is worldwide demand for effective pain therapies. The urgent need for action for patient-focused and target-oriented treatment of chronic and non-chronic states of pain, whereby this is to be understood as the successful and satisfactory treatment of pain for the patient, is also documented in the large number of scientific studies which have appeared recently in the field of applied analgesia and fundamental research on nociception.

The vanilloid receptor of subtype 1 (VR1/TRPV1), which is often referred to as a capsaicin receptor, is a suitable starting point for treating pain; in particular pain selected from the group comprising acute pain, chronic pain, neuropathic pain and visceral pain, particularly preferably neurophatic pain. This receptor is stimulated, among other things, by vanilloids such as, for example, capsaicin, heat and protons and plays a central role in the generation of pain. It is also important for a number of further physiological and pathophysiological processes such as, for example, migraines; depression; neurodegenerative diseases; cognitive diseases; states of anxiety; epilepsy; coughs; diarrhoea; pruritus; disorders of the cardiovascular system; eating disorders; medication dependency; medication abuse and particularly urinary incontinence.

One object of the present invention therefore lay in providing new compounds which are particularly suitable as pharmacological agents in medicaments, preferably in medicaments for treating disorders or illnesses which are at least partially mediated by vanilloid receptors 1 (VR1/TRPV1 receptors).

It has now been surprisingly found that substituted benzo[d]isoxazol-3-yl-amine compounds of formula I indicated below are suitable for treating pain and also have an excellent affinity to the vanilloid receptor of subtype 1 (VR1/TRPV1 receptor) and are therefore suitable particularly for the prophylaxis and/or treatment of disorders or illnesses which are at least partially mediated by vanilloid receptors 1 (VR1/TRPV1).

One subject matter of the present invention is therefore substituted benzo[d]isoxazol-3-yl-amine compounds of the general formula I,

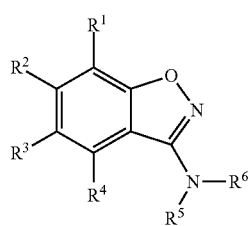

I wherein
$R^1$, $R^2$, $R^3$ and $R^4$, independently of one another, respectively stand for
H; F, Cl, Br, I; —CN; —NC; —NO$_2$; —SF$_5$; —NR$^7$R$^8$; —OR$^9$; —SR$^{10}$; —C(=O)OR$^{11}$; —C(=O)NR$^{12}$R$^{13}$; —S(=O)$_2$R$^{14}$; —C(=O)R$^{15}$; —NR$^{16}$—S(=O)$_2$R$^{17}$;

for a linear or branched, saturated or unsaturated, unsubstituted or at least monosubstituted aliphatic residue;
for a saturated or unsaturated, unsubstituted or at least monosubstituted cycloaliphatic residue which possibly has at least one heteroatom as a ring member, condenses with a monocyclic or polycyclic ring system and/or can be bonded via a linear or branched alkylene, alkenylene or alkinylene group;
or for an unsubstituted or at least monosubstituted aryl or heteroaryl residue which condenses with a monocyclic or polycyclic ring system and/or can be bonded via a linear or branched alkylene, alkenylene or alkinylene group,
wherein at least one of residues $R^1$, $R^2$, $R^3$ and $R^4$ stands for an unsubstituted or at least monosubstituted aryl or heteroaryl residue;

$R^5$ and $R^6$, independently of one another, respectively stand for
H; —C(=O)R$^{18}$; —C(=O)NR$^{19}$R$^{20}$; —C(=S)NR$^{21}$R$^{22}$; —S(=O)$_2$R$^{23}$;
for a linear or branched, saturated or unsaturated, unsubstituted or at least monosubstituted aliphatic residue;
for a saturated or unsaturated, unsubstituted or at least monosubstituted cycloaliphatic residue which possibly has at least one heteroatom as a ring member, condenses with a monocyclic or polycyclic ring system and/or can be bonded via a linear or branched alkylene group;
or for an unsubstituted or at least monosubstituted aryl or heteroaryl residue which condenses with a monocyclic or polycyclic ring system and/or can be bonded via a linear or branched alkylene group, or $R^5$ and $R^6$ together with the nitrogen atom which connects them form as a ring member a saturated or unsaturated, unsubstituted or at least monosubstituted heterocycloaliphatic residue which possibly has at least one further heteroatom as a ring member, $R^7$ and $R^8$, independently of one another, respectively stand for
H, —C(=O)R$^{15}$ or for a linear or branched, saturated or unsaturated, unsubstituted or at least monosubstituted aliphatic residue, or
$R^7$ and $R^8$ together with the nitrogen atom which connects them form as a ring member a saturated or unsaturated, unsubstituted or at least monosubstituted heterocycloaliphatic residue which possibly has at least one further heteroatom as a ring member, $R^9$, $R^{10}$, $R^{11}$ and $R^{16}$, independently of one another, respectively stand for
H;
for a linear or branched, saturated or unsaturated, unsubstituted or at least monosubstituted aliphatic residue;
for a saturated or unsaturated, unsubstituted or at least monosubstituted cycloaliphatic residue which possibly has at least one heteroatom as a ring member, condenses with a monocyclic or polycyclic ring system and/or can be bonded via a linear or branched alkylene group;
or for an unsubstituted or at least monosubstituted aryl or heteroaryl residue which condenses with a monocyclic or polycyclic ring system and/or can be bonded via a linear or branched alkylene group;

$R^{12}$ and $R^{13}$, independently of one another, respectively stand for
H or for a linear or branched, saturated or unsaturated, unsubstituted or at least monosubstituted aliphatic residue, or $R^{12}$ and $R^{13}$ together with the nitrogen atom which connects them form as a ring member a saturated or unsaturated, unsubstituted or at least monosubstituted heterocyloaliphatic residue which possibly has at least one further heteroatom as a ring member, $R^{14}$ and $R^{23}$, independently of one another, respectively stand for
—$NR^7R^8$;
for a linear or branched, saturated or unsaturated, unsubstituted or at least monosubstituted aliphatic residue,
for a saturated or unsaturated, unsubstituted or at least monosubstituted cycloaliphatic residue which possibly has at least one heteroatom as a ring member, condenses with a monocyclic or polycyclic ring system and/or can be bonded via a linear or branched alkylene group,
or for an unsubstituted or at least monosubstituted aryl or heteroaryl residue which condenses with a monocyclic or polycyclic ring system and/or can be bonded via a linear or branched alkylene group, $R^{15}$, $R^{17}$ and $R^{18}$, independently of one another, respectively stand
for a linear or branched, saturated or unsaturated, unsubstituted or at least monosubstituted aliphatic residue,
for a saturated or unsaturated, unsubstituted or at least monosubstituted cycloaliphatic residue which possibly has at least one heteroatom as a ring member, condenses with a monocyclic or polycyclic ring system and/or can be bonded via a linear or branched alkylene group,
or for an unsubstituted or at least monosubstituted aryl or heteroaryl residue which condenses with a monocyclic or polycyclic ring system and/or can be bonded via a linear or branched alkylene group, $R^{19}$ and $R^{20}$, independently of one another, respectively stand for
H or for a linear or branched, saturated or unsaturated, unsubstituted or at least monosubstituted aliphatic residue, or $R^{19}$ and $R^{20}$ together with the nitrogen atom which connects them form as a ring member a saturated or unsaturated, unsubstituted or at least monosubstituted heterocyloaliphatic residue which possibly has at least one further heteroatom as a ring member, $R^{21}$ and $R^{22}$, independently of one another, respectively stand for
H or for a linear or branched, saturated or unsaturated, unsubstituted or at least monosubstituted aliphatic residue, or $R^{21}$ and $R^{22}$ together with the nitrogen atom which connects them form as a ring member a saturated or unsaturated, unsubstituted or at least monosubstituted heterocyloaliphatic residue which possibly has at least one further heteroatom as a ring member, respectively, where applicable, in the form of one of its pure stereoisomers, in particular enantiomers or diastereomers, their racemates or in the form of a mixture of stereoisomers, in particular enantiomers and/or diastereomers, in any desired mixture ratio, or respectively in the form of corresponding salts, or respectively in the form of corresponding solvates.

$R^5$ and $R^6$ preferably do not stand simultaneously for a residue selected from the group comprising linear or branched, saturated or unsaturated, unsubstituted or at least monosubstituted aliphatic residue and hydrogen.

Cycloaliphatic residues are preferably substituted in the position of substituents $R^5$ and $R^6$ with substituents independently of one another selected from the group comprising oxo (=O), thioxo (=S), F, Cl, Br, I, —CN, —$CF_3$, —$SF_5$, —OH, —O—$C_{1-5}$-alkyl, —$NO_2$, —O—$CF_3$, —S—$CF_3$, —SH, —S—$C_{1-5}$-alkyl, —$C_{1-5}$-alkyl, —C(=O)—OH, —C(=O)—O—$C_{1-5}$-alkyl, —NH—$C_{1-5}$-alkyl, —N($C_{1-5}$-alkyl)$_2$, —O-phenyl, —O-benzyl, phenyl and benzyl, whereby the cyclic part of residues —O-phenyl, —O-benzyl, phenyl and benzyl can be respectively substituted with substituents independently of one another selected from the group comprising F, Cl, Br, —OH, —$CF_3$, —$SF_5$, —CN, —$NO_2$, —$C_{1-5}$-alkyl, —O—$C_{1-5}$-alkyl, —O—$CF_3$, —S—$CF_3$, phenyl and —O-benzyl.

Aryl and heteroaryl residues are preferably substituted in the position of substituents $R^5$ and $R^6$ respectively with substituents independently of one another selected from the group comprising F, Cl, Br, I, —CN, —$CF_3$, —$SF_5$, —OH, —O—$C_{1-5}$-alkyl, —$NO_2$, —O—$CF_3$, —S—$CF_3$, —SH, —S—$C_{1-5}$-alkyl, —$C_{1-5}$-alkyl, —C(=O)—OH, —C(=O)—O—$C_{1-5}$-alkyl, —NH—$C_{1-5}$-alkyl, —N($C_{1-5}$-alkyl)$_2$, —NH—C(=O)—O—$C_{1-5}$-alkyl, —C(=O)—H, —C(=O)—$C_{1-5}$-alkyl, —C(=O)—$NH_2$, —C(=O)NH—$C_{1-5}$-alkyl, —C(=O)—N($C_{1-5}$-alkyl)$_2$, —S(=O)$_2NH_2$; —S(=O)$_2$N(H)($C_{1-5}$-alkyl); —S(=O)$_2$N($C_{1-5}$-alkyl)($C_{1-5}$-alkyl); —S(=O)$_2$-Phenyl; —S(=O)$_2$—$C_{1-5}$-alkyl; —$CH_2$—NH-cyclopropyl; —$CH_2$—N($C_{1-5}$-alkyl)-cyclopropyl; —C(=O)—N(cyclopropyl)-$C_{1-5}$-alkyl, —N (cyclopropyl)-S(=O)$_2$—$C_{1-5}$-alkyl, —$CH_2$—NH—S(=O)$_2$—$C_{1-5}$-alkyl, —$CH_2$—N (cyclopropyl)-S(=O)$_2$—$C_{1-5}$-alkyl, —$CH_2$—N(cyclopropyl)-C(=O)—$C_{1-5}$-alkyl, —$CH_2$—N (cyclopropyl)-C(=O)-phenyl, —O-phenyl, —O-benzyl, phenyl, benzyl, thiophenyl (thienyl) and furanyl, whereby the cyclic part of residues —$CH_2$—N(cyclopropyl)-C(=O)-phenyl, —O-phenyl, —O-benzyl, phenyl, —S(=O)$_2$-phenyl and benzyl can be substituted with substituents independently of one another selected from the group comprising F, Cl, Br, —OH, —$CF_3$, —$SF_5$, —CN, —$NO_2$, —$C_{1-5}$-alkyl, —O—$C_{1-5}$-alkyl, —O—$CF_3$, —S—$CF_3$, phenyl and —O-benzyl.

Aryl and heteroaryl residues are preferably substituted in the position of substituents $R^1$, $R^2$, $R^3$ and $R^4$ with substituents independently of one another selected from the group comprising F, Cl, Br, I, —CN, —$CF_3$, —$SF_5$, —OH, —O—$C_{1-5}$-alkyl, —$NH_2$, —$NO_2$, —O—$CF_3$, —S—$CF_3$, —SH, —S—$C_{1-5}$-alkyl, —$C_{1-5}$-alkyl, —C(=O)—OH, —C(=O)—O—$C_{1-5}$-alkyl, —NH—($C_{1-5}$-alkyl), —N($C_{1-5}$-alkyl)($C_{1-5}$-alkyl), —NH—C(=O)—O—($C_{1-5}$-alkyl), —C(=O)—NH—$CH_3$, —C(=O)—NH—$C_2H_5$, —C(=O)—H, —C(=O)—($C_{1-5}$-alkyl), —C(=O)—N($C_{1-5}$-alkyl)($C_{1-5}$-alkyl), —S(=O)$_2NH_2$; —S(=O)$_2$N(H)($C_{1-5}$-alkyl); —S(=O)$_2$N($C_{1-5}$-alkyl)($C_{1-15}$-alkyl); —S(=O)$_2$-phenyl; —S(=O)$_2$—$C_{1-5}$-alkyl; —C(=O)—N (cyclopropyl)-$C_{1-5}$-alkyl, —N(cyclopropyl)-S(=O)$_2$—$C_{1-5}$-alkyl, —$CH_2$—NH—S(=O)$_2$—$C_{1-5}$-alkyl, —$CH_2$—N(cyclopropyl)-S(=O)$_2$—$C_{1-5}$-alkyl, —$CH_2$—N(cyclopropyl)-C(=O)—$C_{1-5}$-alkyl, —$CH_2$—N(cyclopropyl)-C(=O)-phenyl, —O-phenyl, —O-benzyl, phenyl, benzyl, thiophenyl (thienyl), furanyl and pyridinyl, whereby the cyclic part of residues —$CH_2$—N(cyclopropyl)-C(=O)-phenyl, —O-phenyl, —O-benzyl, phenyl, —S(=O)$_2$-phenyl, benzyl, thiophenyl (thienyl), furanyl and pyridinyl can be respectively substituted with substituents independently of one another selected from the group comprising F, Cl, Br, —OH, —$CF_3$, —$SF_5$, —CN, —$NO_2$, —$C_{1-5}$-alkyl, —O—$C_{1-5}$-alkyl, —O—$CF_3$, —S—$CF_3$, phenyl and —O-benzyl.

The above-mentioned (hetero)cycloaliphatic residues can preferably, where applicable, be substituted respectively with 1, 2, 3, 4 or 5 substituents independently of one another selected from the group comprising oxo (=O), thioxo (=S), F, Cl, Br, I, —CN, —$CF_3$, —$SF_5$, —OH, —O—$C_{1-5}$-alkyl, —NH$_2$, —NO$_2$, —O—CF$_3$, —S—CF$_3$, —SH, —S—C$_{1-5}$-alkyl, —C$_{1-5}$-alkyl, —C(=O)—OH, —C(=O)—O—C$_{1-5}$-alkyl, —NH—C$_{1-5}$-alkyl, —N(C$_{1-5}$-alkyl)$_2$, —O-phenyl, —O-benzyl, phenyl and benzyl, whereby the cyclic part of residues —O-phenyl, —O-benzyl, phenyl and benzyl can be respectively substituted with 1, 2, 3, 4 or 5 substituents independently of one another selected from the group comprising F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl. Insofar as a cycloaliphatic residue has one or more, for example, 1, 2, 3, 4 or 5 heteroatoms as ring members, these can be preferably independently of one another selected from the group comprising oxygen, nitrogen and sulphur.

For example, cyclopropyl, cyclobutyl, cyclopentyl, cyclohexyl, cycloheptyl, cyclooctyl, cyclopentenyl, cyclohexenyl, cycloheptenyl, imidazolidinyl, tetrahydrofuranyl, tetrahydrothiophenyl, pyrrolidinyl, piperidinyl, morpholinyl, piperazinyl, thiomorpholinyl, tetrahydropyranyl, azepanyl, diazepanyl and dithiolanyl are cited as (hetero)cycloaliphatic residues.

Within the meaning of the present invention, a monocyclic or polycyclic ring system is taken to mean monocyclic or polycyclic hydrocarbon residues which can be saturated or unsaturated and, where applicable, have 1, 2, 3, 4 or 5 heteroatom(s) as (a) ring member(s) which independently of one another are selected from the group comprising oxygen, nitrogen and sulphur.

Such a mono- or polycyclic ring system can, for example, be condensed (annelated) with an aryl residue or a heteroaryl residue.

Insofar as a polycyclic ring system such as, for example, a bicyclic ring system is present, the various rings, respectively independently of one another, can have a different degree of saturation, i.e. be saturated or unsaturated. A polycyclic ring system is preferably a bicyclic ring system.

(1,3)-benzodioxolyl and (1,4)-benzodioxanyl are cited as examples of aryl residues which are condensed with a monocyclic or polycyclic ring system.

The rings of the above-mentioned monocyclic or polycyclic ring systems preferably respectively have 5, 6 or 7 members and can respectively have, where applicable, 1, 2, 3, 4 or 5 heteroatom(s) as (a) ring member(s) which are independently of one another selected from the group comprising oxygen, nitrogen and sulphur.

Moreover, the rings of the above-mentioned monocyclic or polycyclic ring systems can preferably be substituted, where applicable, respectively with 1, 2, 3, 4 or 5 substituents independently of one another selected from the group comprising oxo (=O), thioxo (=S), F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$-alkyl, —C(=O)—OH, —C(=O)—O—C$_{1-5}$-alkyl, —NH—C$_{1-5}$-alkyl, —N(C$_{1-5}$-alkyl)$_2$, —O-phenyl, —O-benzyl, phenyl and benzyl, whereby the cyclic part of residues —O-phenyl, —O-benzyl, phenyl and benzyl can respectively be substituted with 1, 2, 3, 4 or 5 substituents independently of one another selected from the group comprising F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl.

Unless indicated otherwise, the above-mentioned aryl or heteroaryl residues can also preferably be substituted, where applicable, respectively with 1, 2, 3, 4 or 5 substituents independently of one another selected from the group comprising F, Cl, Br, I, —CN, —CF$_3$, —SF$_5$, —OH, —O—C$_{1-5}$-alkyl, —NH$_2$, —NO$_2$, —O—CF$_3$, —S—CF$_3$, —SH, —S—C$_{1-5}$-alkyl, —C$_{1-5}$-alkyl, —C(=O)—OH, —C(=O)—O—C$_{1-5}$-alkyl, —NH—C$_{1-5}$-alkyl, —N(C$_{1-5}$-alkyl)$_2$, —NH—C(=O)—O—C$_{1-5}$-alkyl, —C(=O)—H, —C(=O)—C$_{1-5}$-alkyl, —C(=O)—NH$_2$, —C(=O)NH—C$_{1-5}$-alkyl, —C(=O)—N(C$_{1-5}$-alkyl)$_2$, —S(=O)$_2$NH$_2$; —S(=O)$_2$N(H)(C$_{1-5}$-alkyl); —S(=O)$_2$N(C$_{1-5}$-alkyl)(C$_{1-5}$-alkyl); —S(=O)$_2$-phenyl; —S(=O)$_2$—C$_{1-5}$-alkyl; —CH$_2$—NH-cyclopropyl; —CH$_2$—N(C$_{1-5}$-alkyl)-cyclopropyl; —C(=O)—N(cyclopropyl)-C$_{1-5}$-alkyl, —N(cyclopropyl)-S(=O)$_2$—C$_{1-5}$-alkyl, —CH$_2$—NH—S(=O)$_2$—C$_{1-5}$-alkyl, —CH$_2$—N(cyclopropyl)-S(=O)$_2$—C$_{1-5}$-alkyl, —CH$_2$—N(cyclopropyl)-C(=O)—C$_{1-5}$-alkyl, —CH$_2$—N(cyclopropyl)-C(=O)-phenyl, —O-phenyl, —O-benzyl, phenyl, benzyl, thiophenyl (thienyl), furanyl and pyridinyl, whereby the cyclic part of residues —CH$_2$—N(cyclopropyl)-C(=O)-phenyl, —O-phenyl, —O-benzyl, phenyl, —S(=O)$_2$-phenyl and benzyl can respectively be substituted with 1, 2, 3, 4 or 5 substituents independently of one another selected from the group comprising F, Cl, Br, —OH, —CF$_3$, —SF$_5$, —CN, —NO$_2$, —C$_{1-5}$-alkyl, —O—C$_{1-5}$-alkyl, —O—CF$_3$, —S—CF$_3$, phenyl and —O-benzyl.

The above-mentioned heteroaryl residues also preferably respectively have 1, 2, 3, 4 or 5 heteroatom(s) independently of one another selected from the group comprising oxygen, nitrogen and sulphur as (a) ring member(s).

Phenyl and naphthyl (including 1-naphthyl and 2-naphthyl) are, for example, cited as aryl residues.

Thiophenyl, furanyl, pyrrolyl, pyrazolyl, pyrazinyl, pyranyl, triazolyl, pyridinyl, imidazolyl, indolyl, isoindolyl, benzo[b]furanyl, benzo[b]thiophenyl, thiazolyl, oxazolyl, isoxazolyl, pyridazinyl, pyrazinyl, pyrimidinyl, indazolyl, chinoxalinyl, chinolinyl and isochinolinyl are, for example, cited as heteroaryl residues.

The above-mentioned aliphatic residues, i.e. the alkyl, alkenyl and alkinyl residues, can preferably have 1-10 or 2-10 carbon atoms in the alkyl part and preferably be substituted with, where applicable, 1, 2, 3, 4, 5, 6, 7, 8 or 9 substituents independently of one another selected from the group comprising F, Cl, Br, I, —CN, —NO$_2$, —OH, —NH$_2$, —SH, —O(C$_{1-5}$-alkyl), —S(C$_{1-5}$-alkyl), —NH(C$_{1-5}$-alkyl), —N(C$_{1-5}$-alkyl)(C$_{1-5}$-alkyl), —OCF$_3$ and —SCF$_3$. Alkenyl residues have at least one, preferably 1, 2, 3 or 4 C=C double bonds and alkinyl residues at least one, preferably 1, 2, 3 or 4 C—C triple bonds.

Alkyl residues are preferably selected from the group comprising methyl, ethyl, n-propyl, isopropyl, n-butyl, sec-butyl, isobutyl, tert-butyl, n-pentyl, sec-pentyl, neopentyl and n-hexyl which can be substituted, where applicable, with 1, 2, 3, 4, 5, 6, 7, 8 or 9 substituents independently of one another selected from the group comprising F, Cl, Br, I, —CN, —NO$_2$, —OH, —NH$_2$, —SH, —OCH$_3$, —O—C$_2$H$_5$, —SCH$_3$, —S—C$_2$H$_5$, —OCF$_3$, —SCF$_3$, —NH—CH$_3$, —N(CH$_3$)$_2$, —N(C$_2$H$_5$)$_2$ and —N(CH$_3$)(C$_2$H$_5$).

Alkenyl residues are furthermore preferably selected from the group comprising vinyl, 1-propenyl, 2-propenyl, 1-butenyl, 2-butenyl, 3-butenyl, 2-methyl-butene-2-yl, 1-pentenyl, 2-pentenyl, 3-pentenyl and 4-pentenyl which can be substituted, where applicable, with 1, 2 or 3 substituents independently of one another selected from the group comprising F, Cl, Br, I, —CN, —NO$_2$, —OH, —NH$_2$, —SH, —OCH$_3$, —O—C$_2$H$_5$, —SCH$_3$, —S—C$_2$H$_5$, —OCF$_3$, —SCF$_3$, —NH—CH$_3$, —N(CH$_3$)$_2$, —N(C$_2$H$_5$)$_2$ and —N(CH$_3$)(C$_2$H$_5$).

Alkinyl residues are furthermore preferably selected from the group comprising ethinyl, 1-propinyl, 2-propinyl, 1-butinyl, 2-butinyl and 3-butinyl which can be substituted, where applicable, with 1, 2 or 3 substituents independently of one another selected from the group comprising F, Cl, Br, I, —CN, —NO$_2$, —OH, —NH$_2$, —SH, —OCH$_3$, —O—C$_2$H$_5$, —SCH₃, —S—C₂H₅, —OCF₃, —SCF₃, —NH—CH₃, —N(CH₃)₂, —N(C₂H₅)₂ and —N(CH₃)(C₂H₅).

Substituted benzo[d]isoxazol-3-yl-amine compounds of the general formula I are preferred, wherein $R^1$, $R^2$, $R^3$ and $R^4$, independently of one another, respectively stand for H; F; Cl; Br; I; —CN; —NC; —NO₂; —SF₅; —NR⁷R⁸; —OR⁹; —SR¹⁰; —C(=O)OR¹¹; —C(=O)NR¹²R¹³; —S(=O)₂R¹⁴; —C(=O)R¹⁵; —NR¹⁶—S(=O)₂R¹⁷; $C_{1-10}$-alkyl, $C_{2-10}$-alkenyl, $C_{2-10}$-alkinyl; $C_{3-8}$-cycloalkyl; —($C_{1-5}$-alkylene)-$C_{3-8}$-cycloalkyl; heterocycloalkyl; —($C_{1-5}$-alkylene)-heterocycloalkyl; aryl; heteroaryl; —($C_{1-5}$-alkylene)-aryl or —($C_{1-5}$-alkylene)-heteroaryl;

whereby at least one of residues $R^1$, $R^2$, $R^3$ and $R^4$ stands for an aryl or heteroaryl residue;

$R^5$ and $R^6$, independently of one another, respectively stand for

H; —C(=O)R¹⁸; —C(=O)NR¹⁹R²⁰; —C(=S)NR²¹R²²; —S(=O)₂R²³; $C_{1-10}$-alkyl, $C_{2-10}$-alkenyl, $C_{2-10}$-alkinyl; $C_{3-8}$-cycloalkyl; —($C_{1-5}$-alkylene)-$C_{3-8}$-cycloalkyl; heterocycloalkyl; —($C_{1-5}$-alkylene)-heterocycloalkyl; aryl; heteroaryl; —($C_{1-5}$-alkylene)-aryl or —($C_{1-5}$-alkylene)-heteroaryl;

with the proviso that $R^5$ and $R^6$ do not simultaneously stand for a residue selected from the group comprising $C_{1-10}$-alkyl and hydrogen;

or $R^5$ and $R^6$ together with the nitrogen atom which connects them form as a ring member a residue which is selected from group H comprising

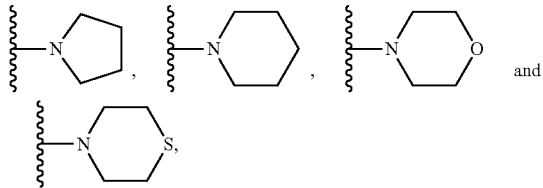

$R^7$ and $R^8$, independently of one another, respectively stand for

H, —C(=O)R¹⁵ or $C_{1-10}$-alkyl, or $R^7$ and $R^8$ together with the nitrogen atom which connects them form as a ring member a residue which is selected from group H indicated above;

$R^9$, $R^{10}$, $R^{11}$ and $R^{16}$, independently of one another, respectively stand for H; $C_{1-10}$-alkyl, $C_{2-10}$-alkenyl, $C_{2-10}$-alkinyl; $C_{3-8}$-cycloalkyl; —($C_{1-5}$-alkylene)-$C_{3-8}$-cycloalkyl; heterocycloalkyl; —($C_{1-5}$-alkylene)-heterocycloalkyl; aryl; heteroaryl; —($C_{1-5}$-alkylene)-aryl or —($C_{1-5}$-alkylene)-heteroaryl;

$R^{12}$ and $R^{13}$, independently of one another, respectively stand for

H or for a $C_{1-10}$-alkyl residue; or $R^{12}$ and $R^{13}$ together with the nitrogen atom which connects them form as a ring member a residue which is selected from group H indicated above;

$R^{14}$ and $R^{23}$, independently of one another, respectively stand for

—NR⁷R⁸; $C_{1-10}$-alkyl, $C_{2-10}$-alkenyl, $C_{2-10}$-alkinyl; $C_{3-8}$-cycloalkyl; —($C_{1-5}$-alkylene)-$C_{3-8}$-cycloalkyl; heterocycloalkyl; —($C_{1-5}$-alkylene)-heterocycloalkyl; aryl; heteroaryl; —($C_{1-15}$-alkylene)-aryl or —($C_{1-5}$-alkylene)-heteroaryl;

$R^{15}$, $R^{17}$ and $R^{18}$, independently of one another, respectively stand for $C_{1-10}$-alkyl, $C_{2-10}$-alkenyl, $C_{2-10}$-alkinyl; $C_{3-8}$-cycloalkyl; —($C_{1-5}$-alkylene)-$C_{3-8}$-cycloalkyl; heterocycloalkyl; —($C_{1-5}$-alkylene)-heterocycloalkyl; aryl; heteroaryl; —($C_{1-5}$-alkylene)-aryl or —($C_{1-5}$-alkylene)-heteroaryl;

$R^{19}$ and $R^{20}$, independently of one another, respectively stand for

H or for $C_{1-10}$-alkyl, or $R^{19}$ and $R^{20}$ together with the nitrogen atom which connects them form as a ring member a residue which is selected from group H indicated above;

$R^{21}$ and $R^{22}$, independently of one another, respectively stand for

H or for $C_{1-10}$-alkyl, or $R^{21}$ and $R^{22}$ together with the nitrogen atom which connects them form as a ring member a residue which is selected from group H indicated above;

whereby the above-mentioned $C_{1-10}$-alkyl-, $C_{2-10}$-alkenyl- and $C_{2-10}$-alkinyl residues are respectively linear or branched and, where applicable, can be substituted with 1, 2, 3, 4 or 5 substituents independently of one another selected from the group comprising F; Cl; Br; —CN; —OH; —SH; —O—$C_{1-2}$-alkyl; —S—$C_{1-2}$-alkyl and —NH₂, the above-mentioned $C_{3-8}$-cycloalkyl residues can be respectively substituted, where applicable, with 1, 2, 3, 4 or 5 substituents independently of one another selected from the group comprising F; Cl; Br; —CN; —OH; —SH; —$C_{1-5}$-alkyl; —O—$C_{1-2}$-alkyl; —S—$C_{1-2}$-alkyl and —NH₂, the above-mentioned heterocycloalkyl residues respectively have 4, 5, 6 or 7 members, have 1 or 2 heteroatoms independently of one another selected from the group comprising oxygen, sulphur and nitrogen as (a) ring member(s) and can be substituted, where applicable, with 1, 2, 3, 4 or 5 substituents independently of one another selected from the group comprising F; Cl; Br; —CN; —OH; —SH; —$C_{1-5}$-alkyl; —O—$C_{1-2}$-alkyl; —S—$C_{1-2}$-alkyl and —NH₂, the above-mentioned aryl residues respectively stand for a phenyl or naphthyl residue which can be substituted with 1, 2, 3, 4 or 5 substituents independently of one another selected from the group comprising F; Cl; Br; I; —CF₃; —OCF₃; —SCF₃; —SF₅; —CN; —OH; —SH; —$C_{1-5}$-alkyl; —O—$C_{1-5}$-alkyl; —S—$C_{1-5}$-alkyl; —C(=O)OH; —C(=O)—O—$C_{1-5}$-alkyl; —C(=O)—NH—CH₃, —C(=O)—NH—C₂H₅, —NH₂; —N(H)($C_{1-5}$-alkyl); —N($C_{1-5}$-alkyl)($C_{1-5}$-alkyl); —C(=O)—H; —C(=O)—$C_{1-5}$-alkyl; —C(=O)N($C_{1-5}$-alkyl)($C_{1-5}$-alkyl); —S(=O)₂ NH₂; —S(=O)₂N(H)($C_{1-5}$-alkyl); —S(=O)₂N($C_{1-5}$-alkyl)($C_{1-5}$-alkyl); —S(=O)₂-phenyl; —S(=O)₂—$C_{1-5}$-alkyl; —CH₂—NH-cyclopropyl; —CH₂—N($C_{1-5}$-alkyl)-cyclopropyl; —C(=O)—N(cyclopropyl)-$C_{1-5}$-alkyl, —N(cyclopropyl)-S(=O)₂—$C_{1-5}$-alkyl, —CH₂—NH—S(=O)₂—$C_{1-5}$-alkyl, —CH₂—N(cyclopropyl)-S(=O)₂—$C_{1-5}$-alkyl, —CH₂—N(cyclopropyl)-C(=O)—$C_{1-5}$-alkyl, —CH₂—N(cyclopropyl)-C(=O)-phenyl, phenyl; phenoxy, benzyl; thiophenyl (thienyl), furanyl and pyridinyl, the above-mentioned heteroaryl residues respectively have 5 or 6 members, 1, 2 or 3 heteroatoms independently of one another selected from the group comprising oxygen, sulphur and nitrogen as (a) ring member(s) and, where applicable, can be substituted with 1, 2, 3, 4 or 5 substituents independently of one another selected from the group comprising F; Cl; Br; I; —CF$_3$; —OCF$_3$; —SCF$_3$; —SF$_5$; —CN; —OH; —SH; —C$_{1-5}$-alkyl; —O—C$_{1-5}$-alkyl; —S—C$_{1-5}$-alkyl; —C(═O)—OH; —C(═O)—OC$_{1-5}$-alkyl; —NH$_2$; —N(H)(C$_{1-5}$-alkyl); —N(C$_{1-5}$-alkyl)(C$_{1-5}$-alkyl); —C(═O)NH$_2$; —C(═O)—NH—CH$_3$, —C(═O)—NH—C$_2$H$_5$, —C(═O)N(C$_{1-5}$-alkyl)(C$_{1-5}$-alkyl); —S(═O)$_2$NH$_2$; —S(═O)$_2$N(H)(C$_{1-5}$-alkyl); —S(═O)$_2$N(C$_{1-5}$-alkyl)(C$_{1-5}$-alkyl); —S(═O)$_2$-phenyl; —S(═O)$_2$—C$_{1-5}$-alkyl; —C(═O)—N(cyclopropyl)-C$_{1-5}$-alkyl, —N(cyclopropyl)-S(═O)$_2$—C$_{1-5}$-alkyl, —CH$_2$—NH—S(═O)$_2$—C$_{1-5}$-alkyl, —CH$_2$—N(cyclopropyl)-S(═O)$_2$—C$_{1-5}$-alkyl, —CH$_2$—N(cyclopropyl)-C(═O)—C$_{1-5}$-alkyl, —CH$_2$—N(cyclopropyl)-C(═O)-phenyl, phenyl; phenoxy, benzyl; thiophenyl (thienyl), furanyl and pyridinyl, respectively, where applicable, in the form of one of their pure stereoisomers, in particular enantiomers or diastereomers, their racemates or in the form of a mixture of stereoisomers, in particular enantiomers and/or diastereomers, in any desired mixture ratio, or respectively in the form of corresponding salts, or respectively in the form of corresponding solvates.

Compounds of the general formula I are furthermore preferred, wherein $R^1$, $R^2$, $R^3$ and $R^4$, independently of one another, respectively stand for H; F; Cl; Br; I; —CN; —SF$_5$; —NR$^7$R$^8$; —OR$^9$; —SR$^{10}$; —C(═O)OR$^{11}$; —C(═O)NR$^{12}$R$^{13}$; —S(═O)$_2$R$^{14}$; —C(═O)R$^{15}$; —NR$^{16}$—S(═O)$_2$R$^{17}$; C$_{1-4}$-alkyl, C$_{2-4}$-alkenyl, C$_{2-4}$-alkinyl; C$_{3-8}$-cycloalkyl; —(C$_{1, 2 \text{ or } 3}$-alkylene)-C$_{3-8}$-cycloalkyl; heterocycloalkyl; —(C$_{1, 2 \text{ or } 3}$-alkylene)-heterocycloalkyl; aryl; heteroaryl; —(C$_{1, 2 \text{ or } 3}$-alkylene)-aryl or —(C$_{1, 2 \text{ or } 3}$-alkylene)-heteroaryl;

whereby at least one of residues $R^1$, $R^2$, $R^3$ and $R^4$ stands for an aryl or heteroaryl residue;

$R^5$ and $R^6$, independently of one another, respectively stand for

H; —C(═O)R$^{18}$; —C(═O)NR$^{19}$R$^{20}$; —C(═S)NR$^{21}$R$^{22}$; —S(═O)$_2$R$^{23}$; C$_{1-4}$-alkyl, C$_{2-4}$-alkenyl, C$_{2-4}$-alkinyl; C$_{3-8}$-cycloalkyl; —(C$_{1, 2 \text{ or } 3}$-alkylene)-C$_{3-8}$-cycloalkyl; heterocycloalkyl; —(C$_{1, 2 \text{ or } 3}$-alkylene)-heterocycloalkyl; aryl; heteroaryl; —(C$_{1, 2 \text{ or } 3}$-alkylene)-aryl or —(C$_{1, 2 \text{ or } 3}$-alkylene)-heteroaryl;

with the proviso that $R^5$ and $R^6$ do not simultaneously stand for a residue selected from the group comprising C$_{1-4}$-alkyl and hydrogen;

or $R^5$ and $R^6$ together with the nitrogen atom which connects them form as a ring member a residue which is selected from group H comprising

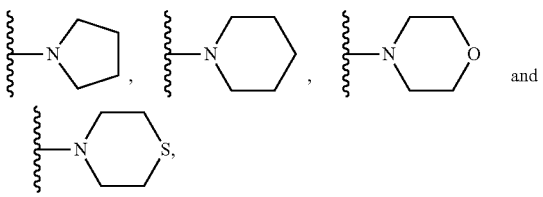

$R^7$ and $R^8$, independently of one another, respectively stand for

H, —C(═O)R$^{15}$ or C$_{1-4}$-alkyl, or $R^7$ and $R^8$ together with the nitrogen atom which connects them form as a ring member a residue which is selected from group H indicated above;

$R^9$, $R^{10}$, $R^{11}$ and $R^{16}$, independently of one another, respectively stand for H; C$_{1-4}$-alkyl, C$_{2-4}$-alkenyl, C$_{2-4}$-alkinyl; C$_{3-8}$-cycloalkyl; —(C$_{1, 2 \text{ or } 3}$-alkylene)-C$_{3-8}$-cycloalkyl; heterocycloalkyl; —(C$_{1, 2 \text{ or } 3}$-alkylene)-heterocycloalkyl; aryl; heteroaryl; —(C$_{1, 2 \text{ or } 3}$-alkylene)-aryl or —(C$_{1, 2 \text{ or } 3}$-alkylene)-heteroaryl;

$R^{12}$ and $R^{13}$, independently of one another, respectively stand for

H or for C$_{1-4}$-alkyl; or $R^{12}$ and $R^{13}$ together with the nitrogen atom which connects them form as a ring member a residue which is selected from group H indicated above;

$R^{14}$ and $R^{23}$, independently of one another, respectively stand for

—NR$^7$R$^8$; C$_{1-4}$-alkyl, C$_{2-4}$-alkenyl, C$_{2-4}$-alkinyl; C$_{3-8}$-cycloalkyl; —(C$_{1, 2 \text{ or } 3}$-alkylene)-C$_{3-8}$-cycloalkyl; heterocycloalkyl; —(C$_{1, 2 \text{ or } 3}$-alkylene)-heterocycloalkyl; aryl; heteroaryl; —(C$_{1, 2 \text{ or } 3}$-alkylene)-aryl or —(C$_{1, 2 \text{ or } 3}$-alkylene)-heteroaryl;

$R^{15}$, $R^{17}$ and $R^{18}$, independently of one another, respectively stand for C$_{1-4}$-alkyl, C$_{2-4}$-alkenyl, C$_{2-4}$-alkinyl; C$_{3-8}$-cycloalkyl; —(C$_{1, 2 \text{ or } 3}$-alkylene)-C$_{3-8}$-cycloalkyl; heterocycloalkyl; —(C$_{1, 2 \text{ or } 3}$-alkylene)-heterocycloalkyl; aryl; heteroaryl; —(C$_{1, 2 \text{ or } 3}$-alkylene)-aryl or —(C$_{1, 2 \text{ or } 3}$-alkylene)-heteroaryl;

$R^{19}$ and $R^{20}$, independently of one another, respectively stand for

H or for C$_{1-4}$-alkyl, or $R^{19}$ and $R^{20}$ together with the nitrogen atom which connects them form as a ring member a residue which is selected from group H indicated above;

$R^{21}$ and $R^{22}$, independently of one another, respectively stand for

H or for C$_{1-4}$-alkyl, or $R^{21}$ and $R^{22}$ together with the nitrogen atom which connects them form as a ring member a residue which is selected from group H indicated above;

whereby the above-mentioned C$_{1-4}$-alkyl-, C$_{2-4}$-alkenyl- and C$_{2-4}$-alkinyl residues are respectively linear or branched and, where applicable, can be substituted with 1, 2, 3, 4 or 5 substituents independently of one another selected from the group comprising F; Cl; Br; —CN; —OH; —OCH$_3$ and —NH$_2$, the above-mentioned C$_{3-8}$-cycloalkyl residues can be respectively substituted, where applicable, with 1, 2, 3, 4 or 5 substituents independently of one another selected from the group comprising F; Cl; Br; —CN; —OH; —CH$_3$; —C$_2$H$_5$; —OCH$_3$; and —NH$_2$, the above-mentioned heterocycloalkyl residues respectively have 4, 5, 6 or 7 members, have 1 or 2 heteroatoms independently of one another selected from the group comprising oxygen, sulphur and nitrogen as (a) ring member(s) and, where applicable, can be substituted with 1, 2, 3, 4 or 5 substituents independently of one another selected from the group comprising F; Cl; Br; —CN; —OH; —CH$_3$; —C$_2$H$_5$; —OCH$_3$; and —NH$_2$, the above-mentioned aryl residues respectively stand for a phenyl or naphthyl residue which can be substituted with 1, 2, 3, 4 or 5 substituents independently of one another selected from the group comprising F; Cl; Br; —CF$_3$; —OCF$_3$; —SCF$_3$; —SF$_5$; —CN; —OH; methyl; ethyl; n-propyl; isopropyl; n-butyl; isobutyl; sec-butyl; tert-butyl; methoxy; ethoxy; —NH$_2$; —N(CH$_3$)$_2$; —N(C$_2$H$_5$)$_2$; phenyl; phenoxy, benzyl; thiophenyl (thienyl), furanyl, pyridinyl, —C(═O)—NH—CH$_3$, —C(═O)—NH—

C₂H₅, —C(=O)—H, —C(=O)—CH₃, —C(=O)—C₂H₅, —C(=O)—CH(CH₃)₂, —C(=O)—C(CH₃)₃, —C(=O)—O—CH₃, —C(=O)—O—C₂H₅, —C(=O)—O—C(CH₃)₃, —C(=O)—O—CH(CH₃)₂, —C(=O)—OH, —C(=O)—N(cyclopropyl)-CH₃, —C(=O)—N(cyclopropyl)-C₂H₅, —C(=O)—N(cyclopropyl)-CH(CH₃)₂, —C(=O)—N(cyclopropyl)-C(CH₃)₃, —CH₂—NH-cyclopropyl, —CH₂—N(cyclopropyl)-S(=O)₂—CH₃, —CH₂—N(cyclopropyl)-S(=O)₂—C₂H₅, —CH₂—N(cyclopropyl)-C(=O)—CH₃, —CH₂—N(cyclopropyl)-C(=O)—C₂H₅, —CH₂—N(cyclopropyl)-C(=O)—CH(CH₃)₂, —CH₂—N(cyclopropyl)-C(=O)—C(CH₃)₃ and —CH₂—N(cyclopropyl)-C(=O)-phenyl;

the above-mentioned heteroaryl residues respectively stand for a furanyl, thienyl (thiophenyl) or pyridinyl residue and, where applicable, can be substituted with 1, 2, 3, 4 or 5 substituents independently of one another selected from the group comprising F; Cl; Br; —CF₃; —OCF₃; —SCF₃; —SF₅; —CN; —OH; methyl; ethyl; n-propyl; isopropyl; n-butyl; isobutyl; sec-butyl; tert-butyl; methoxy; ethoxy; —NH₂; —N(CH₃)₂; —N(C₂H₅)₂; phenyl; phenoxy, benzyl; thiophenyl (thienyl), furanyl, pyridinyl, —C(=O)—H, —C(=O)—CH₃, —C(=O)—C₂H₅, —C(=O)—CH(CH₃)₂, —C(=O)—C(CH₃)₃, —C(=O)—O—CH₃, —C(=O)—O—C₂H₅, —C(=O)—O—C(CH₃)₃, —C(=O)—O—CH(CH₃)₂, —C(=O)—OH, —C(=O)—NH—CH₃, —C(=O)—NH—C₂H₅, —C(=O)—N(cyclopropyl)-CH₃, —C(=O)—N(cyclopropyl)-C₂H₅, —C(=O)—N(cyclopropyl)-CH(CH₃)₂, —C(=O)—N(cyclopropyl)-C(CH₃)₃, —CH₂—NH-cyclopropyl, —CH₂—N(cyclopropyl)-S(=O)₂—CH₃, —CH₂—N(cyclopropyl)-S(=O)₂—C₂H₅, —CH₂—N(cyclopropyl)-C(=O)—CH₃, —CH₂—N(cyclopropyl)-C(=O)—C₂H₅, —CH₂—N(cyclopropyl)-C(=O)—CH(CH₃)₂, —CH₂—N(cyclopropyl)-C(=O)—C(CH₃)₃ and —CH₂—N(cyclopropyl)-C(=O)-phenyl, respectively, where applicable, in the form of one of their pure stereoisomers, in particular enantiomers or diastereomers, their racemates or in the form of a mixture of stereoisomers, in particular enantiomers and/or diastereomers, in any desired mixture ratio, or respectively in the form of corresponding salts, or respectively in the form of corresponding solvates.

Compounds of the general formula I' are particularly preferred,

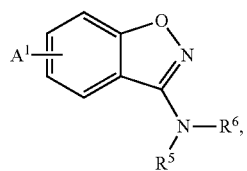

I' wherein

A¹ stands for a (hetero)aryl residue which is selected from the group comprising phenyl, 1-naphthyl, 2-naphthyl, thiophenyl (thienyl), furanyl and pyridinyl and which, where applicable, can be substituted with 1, 2, 3, 4 or 5 substituents independently of one another selected from the group comprising F; Cl; Br; —CF₃; —OCF₃; —SCF₃; —SF₅; —CN; —OH; methyl; ethyl; n-propyl; isopropyl; n-butyl; isobutyl; sec-butyl; tert-butyl; methoxy; ethoxy; —NH₂; —N(CH₃)₂; —N(C₂H₅)₂; phenyl; phenoxy, benzyl; thiophenyl (thienyl), furanyl, pyridinyl, —C(=O)—NH—CH₃, —C(=O)—NH—C₂H₅, —C(=O)—H, —C(=O)—CH₃, —C(=O)—C₂H₅, —C(=O)—CH(CH₃)₂, —C(=O)—C(CH₃)₃, —C(=O)—O—CH₃, —C(=O)—O—C₂H₅, —C(=O)—O—C(CH₃)₃, —C(=O)—O—CH(CH₃)₂, —C(=O)—OH, —C(=O)—N(cyclopropyl)-CH₃, —C(=O)—N(cyclopropyl)-C₂H₅, —C(=O)—N(cyclopropyl)-CH(CH₃)₂, —C(=O)—N(cyclopropyl)-C(CH₃)₃, —CH₂—NH-cyclopropyl, —CH₂—N(cyclopropyl)-S(=O)₂—CH₃, —CH₂—N(cyclopropyl)-S(=O)₂—C₂H₅, —CH₂—N(cyclopropyl)-C(=O)—CH₃, —CH₂—N(cyclopropyl)-C(=O)—C₂H₅, —CH₂—N(cyclopropyl)-C(=O)—CH(CH₃)₂, —CH₂—N(cyclopropyl)-C(=O)—C(CH₃)₃ and —CH₂—N(cyclopropyl)-C(=O)-phenyl;

R⁵ and R⁶, independently of one another, respectively stand for

H; an alkyl residue selected from the group comprising methyl; ethyl; n-propyl; isopropyl; n-butyl; isobutyl; sec-butyl, tert-butyl, n-pentyl and neopentyl; for —C(=O)-phenyl; —(CH₂)-phenyl; —(CH₂)₂-phenyl; —(CH₂)₃-phenyl; —(CH₂)-pyridinyl; —(CH₂)₂-pyridinyl; or —(CH₂)₃-pyridinyl; whereby the above-mentioned phenyl and pyridinyl residues, where applicable, can be substituted with 1, 2, 3, 4 or 5 substituents independently of one another selected from the group comprising F; Cl; Br; —CF₃; —OCF₃; —SCF₃; —SF₅; —CN; —OH; methyl; ethyl; n-propyl; isopropyl; n-butyl; isobutyl; sec-butyl; tert-butyl; methoxy; ethoxy; —NH₂; —N(CH₃)₂; —N(C₂H₅)₂; phenyl; phenoxy, benzyl; thiophenyl (thienyl), furanyl and pyridinyl;

with the proviso that R⁵ and R⁶ do not simultaneously stand for a residue selected from the group comprising alkyl residues and hydrogen;

or

R⁵ and R⁶ together with the nitrogen atom which connects them form as a ring member a residue which is selected from group H comprising

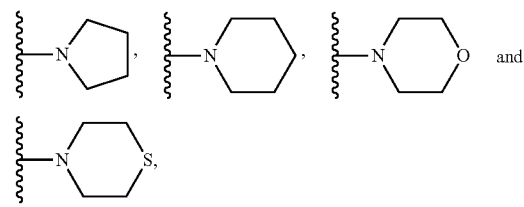

respectively, where applicable, in the form of corresponding salts, in particular hydrochloride addition salts, or respectively in the form of corresponding solvates.

Compounds according to the invention of the general formula I-A, I-B, I-C and I-D are furthermore preferred,

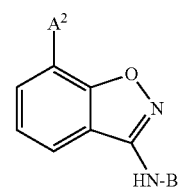

I-A

-continued

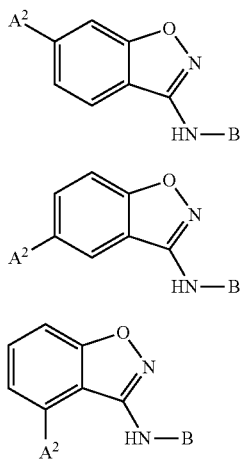

I-B

I-C

I-D wherein respectively

A² stands for a (hetero)aryl residue which is selected from the group comprising phenyl, 1-naphthyl, 2-naphthyl, thiophenyl (thienyl), furanyl and pyridinyl and which can be substituted, where applicable, with 1, 2, 3, 4 or 5 substituents independently of one another selected from the group comprising F; Cl; Br; —$CF_3$; —$OCF_3$; —$SCF_3$; —$SF_5$; —CN; —OH; methyl; ethyl; n-propyl; isopropyl; n-butyl; isobutyl; sec-butyl; tert-butyl; methoxy; ethoxy; —$NH_2$; —$N(CH_3)_2$; —$N(C_2H_5)_2$;

phenyl; phenoxy, benzyl; thiophenyl (thienyl), furanyl, pyridinyl, —C(═O)—NH—$CH_3$, —C(═O)—NH—$C_2H_5$, —C(═O)—H, —C(═O)—$CH_3$, —C(═O)—$C_2H_5$, —C(═O)—$CH(CH_3)_2$, —C(═O)—$C(CH_3)_3$, —C(═O)—O—$CH_3$, —C(═O)—O—$C_2H_5$, —C(═O)—O—$C(CH_3)_3$, —C(═O)—O—$CH(CH_3)_2$, —C(═O)—OH, —C(═O)—N(cyclopropyl)-$CH_3$, —C(═O)—N(cyclopropyl)-$C_2H_5$, —C(═O)—N(cyclopropyl)-$CH(CH_3)_2$, —C(═O)—N(cyclopropyl)-$C(CH_3)_3$, —$CH_2$—NH-cyclopropyl, —$CH_2$—N(cyclopropyl)-S(═O)$_2$—$CH_3$, —$CH_2$—N(cyclopropyl)-S(═O)$_2$—$C_2H_5$, —$CH_2$—N(cyclopropyl)-C(═O)—$CH_3$, —$CH_2$—N(cyclopropyl)-C(═O)—$C_2H_5$, —$CH_2$—N(cyclopropyl)-C(═O)—$CH(CH_3)_2$, —$CH_2$—N(cyclopropyl)-C(═O)—$C(CH_3)_3$ and —$CH_2$—N(cyclopropyl)-C(═O)-phenyl;

B stands for —C(═O)-phenyl; —($CH_2$)-phenyl; —($CH_2$)$_2$-phenyl; —($CH_2$)$_3$-phenyl; —($CH_2$)-pyridinyl; —($CH_2$)$_2$-pyridinyl or —($CH_2$)$_3$-pyridinyl; whereby the above-mentioned phenyl and pyridinyl residues can be substituted, where applicable, with 1, 2, 3, 4 or 5 substituents independently of one another selected from the group comprising F; Cl; Br; —$CF_3$; —$OCF_3$; —$SCF_3$; —$SF_5$; —CN; —OH; methyl; ethyl; n-propyl; isopropyl; n-butyl; isobutyl; sec-butyl; tert-butyl; methoxy; ethoxy; —$NH_2$; —$N(CH_3)_2$; —$N(C_2H_5)_2$; phenyl; phenoxy, benzyl; thiophenyl (thienyl), furanyl and pyridinyl, respectively, where applicable, in the form of corresponding salts, in particular hydrochloride addition salts, or respectively in the form of corresponding solvates.

Compounds according to the invention of the general formulae I-A, I-B, I-C and I-D are particularly preferred, wherein respectively A² stands for one of the following residues A²¹ or A²²:

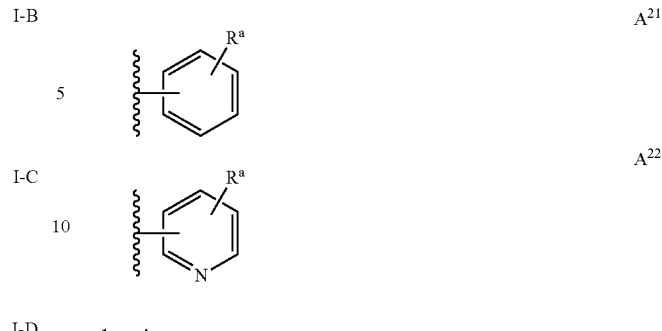

wherein

R$^a$ respectively stands for a residue which is selected from the group comprising H, F, Cl, Br, I, —CN; —$CF_3$, —$OCF_3$, —$SCF_3$, —$SF_5$, —OH, —SH, methyl; ethyl; n-propyl; isopropyl; n-butyl; isobutyl; sec-butyl; tert-butyl; —C(═O)—NH—$CH_3$, —C(═O)—NH—$C_2H_5$, —$OCH_3$; —$OC_2H_5$; —S—$CH_3$, —S—$C_2H_5$, —C(═O)—H, —C(═O)—O—$C_2H_5$, —C(═O)—OH, —$CH_2$—NH-cyclopropyl, —$CH_2$—N(cyclopropyl)-S(═O)$_2$—$CH_3$, —$CH_2$—N(cyclopropyl)-C(═O)—$CH_3$ and —$CH_2$—N(cyclopropyl)-C(═O)-phenyl and B stands for one of following residues B¹, B² or B³,

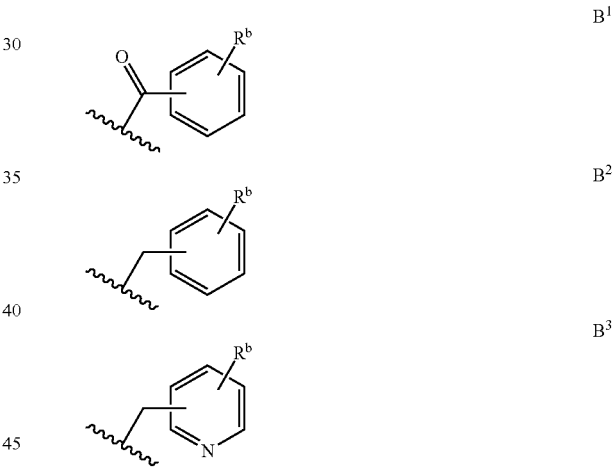

wherein

R$^b$ respectively stands for a residue which is selected from the group comprising H, F, Cl, Br, I, —CN; —$CF_3$, —$OCF_3$, —$SCF_3$, —$SF_5$, —OH, —SH, methyl; ethyl; n-propyl; isopropyl; n-butyl; isobutyl; sec-butyl; tert-butyl; —$OCH_3$; —$OC_2H_5$; —S—$CH_3$ and —S—$C_2H_5$.

respectively, where applicable, in the form of corresponding salts, in particular hydrochloride addition salts, or respectively in the form of corresponding solvates.

The substituted benzo[d]isoxazol-3-yl-amine compounds according to the invention are preferably not substituted in their 3-position with a free amino group, i.e. residues R⁵ and R⁶ according to the invention do not simultaneously stand for a hydrogen residue.

Compounds according to the invention are most preferred selected from the group comprising

[1] Benzyl-[6-(3-chloro-phenyl)-benzo[d]isoxazol-3-yl]-amine,

[2] Benzyl-[6-(4-chloro-phenyl)-benzo[d]isoxazol-3-yl]-amine,

[3] Benzyl-(6-p-tolyl-benzo[d]isoxazol-3-yl)-amine,
[4] Benzyl-[6-(2-methoxy-phenyl)-benzo[d]isoxazol-3-yl]-amine,
[5] N-[6-(3-chloro-phenyl)-benzo[d]isoxazol-3-yl]-benzamide,
[6] N-[6-(4-chloro-phenyl)-benzo[d]isoxazol-3-yl]-benzamide,
[7] N-(6-p-tolyl-benzo[d]isoxazol-3-yl)-benzamide,
[8] N-[6-(2-methoxy-phenyl)-benzo[d]isoxazol-3-yl]-benzamide,
[9] (4-tert-butyl-benzyl)-(6-pyridine-2-yl-benzo[d]isoxazol-3-yl)-amine,
[10] (4-tert-butyl-benzyl)-[6-(3-methyl-pyridine-2-yl)-benzo[d]isoxazol-3-yl]-amine,
[11] (4-tert-butyl-benzyl)-[6-(6-methyl-pyridine-2-yl)-benzo[d]isoxazol-3-yl]-amine,
[12] (4-tert-butyl-benzyl)-(6-phenyl-benzo[d]isoxazol-3-yl)-amine,
[13] [6-(4-chloro-phenyl)-benzo[d]isoxazol-3-yl]-pyridine-2-ylmethyl-amine,
[14] (6-phenyl-benzo[d]isoxazol-3-yl)-pyridine-2-ylmethyl-amine,
[15] Pyridine-2-ylmethyl-(6-o-tolyl-benzo[d]isoxazol-3-yl)-amine,
[16] [6-(4-chloro-phenyl)-benzo[d]isoxazol-3-yl]-pyridine-3-ylmethyl-amine,
[17] (6-phenyl-benzo[d]isoxazol-3-yl)-pyridine-3-ylmethyl-amine,
[18] Pyridine-3-ylmethyl-(6-o-tolyl-benzo[d]isoxazol-3-yl)-amine,
[19] 2-{3-[(pyridine-3-ylmethyl)-amino]-benzo[d]isoxazol-6-yl}-phenol,
[20] [6-(4-chloro-phenyl)-benzo[d]isoxazol-3-yl]-pyridine-4-ylmethyl-amine,
[21] (6-phenyl-benzo[d]isoxazol-3-yl)-pyridine-4-ylmethyl-amine,
[22] Pyridine-4-ylmethyl-(6-o-tolyl-benzo[d]isoxazol-3-yl)-amine,
[23] 4-{[6-(4-chloro-phenyl)-benzo[d]isoxazol-3-ylamino]-methyl}-benzonitrile,
[24] 4-[(6-phenyl-benzo[d]isoxazol-3-ylamino)-methyl]-benzonitrile,
[25] 4-[(6-o-tolyl-benzo[d]isoxazol-3-ylamino)-methyl]-benzonitrile,
[26] 4-{[6-(2-hydroxy-phenyl)-benzo[d]isoxazol-3-ylamino]-methyl}-benzonitrile,
[27] [6-(4-chloro-phenyl)-benzo[d]isoxazol-3-yl]-(3-methyl-benzyl)-amine,
[28] (3-methyl-benzyl)-(6-phenyl-benzo[d]isoxazol-3-yl)-amine,
[29] (3-methyl-benzyl)-(6-o-tolyl-benzo[d]isoxazol-3-yl)-amine,
[30] 2-[3-(3-methyl-benzylamino)-benzo[d]isoxazol-6-yl]-phenol,
[31] (3-chloro-benzyl)-[6-(4-chloro-phenyl)-benzo[d]isoxazol-3-yl]-amine,
[32] (3-chloro-benzyl)-(6-phenyl-benzo[d]isoxazol-3-yl)-amine,
[33] (3-chloro-benzyl)-(6-o-tolyl-benzo[d]isoxazol-3-yl)-amine and
[34] 2-[3-(3-chloro-benzylamino)-benzo[d]isoxazol-6-yl]-phenol,
and respectively their corresponding salts, in particular their hydrochloride addition salts, and, where applicable, respectively their corresponding solvates.

Substituted benzo[d]isoxazol-3-yl-amine compounds according to the invention can furthermore be preferred which have in the FLIPR assay in a concentration of 10 μM an inhibition of the $Ca^{2+}$ ion inflow in dorsal root ganglia of rats of at least 10%, preferably of at least 30%, particularly preferably of at least 50%, very particularly preferably of at least 70%, even more preferably of at least 90%, in comparison to the maximum achievable inhibition of the $Ca^{2+}$ ion inflow with capsaicin in a concentration of 10 μM.

Thereby, in the FLIPR assay, the $Ca^{2+}$ inflow is quantified with the help of a $Ca^{2+}$-sensitive dye (type Fluo-4, Molecular Probes Europe BV, Leiden Netherlands) in the Fluorescent Imaging Plate Reader (FLIPR, Molecular Devices, Sunnyvale, USA), as described below.

A further subject matter of the present invention is a method for producing the substituted benzo[d]isoxazol-3-yl-amine compounds according to the invention, according to which a, where applicable, substituted 2-fluoro-benzonitrile compound of the general formula II,

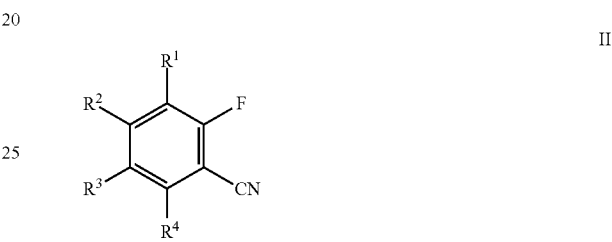

wherein residues $R^1$, $R^2$, $R^3$ and $R^4$ have the meaning indicated above, in a reaction medium, preferably selected from the group comprising diethyl ether, tetrahydrofuran, acetonitrile, dimethyl sulphoxide, dimethylformamide and dichloromethane, in the presence of a base, preferably in the presence of at least one alkali metal alcoholate salt, particularly preferably in the presence of an alkali metal alcoholate salt selected from the group comprising potassium methoxide, sodium methoxide, potassium t-butoxide and sodium t-butoxide with acetohydroxamic acid of the formula III

preferably at temperatures of 20° C. to 100° C. is transformed into a compound of the general formula I,

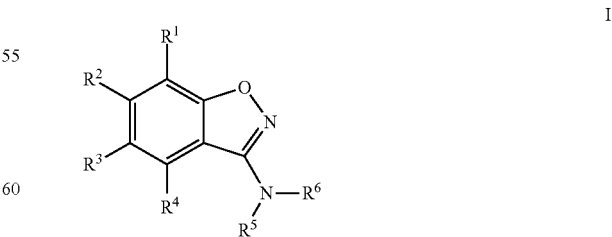

wherein residues $R^1$-$R^4$ have the meaning indicated above and residues $R^5$ and $R^6$ respectively stand for a hydrogen residue, the latter compound is purified where applicable and/or isolated where applicable, and the latter compound is, where applicable, subsequently transformed in a reaction medium, preferably selected from the group comprising acetonitrile, toluene, dimethylformamide, benzene, ethanol, methanol and corresponding mixtures, with at least one isocyanate of the general formula $R^{19}$—N=C=O, wherein $R^{19}$ has the meaning indicated above, where applicable, in the presence of at least one base, preferably in the presence of at least one base selected from the group comprising triethylamine, 4,4-dimethylaminopyridine and diisopropylethylamine, into at least one compound of the general formula I, wherein $R^1$, $R^2$, $R^3$, $R^4$ have the meaning indicated above, $R^5$ stands for a hydrogen residue and $R^6$ stands for —C(=O)—$NR^{19}R^{20}$, whereby $R^{19}$ has the meaning indicated above and $R^{20}$ stands for a hydrogen residue, and the latter compound is purified where applicable and/or isolated where applicable or and the latter compound is, where applicable, subsequently transformed in a reaction medium, preferably selected from the group comprising acetonitrile, toluene, dimethylformamide, benzene, ethanol, methanol and corresponding mixtures, with at least one isothiocyanate of the general formula S=C=N—$R^{21}$, wherein $R^{21}$ has the meaning indicated above, where applicable, in the presence of at least one base, preferably in the presence of at least one base selected from the group comprising triethylamine, 4,4-dimethylaminopyridine and diisopropylethylamine, into at least one compound of the general formula I, wherein $R^1$, $R^2$, $R^3$, $R^4$ have the meaning indicated above, $R^5$ stands for a hydrogen residue and $R^6$ stands for —C(=S)—$NR^{21}R^{22}$, whereby $R^{21}$ has the meaning indicated above and $R^{22}$ stands for a hydrogen residue, and the latter compound is purified where applicable and/or isolated where applicable, and, where applicable, a compound of the general formula I, wherein $R^1$, $R^2$, $R^3$, $R^4$ have the meaning indicated above, $R^5$ stands for a hydrogen residue and $R^6$ stands for —C(=O)—$NR^{19}R^{20}$ or for —C(=S)—$NR^{21}R^{22}$, whereby $R^{19}$ and $R^{21}$ have the meaning indicated above and $R^{20}$ and $R^{22}$ respectively stand for a hydrogen residue, is transformed in a reaction medium, preferably selected from the group comprising acetonitrile, toluene, dimethylformamide, benzene, ethanol, methanol and corresponding mixtures, in the presence of at least one base, preferably in the presence of at least one metal hydride salt or a metal alcoholate salt, particularly preferably in the presence of a metal hydride salt or a metal alcoholate salt selected from the group comprising sodium hydride, potassium hydride, potassium t-butoxide, sodium t-butoxide, potassium methoxide, sodium methoxide, sodium methoxide and potassium methoxide, with at least one compound of the general formula LG-$R^{20}$ or the general formula LG-$R^{22}$, wherein LG stands for a leaving group, preferably for a halogen atom, particularly preferably for a chlorine atom, and $R^{20}$ and $R^{22}$ respectively have the meaning indicated above with the exception of hydrogen, into at least one compound of the general formula I and the latter compound is purified where applicable and/or isolated where applicable, or where applicable, at least one compound of the general formula I, wherein $R^1$, $R^2$, $R^3$, $R^4$ have the meaning indicated above and $R^5$ and $R^6$ respectively stand for H, is transformed in a reaction medium, preferably selected from the group comprising acetonitrile, toluene, dimethylformamide, benzene, ethanol, methanol and corresponding mixtures, in the presence of at least one base, preferably in the presence of at least one metal hydride salt or a metal alcoholate salt, particularly preferably in the presence of a metal hydride salt or a metal alcoholate salt selected from the group comprising sodium hydride, potassium hydride, potassium t-butoxide, sodium t-butoxide, potassium methoxide, sodium methoxide, sodium methoxide and potassium methoxide, with at least one compound of the general formula LG-$R^5$ or the general formula LG-$R^6$, wherein LG stands for a leaving group, preferably for a halogen atom, particularly preferably for a chlorine atom, and $R^5$ and $R^6$ respectively have the meaning indicated above, into at least one compound of the general formula I and the latter compound is purified where applicable and/or isolated where applicable, or at least one compound of the general formula I, wherein residues $R^1$-$R^4$ have the meaning indicated above and residues $R^5$ and $R^6$ respectively stand for H, is transformed in a reaction medium, preferably dichloromethane, in the presence of at least one reducing agent, preferably in the presence of trifluoroacetic acid and triethylsilane, with at least one compound of the general formula $R^5$—(C=O)—H, wherein $R^5$ has the meaning indicated above with the exception of H, —C(=O)$R^{18}$, —C(=O)—$NR^{19}R^{20}$, —C(=S)—$NR^{21}R^{22}$ and —S(=O)$_2R^{23}$, into at least one compound of the general formula I and the latter compound is purified where applicable and/or isolated where applicable, or at least one compound of the general formula I, wherein residues $R^1$-$R^4$ have the meaning indicated above and residues $R^5$ and $R^6$ respectively stand for H, is transformed in a reaction medium, preferably pyridine, with at least one compound of the general formula $R^{18}$—C(=O)-LG, wherein $R^{18}$ has the meaning indicated above and LG stands for a leaving group, preferably for a halogen atom, particularly preferably for a chlorine atom, into at least one compound of the general formula I, wherein $R^1$ to $R^4$ have the meaning indicated above, $R^5$ stands for a —C(=O)$R^{18}$ residue and $R^6$ stands for a hydrogen residue; and the latter compound is purified where applicable and/or isolated where applicable, or at least one compound of the general formula I, wherein residues $R^1$-$R^4$ have the meaning indicated above and residues $R^5$ and $R^6$ respectively stand for H, is transformed in a reaction medium, preferably selected from the group comprising diethylether, tetrahydrofuran, acetonitrile, methanol, ethanol, dimethylformamide, dichloromethane and corresponding mixtures, in the presence of at least one coupling reagent, preferably selected from the group comprising 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCI), N-[(dimethyamino)-1H-1,2,3-triazolo[4,5-b]pyridino-1-ylmethylene]-N-methylmethanaminium hexafluorophosphate N-oxide (HATU), O-(benzotriazol-1-yl)-N,N,N',N'-tetramethyluroniom hexafluorophosphate (HBTU), O-(benzotriazol-1-yl)-N,N,N', N'-tetramethyluroniom tetrafluoroborate (TBTU), 1-hydroxybenzotriazol (HOBt) and 1-hydroxy-7-azabenzotriazol (HOAt), where applicable in the presence of at least one inorganic base, preferably selected from the group comprising potassium carbonate and caesium carbonate, or an organic basis, preferably selected from the group comprising triethylamine, N-methylmorpholine, pyridine, N,N-dimethylaminopyridine and diisopropylethylamine preferably at temperatures of −70° C. to 100° C. with at least one compound of the general formula $R^{18}$—C(=O)—OH, wherein $R^{18}$ has the meaning indicated above, into at least one compound of the general formula I, wherein $R^1$ to $R^4$ have the meaning indicated above, $R^5$ stands for a —C(=O)$R^{18}$ residue and $R^6$ stands for a hydrogen residue; and the latter compound is purified where applicable and/or isolated where applicable, or at least one compound of the general formula I, wherein residues $R^1$-$R^4$ have the meaning indicated above and residues $R^5$ and $R^6$ respectively stand for H, is transformed in a reaction medium, preferably selected from the group comprising acetonitrile, toluene, dimethylformamide, benzene, ethanol, methanol and corresponding mixtures, where applicable in the presence of at least one inorganic base, preferably selected from the group comprising potassium carbonate and caesium carbonate, or an organic base, preferably selected from the group comprising triethylamine, N-methylmorpholine, pyridine, N,N-dimethylaminopyridine and diisopropylethylamine, with at least one compound of the general formula $R^{23}$—S(=O)$_2$-LG, wherein $R^{23}$ has the meaning indicated above and LG stands for a leaving group, preferably for a halogen atom, particularly preferably for a chlorine atom, into at least one compound of the general formula I, wherein $R^1$ to $R^4$ have the meaning indicated above, $R^5$ stands for a —S(=O)$_2$—$R^{23}$ group and $R^6$ for a hydrogen residue, and the latter compound is purified where applicable and/or isolated where applicable.

A further object of the present invention is a method for producing benzo[d]isoxazol-3-yl-amine compounds according to the invention, according to which a where applicable substituted 2-fluoro-benzonitrile compound of the general formula II,

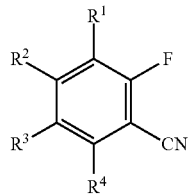

II wherein one of residues $R^1$, $R^2$, $R^3$ and $R^4$ stands for a leaving group, preferably for a bromine atom, is transformed in a reaction medium, preferably selected from the group comprising diethylether, tetrahydrofuran, acetonitrile, dimethyl sulphoxide, dimethylformamide and dichloromethane, in the presence of a base, preferably in the presence of at least one alkali metal alcoholate salt, particularly preferably in the presence of an alkali metal alcoholate salt selected from the group comprising potassium methoxide, sodium methoxide, potassium t-butoxide and sodium t-butoxide with acetohydroxamic acid of the formula III

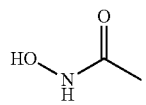

III preferably at temperatures of 20° C. to 100° C. into a compound of the general formula I,

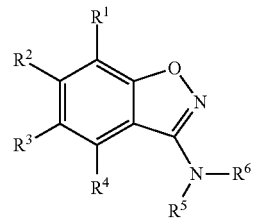

I wherein residues $R^1$-$R^4$ have the meaning indicated above and residues $R^5$ and $R^6$ respectively stand for a hydrogen residue, the latter compound is where applicable purified and/or isolated where applicable, and latter compound, where applicable, is subsequently transformed in a reaction medium, preferably selected from the group comprising acetonitrile, toluene, dimethylformamide, benzene, ethanol, methanol and corresponding mixtures, with at least one isocyanate of the general formula $R^{19}$—N=C=O, wherein $R^{19}$ has the meaning indicated above, where applicable in the presence of a base, preferably in the presence of at least one base selected from the group comprising triethylamine, 4,4-dimethylaminopyridine and diisopropylethylamine, into at least one compound of the general formula I, wherein $R^1$, $R^2$, $R^3$, $R^4$ have the meaning indicated above, $R^5$ stands for a hydrogen residue and $R^6$ stands for —C(=O)—NR$^{19}$R$^{20}$, whereby $R^{19}$ has the meaning indicated above and $R^{20}$ stands for a hydrogen residue, and the latter compound is purified where applicable and/or isolated where applicable or the latter compound, where applicable, is subsequently transformed in a reaction medium, preferably selected from the group comprising acetonitrile, toluene, dimethylformamide, benzene, ethanol, methanol and corresponding mixtures, with at least one isothiocyanate of the general formula S=C=N—$R^{21}$, wherein $R^{21}$ has the meaning indicated above, where applicable in the presence of at least one base, preferably in the presence of at least one base selected from the group comprising triethylamine, 4,4-dimethylaminopyridine and diisopropylethylamine, into at least one compound of the general formula I, wherein $R^1$, $R^2$, $R^3$, $R^4$ have the meaning indicated above, $R^5$ stands for a hydrogen residue and $R^6$ stands for —C(=S)—NR$^{21}$R$^{22}$, wherein $R^{21}$ has the meaning indicated above and $R^{22}$ stands for a hydrogen residue, and the latter compound is purified where applicable and/or isolated where applicable, and where applicable at least one compound of the general formula I, wherein $R^1$, $R^2$, $R^3$, $R^4$ have the meaning indicated above, $R^5$ stands for a hydrogen residue and $R^6$ stands for —C(=O)—NR$^{19}$R$^{20}$ or for —C(=S)—NR$^{21}$R$^{22}$, whereby $R^{10}$ and $R^{21}$ have the meaning indicated above and $R^{20}$ and $R^{22}$ respectively stand for a hydrogen residue, is transformed in a reaction medium, preferably selected from the group comprising acetonitrile, toluene, dimethylformamide, benzene, ethanol, methanol and corresponding mixtures, in the presence of at least one base, preferably in the presence of at least one metal hydride salt or a metal alcoholate salt, particularly preferably in the presence of a metal hydride salt or a metal alcoholate salt selected from the group comprising sodium hydride, potassium hydride, potassium t-butoxide, sodium t-butoxide, potassium methoxide, sodium methoxide, sodium methoxide and potassium methoxide, with at least one compound of the general formula LG-R$^{20}$ or the general formula LG-R$^{22}$, wherein LG stands for a leaving group, preferably for a halogen atom, particularly preferably for a chlorine atom, and R$^{20}$ and R$^{22}$ respectively have the meaning indicated above with the exception of hydrogen, into at least one compound of the general formula I, and the latter compound is purified where applicable and/or is isolated where applicable, where applicable at least one compound of the general formula I, wherein R$^1$, R$^2$, R$^3$, R$^4$ have the meaning indicated above and R$^5$ and R$^6$ respectively stand for H, is transformed in a reaction medium, preferably selected from the group comprising acetonitrile, toluene, dimethylformamide, benzene, ethanol, methanol and corresponding mixtures, in the presence of at least one base, preferably in the presence of at least one metal hydride salt or a metal alcoholate salt, particularly preferably in the presence of a metal hydride salt or a metal alcoholate salt selected from the group comprising sodium hydride, potassium hydride, potassium t-butoxide, sodium t-butoxide, potassium methoxide, sodium methoxide, sodium methoxide and potassium methoxide, with at least one compound of the general formula LG-R$^5$ or the general formula LG-R$^6$, wherein LG stands for a leaving group, preferably for a halogen atom, particularly preferably for a chlorine atom, and R$^5$ and R$^6$ respectively have the meaning indicated above, into at least one compound of the general formula I, and the latter compound is purified where applicable and/or isolated where applicable, or at least one compound of the general formula I, wherein residues R$^1$-R$^4$ have the meaning indicated above and residues R$^5$ and R$^6$ respectively stand for H, is transformed in a reaction medium, preferably dichloromethane, in the presence of at least one reducing agent, particularly preferably in the presence of trifluoroacetic acid and triethylsilane, with at least one compound of the general formula R$^5$—(C=O)—H, wherein R$^5$ has the meaning indicated above with the exception of H, —C(=O)R$^{18}$, —C(=O)—NR$^{19}$R$^{20}$, —C(=S)—NR$^{21}$R$^{22}$ and —S(=O)$_2$R$^{23}$, into at least compound of the general formula I, and the latter compound is purified where applicable and/or isolated where applicable, or at least one compound of the general formula I, wherein residues R$^1$-R$^4$ have the meaning indicated above and residues R$^5$ and R$^6$ respectively stand for H, is transformed in a reaction medium, preferably pyridine, with at least one compound of the general formula R$^{18}$—C(=O)-LG, wherein R$^{18}$ has the meaning indicated above and LG stands for a leaving group, preferably for a halogen atom, particularly preferably for a chlorine atom, into at least compound of the general formula I, wherein R$^1$ to R$^4$ have the meaning indicated above, R$^5$ stands for a —C(=O)R$^{18}$ residue and R$^6$ stands for a hydrogen residue; and the latter compound is purified where applicable and/or isolated where applicable, or at least one compound of the general formula I, wherein residues R$^1$-R$^4$ have the meaning indicated above and residues R$^5$ and R$^6$ respectively stand for H, is transformed in a reaction medium, preferably selected from the group comprising diethylether, tetrahydrofuran, acetonitrile, methanol, ethanol, dimethylformamide, dichloromethane and corresponding mixtures, in the presence of at least one coupling reagent, preferably selected from the group comprising 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCI), N-[(dimethyamino)-1H-1,2,3-triazolo[4,5-b]pyridino-1-ylmethylene]-N-methylmethanaminium hexafluorophosphate N-oxide (HATU), O-(benzotriazol-1-yl)-N,N,N',N'-tetramethyluroniom hexafluorophosphate (HBTU), O-(benzotriazol-1-yl)-N,N,N',N'-tetramethyluroniom tetrafluoroborate (TBTU), 1-hydroxybenzotriazol (HOBt) and 1-hydroxy-7-azabenzotriazol (HOAt), where applicable in the presence of at least one inorganic base, preferably selected from the group comprising potassium carbonate and caesium carbonate, or an organic base, preferably selected from the group comprising triethylamine, N-methylmorpholine, pyridine, N,N-dimethylaminopyridine and diisopropylethylamine preferably at temperatures of −70° C. to 100° C. with at least one compound of the general formula R$^{18}$—C(=O)—OH, wherein R$^{18}$ has the meaning indicated above, into at least one compound of the general formula I, wherein R$^1$ to R$^4$ have the meaning indicated above, R$^5$ stands for a —C(=O)R$^{18}$ residue and R$^6$ stands for a hydrogen residue; and the latter compound is purified where applicable and/or isolated where applicable, or at least one compound of the general formula I, wherein residues R$^1$-R$^4$ have the meaning indicated above and residues R$^5$ and R$^6$ respectively stand for H, is transformed in a reaction medium, preferably selected from the group comprising acetonitrile, toluene, dimethylformamide, benzene, ethanol, methanol and corresponding mixtures, where applicable in the presence of at least one inorganic base, preferably selected from the group comprising potassium carbonate and caesium carbonate, or an organic base, preferably selected from the group comprising triethylamine, N-methylmorpholine, pyridine, N,N-dimethylaminopyridine and diisopropylethylamine, with at least one compound of the general formula R$^{23}$—S(=O)$_2$-LG, wherein R$^{23}$ has the meaning indicated above and LG stands for a leaving group, preferably for a halogen atom, particularly preferably for a chlorine atom, into at least one compound of the general formula I, wherein R$^1$ to R$^4$ have the meaning indicated above, R$^5$ stands for a —S(=O)$_2$—R$^{23}$ group and R$^6$ stands for a hydrogen residue, and the latter compound is purified where applicable and/or isolated where applicable, and respectively the compound obtained in this manner of the general formula I, in which at least one of residues R$^1$ to R$^4$ stands for a leaving group, preferably for a halogen residue or a sulphonic acid ester, particularly preferably for a leaving group selected from the group comprising chlorine, bromine, iodine, triflate, mesylate and tosylate, very particularly preferably for a bromine atom, and the remaining residues have the meaning indicated above, where applicable in at least one reaction medium, preferably in at least one reaction medium selected from the group comprising methanol, ethylacetate, ethanol, isopropanol, diethylether, dimethoxyethane, dioxane, tetrahydrofuran, dimethylformamide, acetonitrile, dimethyl sulphoxide, toluene, N-methyl-pyrrolidine and water or corresponding mixtures, where applicable in the presence of at least one base and one catalyst which can be polymer-bonded, preferably in the presence of at least one base selected from the group comprising potassium carbonate, sodium carbonate, potassium phosphate, sodium hydrogen phosphate, caesium carbonate, triethylamine, [1,4]-diazabicyclo-[2.2.2]-octane, diisopropylamine, diisopropylethylamine and N-methylmorpholine and a catalyst which can be polymer-bonded selected from the group comprising palladium(II)acetate, tris(dibenzylidenacetone)dipalladium, palladium(0)bis(dibenzylidenacetone), tetrakis(triphenylphosphine)palladium(0), (1,1'-bis(diphenylphosphino)-ferrocene)dichloropalladium(II), bis(acetonitrile)dichloropalladium(II), palladium(II)chloride, dichlorobis(triphenyl-phosphine)palladium(II), dichloro(tricyclohexylphosphine)palladium(II), bis(acetato)bis(triphenylphosphine)-palladium(II), bistriphenylphosphine-palladium(II)dichloride, bistriphenyl-phosphine-palladium(II)acetate and iron(III)chloride, particularly preferably in the presence of an alkali carbonate and a palladium catalyst, very particularly preferably in the presence of sodium carbonate and tetrakis(triphenylphosphine)-palladium(0), where applicable in the presence of at least one ligand which can be polymer-bonded, preferably in the presence of at least one ligand which can be polymer-bonded selected from the group comprising 2-dicyclohexylphosphino-2',6'-dimethoxybiphenyl (S-Phos), 2-dicyclohexylphosphino-2',4',6'-triisopropylbiphenyl (X-Phos), tricyclohexylphosphine, tricyclohexylphosphine tetrafluoroborate, tri-tert-butylphosphine tetrafluoroborate, triphenylphosphine and imidazolium salts, where applicable using microwave radiation, transforms with at least one boronic acid compound of the following formula,

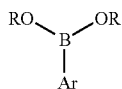

wherein Ar stands for an unsubstituted or at least monosubstituted aryl or heteroaryl residue with the meaning indicated above and R for hydrogen or an organic residue, preferably for hydrogen or an alkyl residue or two residues R together with the —O—B—O-group which connects them form a heterocycloalkyl residue, and the compound obtained in this manner of the general formula I, in which at least one of residues $R^1$ to $R^4$ stands for an unsubstituted or at least monosubstituted aryl or heteroaryl residue, purifies where applicable and/or isolates where applicable, or respectively the compound obtained in this manner of the general formula I, in which at least one of residues $R^1$ to $R^4$ stands for a leaving group, preferably for a halogen residue or a sulphonic acid ester, particularly preferably for a leaving group selected from the group comprising chlorine, bromine, iodine, triflate, mesylate and tosylate, very particularly preferably for a bromine atom, and the remaining residues have the meaning indicated above, with an organometal compound of the general formula R'-M-X, wherein R' stands for an unsubstituted or at least monosubstituted aryl or heteroaryl residue with the meaning indicated above, M for a transition metal ion, preferably for a magnesium or zinc ion, and X for a leaving group, preferably for a halogen residue or a sulphonic acid ester, particularly preferably for a leaving group selected from the group comprising chlorine, bromine, iodine, triflate, mesylate and tosylate, very particularly preferably for a bromine atom, transforms where applicable in at least one reaction medium, preferably in at least one reaction medium selected from the group comprising methanol, ethylacetate, ethanol, isopropanol, diethylether, dimethoxyethane, dioxane, tetrahydrofuran, dimethylformamide, acetonitrile, dimethyl sulphoxide, toluene, N-methyl-pyrrolidine and water or corresponding mixtures, where applicable in the presence of at least one catalyst which can be polymer-bonded, preferably in the presence of a catalyst which can be polymer-bonded, selected from the group comprising palladium(II)acetate, tris(dibenzylidenacetone)dipalladium, palladium(0)bis(dibenzylidenacetone), tetrakis(triphenylphosphine)palladium(0), (1,1'-bis(diphenylphosphino)-ferrocene)dichloropalladium(II), bis(acetonitrile)dichloropalladium(I), palladium(II)chloride, dichlorobis(triphenyl-phosphine)palladium(II), dichloro(tricyclohexylphosphine)palladium(II), bis(acetato)bis(triphenylphosphine)-palladium(II), bistriphenylphosphinepalladium(II) dichloride, bistriphenylphosphine-palladium(II)acetate and iron(III)chloride, particularly preferably in the presence of tetrakis(triphenylphosphine)-palladium(0), and purifies where applicable and/or isolates where applicable the compound obtained in this manner of the general formula I in which at least one of residues $R^1$ to $R^4$ stands for an unsubstituted or at least monosubstituted aryl or heteroaryl residue.

Compounds of the general formula I, whereby at least one of residues $R^1$, $R^2$, $R^3$ and $R^4$ stands for an aryl or heteroaryl residue which is substituted with at least one residue selected from the group comprising —C(═O)—H and —C(═O)—($C_{1-5}$-alkyl), can be transported with at least one compound of the general formula $H_2N$(cyclopropyl) preferably in at least one reaction medium selected from the group comprising tetrahydrofuran, dioxane, dichloromethane, methanol and ethanol or corresponding mixtures, in the presence of at least one reducing agent which can be polymer-bonded, preferably in the presence of at least one reducing agent which can be polymer-bonded, selected from the group comprising sodium triacetoxyborane hydride, sodium cyanoborane hydride and sodium diacetoxyborane hydride, or in the presence of at least one catalyst, preferably in the presence of palladium on coal or in the presence of a rhodium catalyst, under a hydrogen atmosphere, preferably at a temperature of −100° C. to 200° C., into at least one corresponding compound of the general formula I, whereby at least one of residues $R^1$, $R^2$, $R^3$ and $R^4$ stands for an aryl or heteroaryl residue which is substituted with at least one residue selected from the group comprising —CH($C_{1-5}$-alkyl)-NH-(Cyclopropyl) and —CH$_2$—NH-cyclopropyl, and these are purified and/or isolated where applicable.

Compounds of the general formula I, whereby at least one of residues $R^1$, $R^2$, $R^3$ and $R^4$ stands for an aryl or heteroaryl residue which is substituted with at least one residue selected from the group comprising —CH($C_{1-5}$-alkyl)-NH-(cyclopropyl) and —CH$_2$—NH-cyclopropyl, can be transported with at least one compound of the general formula Z-S(═O)$_2$—$C_{1-5}$-alkyl, wherein Z stands for a leaving group, preferably for a halogen residue, particularly preferably for a chlorine atom, where applicable in at least one reaction medium, preferably in at least one reaction medium selected from the group comprising tetrahydrofuran, dioxane, dichloromethane, diethylether, toluene, acetonitrile and dimethylformamide, or corresponding mixtures, where applicable in the presence of at least one base, preferably in the presence of at least one base selected from the group comprising triethylamine, pyridine, diisopropylethylamine, dimethylaminopyridine, N-methyl-morpholine and diisopropylamine, preferably at a temperature of −70° C. to 200° C., into at least one compound of the general formula I, whereby at least one of residues $R^1$, $R^2$, $R^3$ and $R^4$ stands for an aryl or heteroaryl residue which is substituted with at least one residue selected from the group comprising —CH($C_{1-5}$-alkyl)-N(cyclopropyl)-S(═O)$_2$—

$C_{1-5}$-alkyl and —$CH_2$—N(cyclopropyl)-S(=O)$_2$—$C_{1-5}$-alkyl, and these are purified where applicable and/or isolated where applicable.

Compounds of the general formula I, whereby at least one of residues $R^1$, $R^2$, $R^3$ and $R^4$ stands for an aryl or heteroaryl residue which is substituted with at least one residue selected from the group comprising —CH($C_{1-5}$-alkyl)-NH-(cyclopropyl) and —$CH_2$—NH-cyclopropyl, can be transported with at least one compound of the general formula Z-C(=O)—$C_{1-5}$-alkyl or Z-C(=O)-phenyl, wherein Z stands for a leaving group, preferably for a halogen residue, particularly preferably for a chlorine atom, where applicable in at least one reaction medium, preferably in at least one reaction medium selected from the group comprising tetrahydrofuran, dioxane, dichloromethane, diethylether, toluene, acetonitrile and dimethylformamide, or corresponding mixtures, where applicable in the presence of at least one base, preferably in the presence of at least one base selected from the group comprising triethylamine, pyridine, diisopropylethylamine, dimethylaminopyridine, N-methyl-morpholine and diisopropylamine, preferably at a temperature of −70° C. to 200° C., into at least one compound of the general formula I, whereby at least one of residues $R^1$, $R^2$, $R^3$ and $R^4$ stands for an aryl or heteroaryl residue which is substituted with at least one residue selected from the group comprising —CH($C_{1-5}$-alkyl)-N(cyclopropyl)-C(=O)—$C_{1-5}$-alkyl, —CH($C_{1-5}$-alkyl)-N(cyclopropyl)-C(=O)-phenyl, —$CH_2$—N(cyclopropyl)-C(=O)—$C_{1-5}$-alkyl and —$CH_2$—N(cyclopropyl)-C(=O)-phenyl, and these are purified and/or isolated where applicable.

Compounds of the general formula I, whereby at least one of residues $R^1$, $R^2$, $R^3$ and $R^4$ stands for an aryl or heteroaryl residue which is substituted with at least one —C(=O)—O—$C_{1-5}$-alkyl residue, can be transformed in a reaction medium, preferably in a reaction medium selected from the group comprising methanol, ethanol, water, isopropanol and corresponding mixtures, in the presence of at least one base, preferably in the presence of lithium hydroxide monohydrate, at temperatures between 0° C. and 50° C. into compounds of the general formula I, whereby at least one of residues $R^1$, $R^2$, $R^3$ and $R^4$ stands for an aryl or heteroaryl residue which is substituted with at least one —C(=O)—OH residue.

The chemicals and reaction components used in the transformations described above are commercially available and can respectively be produced according to conventional methods known to the person skilled in the art.

The transformations described above can furthermore be carried out under conventional conditions familiar to the person skilled in the art, for example, in terms of pressure, temperature, protective gas atmosphere or sequence of the addition of the components. Where applicable, the optimum procedure under the respective conditions can be determined by the person skilled in the art by means of simple preliminary tests.

The intermediate and final products obtained according to the transformations described above can respectively, if desired and/or required, be purified and/or isolated according to conventional methods known to the person skilled in the art. Suitable purification methods include, for example, extraction methods and chromatographic methods such as column chromatography or preparative chromatography.

All the procedural steps described above as well as respectively the purification and/or isolation of intermediate or final products can be partially or entirely carried out under an inert gas atmosphere, preferably under a nitrogen atmosphere or argon atmosphere.

The substituted benzo[d]isoxazol-3-yl-amine compounds according to the invention can be isolated in the form of their free bases, their free acids and also respectively in the form of corresponding salts, in particular physiologically compatible salts.

The free bases of the respective substituted benzo[d]isoxazol-3-yl-amine compounds according to the invention can, for example, be transported by transformation with an inorganic or organic acid, preferably with hydrochloric acid, hydrobromic acid, sulphuric acid, phosphoric acid, methanesulphonic acid, para-toluenesulphonic acid, carbonic acid, formic acid, acetic acid, oxalic acid, succinic acid, tartaric acid, mandelic acid, fumaric acid, lactic acid, citric acid, glutamic acid or asparaginic acid, into the corresponding salts, preferably physiologically compatible salts.

The free bases of the respective substituted benzo[d]isoxazol-3-yl-amine compounds according to the invention can also be transported with the free acid or a salt of a sugar substitute such as e.g. saccharin, cyclamate or acesulfam, into the corresponding physiologically compatible salts.

The free acids of the substituted benzo[d]isoxazol-3-yl-amine compounds according to the invention can correspondingly be transported by transformation with a suitable base into the corresponding physiologically compatible salts. Examples include the alkali metal salts, alkaline earth metal salts or ammonium salts $[NH_xR_{4-x}]^+$, wherein x=0, 1, 2, 3 or 4 and R stands for a linear or branched $C_{1-4}$-alkyl residue.

The substituted benzo[d]isoxazol-3-yl-amine compounds according to the invention can where applicable, just like the corresponding acids, the corresponding bases or salts of these compounds, also be obtained by conventional methods known to the person skilled in the art in the form of their solvates, preferably in the form of their hydrates.

Insofar as the substituted benzo[d]isoxazol-3-yl-amine compounds according to the invention are obtained after their manufacture in the form of a mixture of their stereoisomers, preferably in the form of their racemates or other mixtures of their various enantiomers and/or diastereomers, these can be separated and isolated where applicable according to conventional methods known to the person skilled in the art. Examples include chromatographic separating methods, in particular liquid chromatography methods under normal pressure or under increased pressure, preferably MPLC and HPLC methods, as well as methods of fractionated crystallisation. Thereby, in particular individual enantiomers, e.g. diastereomeric salts formed by means of HPLC in a chiral stationary phase or by means of crystallisation with chiral acids, such as (+)-tartaric acid, (−)-tartaric acid or (+)-10-camphorsulphonic acid, can be separated from one another.

The substituted benzo[d]isoxazol-3-yl-amine compounds according to the invention and respectively the corresponding acids, bases, salts and solvates are toxicologically safe and are therefore suitable as medicament active ingredients in medicaments.

A further subject matter of the present invention is therefore a medicament containing at least one substituted benzo[d]isoxazol-3-yl-amine compound according to the invention and defined above including compounds;
wherein one of residues $R^5$ and $R^6$ stands for a residue selected from the group comprising linear or branched, saturated or unsaturated, unsubstituted or at least monosubstituted aliphatic residues and hydrogen and the other of residues $R^5$ and $R^6$ stands for a linear or branched, saturated or unsaturated, unsubstituted or at least monosubstituted aliphatic residue and the other residues have the meaning indicated above; as well as where applicable one or more pharmaceutically compatible excipients.

A medicament containing at least one substituted benzo[d]isoxazol-3-yl-amine compound according to the invention of the general formula I-A, I-B, I-C and I-D is particularly preferred,

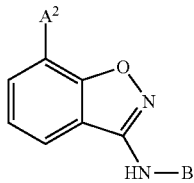

I-A

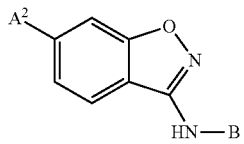

I-B

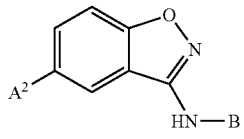

I-C

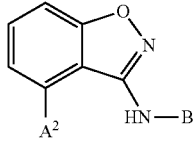

I-D wherein respectively
$A^2$ stands for a (hetero)aryl residue which is selected from the group comprising phenyl, 1-naphthyl, 2-naphthyl, thiophenyl (thienyl), furanyl and pyridinyl and which can be substituted, where applicable, with 1, 2, 3, 4 or 5 substituents independently of one another selected from the group comprising F; Cl; Br; —$CF_3$; —$OCF_3$; —$SCF_3$; —$SF_5$; —CN; —OH; methyl; ethyl; n-propyl; isopropyl; n-butyl; isobutyl; sec-butyl; tert-butyl; methoxy; ethoxy; —$NH_2$; —$N(CH_3)_2$; —$N(C_2H_5)_2$; phenyl; phenoxy, benzyl; thiophenyl (thienyl), furanyl, pyridinyl, C(=O)—H, —C(=O)—$CH_3$, —C(=O)—$C_2H_5$, —C(=O)—CH($CH_3$)$_2$, —C(=O)—C($CH_3$)$_3$, —C(=O)—O—$CH_3$, —C(=O)—O—$C_2H_5$, —C(=O)—O—C($CH_3$)$_3$, —C(=O)—O—CH($CH_3$)$_2$, —C(=O)—OH, —C(=O)—N(cyclopropyl)-$CH_3$, —C(=O)—N(cyclopropyl)-$C_2H_5$, —C(=O)—N(cyclopropyl)-CH($CH_3$)$_2$, —C(=O)—N(cyclopropyl)-C($CH_3$)$_3$, —$CH_2$—NH-cyclopropyl, —$CH_2$—N(cyclopropyl)-S(=O)$_2$—$CH_3$, —$CH_2$—N(cyclopropyl)-S(=O)$_2$—$C_2H_5$, —$CH_2$—N(cyclopropyl)-C(=O)—$CH_3$, —$CH_2$—N(cyclopropyl)-C(=O)—$C_2H_5$, —$CH_2$—N(cyclopropyl)-C(=O)—CH($CH_3$)$_2$, —$CH_2$—N(cyclopropyl)-C(=O)—C($CH_3$)$_3$ and —$CH_2$—N(cyclopropyl)-C(=O)-phenyl;
B stands for an alkyl residue selected from the group comprising methyl; ethyl; n-propyl; isopropyl; n-butyl; isobutyl; sec-butyl, tert-butyl, n-pentyl and neopentyl; for —C(=O)-phenyl; —(CH$_2$)-phenyl; —(CH$_2$)$_2$-phenyl; —(CH$_2$)$_3$-phenyl; —(CH$_2$)-pyridinyl; —(CH$_2$)$_2$-pyridinyl or —(CH$_2$)$_3$-pyridinyl; whereby the above-mentioned phenyl and pyridinyl residues can be substituted where applicable with 1, 2, 3, 4 or 5 substituents independently of one another selected from the group comprising F; Cl; Br; —$CF_3$; —$OCF_3$; —$SCF_3$; —$SF_5$; —CN; —OH; methyl; ethyl; n-propyl; isopropyl; n-butyl; isobutyl; sec-butyl; tert-butyl; methoxy; ethoxy; —$NH_2$; —$N(CH_3)_2$; —$N(C_2H_5)_2$; phenyl; phenoxy, benzyl; thiophenyl (thienyl), furanyl and pyridinyl,
respectively where applicable in the form of corresponding salts, in particular hydrochloride addition salts, or respectively in the form of corresponding solvates.

A medicament containing at least one substituted benzo[d]isoxazol-3-yl-amine compound according to the invention of the general formula I-A, I-B, I-C and I-D is very particularly preferred, wherein respectively $A^2$ stands for one of following residues $A^{21}$ or $A^{22}$:

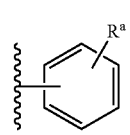

$A^{21}$

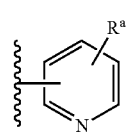

$A^{22}$ wherein
$R^a$ respectively stands for a residue which is selected from the group comprising H, F, Cl, Br, I, —CN; —$CF_3$, —$OCF_3$, —$SCF_3$, —$SF_5$, —OH, —SH, methyl; ethyl; n-propyl; isopropyl; n-butyl; isobutyl; sec-butyl; tert-butyl; —$OCH_3$; —$OC_2H_5$; —S—$CH_3$, —S—$C_2H_5$, —C(=O)—H, —C(=O)—O—$C_2H_5$, —C(=O)—OH, —$CH_2$—NH-cyclopropyl, —$CH_2$—N(cyclopropyl)-S(=O)$_2$—$CH_3$, —$CH_2$—N(cyclopropyl)-C(=O)—$CH_3$ and —$CH_2$—N(cyclopropyl)-C(=O)-phenyl and
B stands for an Alkyl residue selected from the group comprising methyl, ethyl, n-propyl, isopropyl, n-butyl, isobutyl, sec-butyl, tert-butyl, n-pentyl and neopentyl;
or stands for one of following residues $B^1$, $B^2$ or $B^3$,

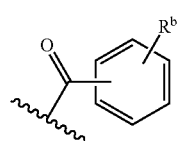

$B^1$

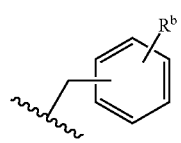

$B^2$

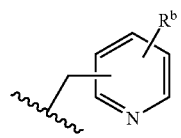

$B^3$ wherein
$R^b$ respectively stands for a residue which is selected from the group comprising H, F, Cl, Br, I, —CN; —$CF_3$, —$OCF_3$, —$SCF_3$, —$SF_5$, —OH, —SH, methyl; ethyl; n-propyl; isopropyl; n-butyl; isobutyl; sec-butyl; tert-butyl; —$OCH_3$; —$OC_2H_5$; —S—$CH_3$ and —S—$C_2H_5$.

A medicament is most preferred containing at least one compound according to the invention as defined above and/or at least one compound selected from the group comprising

[35] 2-(3-(neopentylamino)benzo[d]isoxazol-5-yl)benzoic acid,
[36] Ethyl 4-(3-(neopentylamino)benzo[d]isoxazol-5-yl)benzoate,
[37] N-neopentyl-5-(3-(trifluoromethyl)phenyl)benzo[d]isoxazol-3-amine,
[38] 3-(3-(neopentylamino)benzo[d]isoxazol-5-yl)benzonitrile,
[39] N-methyl-3-(3-(neopentylamino)benzo[d]isoxazol-5-yl)benzamide,
[40] 3-(3-(neopentylamino)benzo[d]isoxazol-5-yl)benzoic acid,
[41] Ethyl 3-(3-(neopentylamino)benzo[d]isoxazol-5-yl)benzoate,
[42] N-cyclopropyl-N-(2-methoxy-5-(3-(neopentylamino)benzo[d]isoxazol-5-yl)benzyl)methanesulphonamide,
[43] N-cyclopropyl-N-(2-methoxy-5-(3-(neopentylamino)benzo[d]isoxazol-5-yl)benzyl)acetamide,
[44] N-cyclopropyl-N-(2-fluoro-5-(3-(neopentylamino)benzo[d]isoxazol-5-yl)benzyl)acetamide,
[45] 5-(3-((cyclopropylamino)methyl)-4-methoxyphenyl)-N-neopentylbenzo[d]isoxazol-3-amine,
[46] 5-(3-((cyclopropylamino)methyl)-4-fluorophenyl)-N-neopentylbenzo[d]isoxazol-3-amine,
[47] 2-methoxy-5-(3-(neopentylamino)benzo[d]isoxazol-5-yl)benzaldehyde,
[48] 2-fluoro-5-(3-(neopentylamino)benzo[d]isoxazol-5-yl)benzaldehyde,
[49] N-cyclopropyl-N-(3-(3-(neopentylamino)benzo[d]isoxazol-5-yl)benzyl)benzamide,
[50] N-cyclopropyl-N-(3-(3-(neopentylamino)benzo[d]isoxazol-5-yl)benzyl)acetamide,
[51] 5-(3-((cyclopropylamino)methyl)phenyl)-N-neopentylbenzo[d]isoxazol-3-amine and
[52] 3-(3-(neopentylamino)benzo[d]isoxazol-5-yl)benzaldehyde;

and respectively their corresponding salts, in particular their hydrochloride addition salts, and where applicable respectively their corresponding solvates.

These medicaments according to the invention are particularly suitable for vanilloid receptor 1 (VR1/TRPV1) regulation, preferably for vanilloid receptor 1 (VR1/TRPV1) inhibition and/or for vanilloid receptor 1 (VR1/TRPV1) stimulation.

The medicaments according to the invention are also preferably suitable for the prophylaxis and/or treatment of disorders or illnesses which are at least partially mediated by vanilloid receptors 1.

The medicament according to the invention is preferably suitable for the treatment and/or prophylaxis of one or more illnesses selected from the group comprising pain, preferably pain selected from the group comprising acute pain, chronic pain, neuropathic pain and visceral pain; joint pain; migraines; depression; nervous complaints; nerve injuries; neurodegenerative illnesses, preferably selected from the group comprising multiple sclerosis, Alzheimer's disease, Parkinson's disease and Huntington's disease; cognitive dysfunctions, preferably cognitive deficiencies, particularly preferably memory disorders; epilepsy; airway illnesses, preferably selected from the group comprising asthma and lung inflammation; coughs; urinary incontinence; overactive bladder; stomach ulcers; irritable bowel syndrome; strokes; eye irritation; skin irritation; neurotic skin complaints; inflammatory illnesses, preferably inflammation of the bowel; diarrhoea; pruritus; eating disorders, preferably selected from the group comprising bulimia, cachexia, anorexia and obesity; medicament dependency; medicament abuse; withdrawal symptoms in the case of medicament dependency; development of tolerance to medicaments, preferably to natural or synthetic opioids; drug dependency; drug abuse; withdrawal symptoms in the case of drug dependency; alcohol dependency; alcohol abuse and withdrawal symptoms in the case of alcohol dependency; for diuresis; for antinatriuresis; to influence the cardiovascular system; to improve vigilance; to increase libido; to modulate movement activity; for anxiolysis; for local anaesthesia and/or to inhibit undesired side effects, preferably selected from the group comprising hyperthermia, high blood pressure and narrowing of the bronchia, triggered by the administration of vanilloid receptor 1 (VR1/TRPV1 receptor) agonists, preferably selected from the group comprising capsaicin, resiniferatoxin, olvanil, arvanil, SDZ-249665, SDZ-249482, nuvanil and capsavanil.

The medicament according to the invention is particularly preferably suitable for the treatment and/or prophylaxis of one or more illnesses selected from the group comprising pain, preferably pain selected from the group comprising acute pain, chronic pain, neuropathic pain and visceral pain; migraines; depression; neurodegenerative illnesses, preferably selected from the group comprising multiple sclerosis, Alzheimer's disease, Parkinson's disease and Huntington's disease; cognitive dysfunctions, preferably cognitive deficiencies, particularly preferably memory disorders; urinary incontinence; overactive bladder; medicament dependency; medicament abuse; withdrawal symptoms in the case of medicament dependency; development of tolerance to medicaments, preferably development of tolerance to natural or synthetic opioids; drug dependency; drug abuse; withdrawal symptoms in the case of drug dependency; alcohol dependency; alcohol abuse and withdrawal symptoms in the case of alcohol dependency.

The medicament according to the invention is very particularly preferably suitable for the treatment and/or prophylaxis of pain, preferably pain selected from the group comprising acute pain, chronic pain, neuropathic pain and visceral pain, and/or urinary incontinence.

A further subject matter of the present invention is the use of at least one substituted benzo[d]isoxazol-3-yl-amine compound according to the invention and where applicable one or more pharmaceutically compatible excipients to produce a medicament for vanilloid receptor 1 (VR1/TRPV1) regulation, preferably for vanilloid receptor 1 (VR1/TRPV1) inhibition and/or for vanilloid receptor 1 (VR1/TRPV1) stimulation.

The use is preferred of at least one substituted benzo[d]isoxazol-3-yl-amine compound according to the invention and where applicable one or more pharmaceutically compatible excipients to produce a medicament for the prophylaxis and/or treatment of disorders or illnesses which are at least partially mediated by vanilloid receptors 1.

The use is particularly preferred of at least one substituted benzo[d]isoxazol-3-yl-amine compound according to the invention and where applicable one or more pharmaceutically compatible excipients to produce a medicament for the treatment and/or prophylaxis of one or more illnesses selected from the group comprising pain, preferably of pain selected from the group comprising acute pain, chronic pain, neuropathic pain and visceral pain; joint pain; migraines; depression; nervous complaints; nerve injuries; neurodegenerative illnesses, preferably selected from the group comprising multiple sclerosis, Alzheimer's disease, Parkinson's disease and Huntington's disease; cognitive dysfunctions, preferably cognitive deficiencies, particularly preferably memory disorders; epilepsy; airway illnesses, preferably selected from the group comprising asthma and lung inflammation; coughs; urinary incontinence; overactive bladder; stomach ulcers; irritable bowel syndrome; strokes; eye irritation; skin irritation; neurotic skin complaints; inflammatory illnesses, preferably inflammation of the bowel; diarrhoea; pruritus; eating disorders, preferably selected from the group comprising bulimia, cachexia, anorexia and obesity; medicament dependency; medicament abuse; withdrawal symptoms in the case of medicament dependency; development of tolerance to medicaments, preferably to natural or synthetic opioids; drug dependency; drug abuse; withdrawal symptoms in the case of drug dependency; alcohol dependency; alcohol abuse and withdrawal symptoms in the case of alcohol dependency; for diuresis; for antinatriuresis; to influence the cardiovascular system; to improve vigilance; to increase libido; to modulate movement activity; for anxiolysis; for local anaesthesia and/or to inhibit undesired side effects, preferably selected from the group comprising hyperthermia, high blood pressure and narrowing of the bronchia, triggered by the administration of vanilloid receptor 1 (VR1/TRPV1 receptor) agonists, preferably selected from the group comprising capsaicin, resiniferatoxin, olvanil, arvanil, SDZ-249665, SDZ-249482, nuvanil and capsavanil.

The use is very particularly preferred of at least one substituted benzo[d]isoxazol-3-yl-amine compound according to the invention and where applicable one or more pharmaceutically compatible excipients to produce a medicament for the treatment and/or prophylaxis of one or more illnesses selected from the group comprising pain, preferably pain selected from the group comprising acute pain, chronic pain, neuropathic pain and visceral pain; migraines; depression; neurodegenerative illnesses, preferably selected from the group comprising multiple sclerosis, Alzheimer's disease, Parkinson's disease and Huntington's disease; cognitive dysfunctions, preferably cognitive deficiencies, particularly preferably memory disorders; urinary incontinence; overactive bladder; medicament dependency; medicament abuse; withdrawal symptoms in the case of medicament dependency; development of tolerance to medicaments, preferably development of tolerance to natural or synthetic opioids; drug dependency; drug abuse; withdrawal symptoms in the case of drug dependency; alcohol dependency; alcohol abuse and withdrawal symptoms in the case of alcohol dependency.

The use is even more preferable of at least one substituted benzo[d]isoxazol-3-yl-amine compound according to the invention and where applicable one or more pharmaceutically compatible excipients to produce a medicament for the treatment and/or prophylaxis of pain, preferably selected from the group comprising acute pain, chronic pain, neuropathic pain and visceral pain, and/or urinary incontinence.

The medicament according to the invention is suitable for administration to adults and children including infants.

The medicament according to the invention can be present as a liquid, semi-solid or solid form of medication, for example, in the form of injection solutions, drops, juices, syrups, sprays, suspensions, tablets, patches, capsules, plasters, suppositories, cremes, lotions, gels, emulsions, aerosols or in multiparticular form, for example, in the form of pellets or granulates, where applicable pressed into tablets, filled into capsules or suspended in a liquid, and also administered as such. As well as at least one substituted benzo[d]isoxazol-3-yl-amine compound according to the invention, the medicament according to the invention normally contains further physiologically compatible medicament excipients which can preferably be selected from the group comprising support mediums, fillers, solvents, diluting agents, surfactants, dyes, preservatives, blasting agents, lubricants, flavourings and binding agents.

The selection of the physiologically compatible excipients and the quantities to be used thereof depends on whether the medicament is supposed to be applied orally, subcutaneously, parenterally, intravenously, intraperitoneally, intradermally, intramuscularly, intranasally, buccally, rectally or locally, for example, on infections on the skin, the mucous membranes and on the eyes. Preparations in the form of tablets, dragees, capsules, granulates, pellets, drops, juices and syrups are preferably suitable for oral application, while solutions, suspensions, easily reconstitutable dry preparations and sprays are preferably suitable for parenteral, topical and inhalative application.

The substituted benzo[d]isoxazol-3-yl-amine compounds according to the invention used in the medicament according to the invention can be present in a depot, in a dissolved form or a plaster, possibly with the addition of agents which promote skin penetration, as suitable percutaneous application preparations.

Preparation forms which can be applied orally or percutaneously can also release the substituted benzo[d]isoxazol-3-yl-amine compound according to the invention in a delayed manner.

The production of the medicaments according to the invention is performed with the help of conventional means, devices, methods and processes known from the prior art, as described, for example, in "Remingtons Medicament Sciences", publisher A. R. Gennaro, $17^{th}$ edition, Mack Publishing Company, Easton, Pa., 1985, in particular in Part 8, Chapters 76 to 93. The corresponding description is hereby introduced as a reference and is to be regarded as part of the disclosure.

The quantity of the respective substituted benzo[d]isoxazol-3-yl-amine compound according to the invention to be administered to patients can vary and is for example dependent on the weight or age of the patient and on the type of application, the indication and the severity of the illness. Normally 0.005 to 100 mg/kg, preferably 0.05 to 75 mg/kg body weight of the patient at least of such a compound according to the invention is applied.

Pharmacological Methods:

I. Functional Study on Vanilloid Receptor 1 (VR1/TRPV1 Receptor)

The agonistic or antagonistic effect of the substances to be studied on vanilloid receptor 1 (VR1/TRPV1) of the rat species can be determined with the following assay. According to this assay, the $Ca^{2+}$ inflow through the receptor canal is quantified with the help of a $Ca^{2+}$-sensitive dye (type Fluo-4, Molecular Probes Europe BV, Leiden Netherlands) in the Fluorescent Imaging Plate Reader (FLIPR, Molecular Devices, Sunnyvale, USA).

Method:

Complete medium: 50 mL HAMS F12 Nutrient Mixture (Gibco Invitrogen GmbH, Karlsruhe, Germany) with
10% by vol. FCS (fetal calf serum, Gibco Invitrogen GmbH, Karlsruhe, Germany, heat-inactivated);
2 mM L-glutamine (Sigma, Munich, Germany);
1% by weight AA solution (antibiotic/antimycotic solution, PAA, Pasching, Austria) and 25 ng/ml medium NGF (2.5 S, Gibco Invitrogen GmbH, Karlsruhe, Germany)
Cell culture plate: Poly-D-Lysin-coated, 96 well black/clear plates (BD Biosciences, Heidelberg, Germany) are additionally coated with laminin (Gibco Invitrogen GmbH, Karlsruhe, Germany) by diluting laminin to a concentration of 100 pg/mL with PBS (Ca—Mg-free PBS, Gibco Invitrogen GmbH, Karlsruhe, Germany). Aliquots with a concentration of 100 µg/mL of laminin are removed and stored at −20° C. The aliquots are diluted with PBS in a ratio of 1:10 to 10 µg/mL of laminin and respectively 50 µL of the solution is pipetted into a recess of the cell culture plate. Die cell culture plates are incubated for at least two hours at 37° C., the remaining solutions is filtered off by suction and the recesses are each washed twice with PBS. The coated cell culture plates are stored with the remaining PBS and this is only removed directly before the addition of the cells.

Preparation of the Cells:

The spinal column is removed from decapitated rats and this is placed directly in a cold HBSS buffer (Hank's buffered saline solution, Gibco Invitrogen GmbH, Karlsruhe, Germany), located in an ice bath, to which is added 1% by vol. (percent by volume) of an AA solution (antibiotic/antimycotic solution, PM, Pasching, Austria). The spinal column is divided longitudinally and removed from the vertebral canal together with fascia. The dorsal root ganglia (DRGs) are subsequently removed and in turn stored in cold HBSS buffer to which is added 1% by vol. of an AA solution. The DRGs which have been made completely free of blood residues and spinal nerves are transported in each case into 500 µL cold collagenase type 2 (PAA, Pasching, Austria) and incubated for 35 minutes at 37° C. After the addition of 2.5% by vol. of trypsin (PAA, Pasching, Austria), incubation is performed for a further 10 minutes at 37° C. Once incubation has been completed, the enzyme solution is carefully pipetted off and 500 µL complete medium is added to each of the DRGs.

The DRGs are each multiply suspended, drawn by means of a syringe through cannulas no. 1, no. 12 and no. 16 and transferred into 50 mL Falcon tubes and this is filled with complete medium to 15 mL. The content of each Falcon tube is respectively filtered by a 70 µm Falcon filter insert and centrifuged for 10 minutes in at 1200 rotations and room temperature. The resultant pellet is respectively received in 250 µL complete medium and the cell number determined.

The number of cells in the suspension is set at 3 times $10^5$ per mL and in each case 150 µL of this suspension is put into a recess of the coated cell culture plates as described above. The plates are left to stand in the incubator for two to three days at 37° C., 5% by vol. $CO_2$ and 95% relative air humidity.

The cells are subsequently loaded with 2 µM fluo-4 and 0.01% by vol. Pluronic F127 (Molecular Probes Europe BV, Leiden Netherlands) in HBSS buffer (Hank's buffered saline solution, Gibco Invitrogen GmbH, Karlsruhe, Germany) for 30 min at 37° C., washed 3× with HBSS buffer and used after a further incubation of 15 minutes at room temperature for $Ca^{2+}$ measurement in the FLIPR assay. The $Ca^{2+}$-dependent fluorescence is thereby measured before and after addition of substances ($\lambda_{ex}$=488 nm, $\lambda_{em}$=540 nm). Quantification is carried out by measuring the maximum fluorescence intensity (FC, Fluorescence Counts) over time.

FLIPR Assay:

The FLIPR protocol comprises 2 substance additions. The compounds to be tested (10 µM) are first pipetted onto the cells and the $Ca^{2+}$ inflow compared with the control (capsaicin 10 µM). This results in the indication in % activation in relation to the $Ca^{2+}$ signal after addition of 10 µM capsaicin (CP). After 5 minutes of incubation, 100 nM capsaicin is applied and the inflow of $Ca^{2+}$ is once again determined.

Desensitising agonists and antagonists lead to a suppression of the $Ca^{2+}$ inflow. % inhibition is calculated in comparison to the maximum achievable inhibition with 10 µM capsaicin.

Triple determinations (n=3) are performed and repeated in at least 3 independent experiments (N=4).

On the basis of the percentage suppression by various concentrations of the compounds to be tested of the general formula I, $IC_{50}$ inhibition concentrations are calculated which bring about a 50 percent suppression of the capsaicin.

II. Functional Studies on the Vanilloid Receptor (VR1)

The agonistic and/or antagonistic effect of the substances to be tested on the vanilloid receptor (VR1) can also be determined with the assay. According to this assay, the $Ca^{2+}$ inflow through the canal is quantified with the help of a $Ca^{2+}$-sensitive dye (type fluo-4, Molecular Probes, Europe BV, Leiden, Netherlands) in the Fluorescent Imaging Plate Reader (FLIPR, Molecular Devices, Sunnyvale, USA).

Method:

Chinese Hamster Ovary cells (CHO K1 cells, European Collection of Cell Cultures (ECACC) Great Britain) are transfected in a stable manner with the VR1 gene. For functional studies, these cells are plated on Poly-D-Lysin-coated, 96 well black/clear plates (BD Biosciences, Heidelberg, Germany) in a density of 25,000 cells/well. The cells are incubated overnight at 37° C. and 5% $CO_2$ in a culture medium (Nutrient Mixture Ham's F12, 10% by vol. FCS (Fetal calf serum), 18 pg/ml L-Proline). On the following day, the cells are incubated with fluo-4 (fluo-4 2 µM, Pluronic F127 0.01% by vol., Molecular Probes in HBSS (Hank's buffered saline solution), Gibco Invitrogen GmbH, Karlsruhe, Germany) for 30 minutes at 37° C. The plates are subsequently washed 3 times with HBSS buffer and used after a further incubation of 15 minutes at room temperature for $Ca^{2+}$-measurement in the FLIPR. The $Ca^{2+}$-dependent fluorescence is thereby measured before and after addition of the substances to be measured (wavelength $\lambda_{ex}$=488 nm, $\lambda_{em}$=540 nm). Quantification is performed by measuring the maximum fluorescence intensity (FC, Fluorescence Counts) over time.

FLIPR Assay:

The FLIPR protocol comprises 2 substance additions. The substances to be tested (10 µM) are first pipetted onto the cells and the $Ca^{2+}$ inflow compared with the control (capsaicin 10 µM) (% activation in relation to the $Ca^{2+}$-signal after addition of 10 µM capsaicin). After 5 minutes of incubation, 100 nM capsaicin is applied and the inflow of $Ca^{2+}$ is also determined.

Desensitising agonists and antagonists led to a suppression of the $Ca^{2+}$ inflow. % inhibition is calculated in comparison to the maximum achievable inhibition with 10 µM capsaicin.

III. Formalin Test in Mice

The study to determine the antinociceptive effect of the substituted benzo[d]isoxazol-3-yl-amine compounds according to the invention is carried out in the formalin test in male mice (NMRI, 20 to 30 g body weight, Iffa, Credo, Belgium).

A differentiation is made between the first (early) phase (0 to 15 minutes after the formalin injection) and the second (late) phase (15 to 60 minutes after the formalin injection) in the formalin test according to D. Dubuisson et al., Pain 1977, 4, 161-174. The early phase represents, as a direct reaction to the formalin injection, a model for acute pain, while the late phase is regarded as the model for persistent (chronic) pain (T. J. Coderre et al., Pain 1993, 52, 259-285). The corresponding literature descriptions are hereby introduced as a reference and are to be considered as a part of the disclosure.

The substituted benzo[d]isoxazol-3-yl-amine compounds according to the invention are tested in the second phase of the formalin test in order to obtain information on substance effects on chronic/inflammatory pain.

Depending on the type of application of the compounds according to the invention, the application time of the substituted benzo[d]isoxazol-3-yl-amine compounds according to the invention is selected before the formalin injection. The intravenous application of 10 mg/kg body weight of the test substances is performed 5 minutes before the formalin injection. This is performed by a single subcutaneous formalin injection (20 µL, 1% aqueous solution) into the dorsal side of the right rear paw so that, in the case of freely moving test animals, a nociceptive reaction is induced which is expressed in noticeable licking and biting of the relevant paw.

The nociceptive behaviour is subsequently continuously recorded for a study period of three minutes in the second (late) phase of the formalin test (21 to 24 minutes after the formalin injection) by observation of the animals. The quantification of the pain behaviour is performed by adding together the seconds during which the animals demonstrate licking and biting of the relevant paw in the study period.

The comparison is performed in each case with control animals which are given vehicles (0.9% aqueous sodium chloride solution) before formalin application instead of the compounds according to the invention.

Based on the quantification of the pain behaviour, the substance effect is determined in percent in the formalin test as a change against the corresponding control.

After injection of substances which have an antinociceptive effect in the formalin test, the described modes of behaviour of the animals, i.e. licking and biting, are reduced or nullified.

The invention is explained below with the help of several examples. These explanations are only examples and do not restrict the general concept of the invention.

EXAMPLES

The yields of the produced compounds are not optimised. All the temperatures are uncorrected.

| Abbreviations | |
|---|---|
| aq. | aqueous |
| APCI | atmospheric pressure chemical ionisation |
| equiv. | Amount-of-substance equivalents |
| DCM | Dichloromethane |
| DMF | Dimethylformamide |
| DMSO | Dimethylsulphoxide |
| EtOAc | Ethylacetate |
| EtOH | Ethanol |
| sat. | saturated |
| h | hours |
| min | minutes |
| NMR | Nuclear magnetic resonance spectroscopy |
| MeOH | Methanol |
| RT | Room temperature |
| THF | Tetrahydrofuran |

The chemicals and solvents used were sourced commercially from conventional suppliers (Acros, Avocado, Aldrich, Bachem, Fluka, Lancaster, Maybridge, Merck, Sigma, TCI, etc.) or synthesised according to methods known to the person skilled in the art.

Silica gel 60 (0.040-0.063 mm) from E. Merck, Darmstadt was used as the stationary phase for column chromatography.

The thin-layer chromatographic studies were performed with HPTLC precoated plates, silica gel 60 F 254, from E. Merck, Darmstadt.

The mixture ratios of solvents, mobile solvents or for chromatographic studies are always indicated in volume/volume.

Analysis was performed by mass spectroscopy and NMR. General Instruction for Producing the Benzisoxazol Matrix:

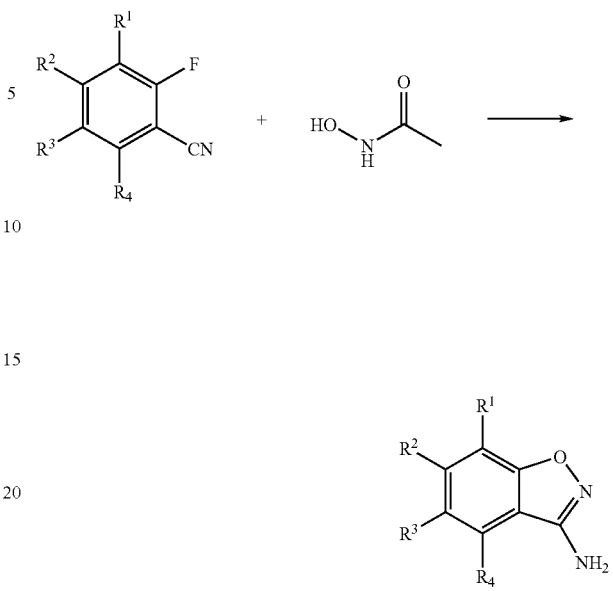

The matrix of the benzisoxazols according to the invention was produced in an analogous manner to the instruction of Palermo (M. G. Palermo, *Tetrahedron Lett.* 1996; 37; 17; 2885-2886). The corresponding description is hereby introduced as a reference and should be regarded as a part of the present disclosure. In contrast to the cited instruction, the purification of the benzoisoxazol compounds is partially performed by precipitating the corresponding HCl salt.

Implementation:

Acetohydroxamic acid (1.1 equiv.) was suspended in DMF (1.45 mL/mmol acetohydroxamic acid) in a triple-necked flask. Potassium t-butoxide (1.1 equiv.) was added under inert gas. The mixture was stirred for 30 min. at room temperature and subsequently, where applicable, substituted 2-fluoro-benzonitrile (1 equiv.) was added. The reaction batch was heated to 50° C. and stirred for 1 h at this temperature. After cooling, the reaction mixture was added to a mixture (1.8 mL/mmol acetohydroxamic acid) of equal volume ratios of saturated NaCl solution and ethyl acetate and stirred well for 30 min. The phases were separated and the aqueous phase extracted three times with ethyl acetate (in each case 0.8 mL/mmol acetohydroxamic acid).

The organic phases were combined and washed three times with saturated NaCl solution (in each case 0.8 mL/mmol acetohydroxamic acid) and subsequently dried by means of magnesium sulphate.

The magnesium sulphate was filtered off and the filtrate was first concentrated on the rotary evaporator and subsequently on the oil pump.

The obtained hydrochloride had advantageously to be precipitated in some cases for the purpose of further purification.

To this end, the residue was dissolved in methyl ethyl ketone (8.7 mL/g residue). After addition of water (0.1 mL/g residue), trimethylchlorosilane (0.7 mL/g residue) was added in drops with slow stirring and ice-water cooling.

The flask was place in the refrigerator over night, the resultant precipitate was filtered off and dried in the exsiccator with the help of phosphorous pentoxide as the drying agent.

Compounds A and B were produced according to the instruction above:

| | Benzisoxazol | Yield |
|---|---|---|
| A | 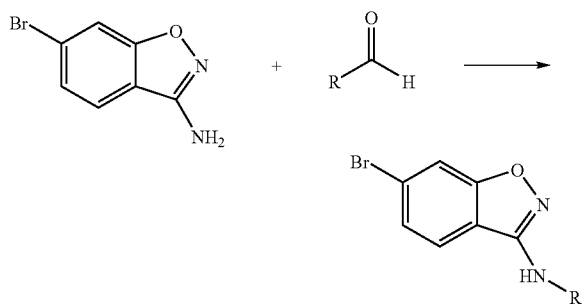 | 42% |
| B | | 42% |

H—Cl

General Instruction for Reductive Amination of the Amino-Substituted Benzisoxazol Matrix:

Implementation

The respective benzisoxazol (3.71 mmol, 1 equiv.) was dissolved in DCM (48 ml), the corresponding aldehyde (3.71 mmol, 1 equiv.) was added and stirring was performed for 1 h at room temperature. Triethylsilane (3.71 mmol, 1 equiv.) and trifluoroacetic acid (11.13 mmol, 3 equiv.) were added in drops and the mixture was heated under inert gas for 15-20 h under reflux. After cooling, the batch was adjusted to pH 8-9 with sat. NaHCO$_3$ solution and the aqueous phase extracted 4 times with DCM. The combined organic phases were dried by means of MgSO$_4$ and concentrated The obtained raw product was purified by flash chromatography (diethylether/hexane).

One thereby obtains, for example, the following preliminary stages (yield 86% and 82% respectively):

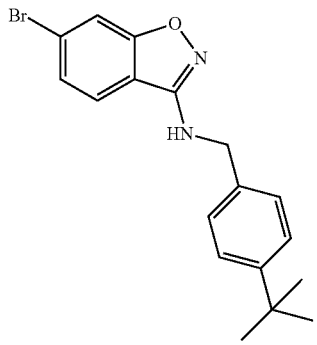

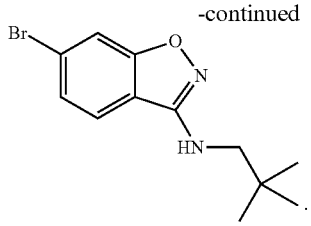

General Instruction for Acylating the Amino-Substituted Benzisoxazol Matrix:

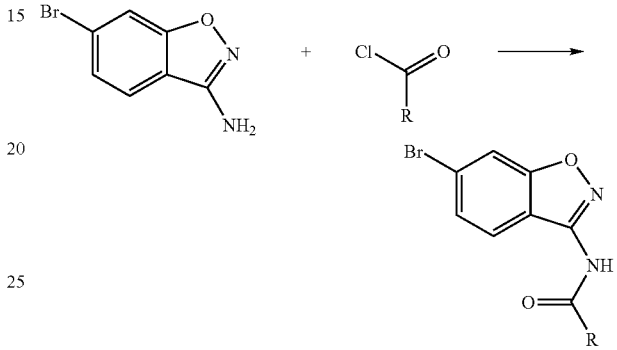

Implementation

The respective benzisoxazol (23.5 mmol) was dissolved in pyridine (28 ml) and cooled in the ice bath to 0° C. A white suspension was produced to which the respective acid chloride (47 mmol) was added in drops. Stirring was subsequently performed for 4 h at RT.

After the end of the reaction, the batch was diluted with DCM (200 ml) and extracted three times with (100 ml) 5% HCl solution (100 ml). The organic phase was washed with a little sat. NaHCO$_3$ solution and sat. NaCl, dried by means of Na$_2$SO$_4$ and concentrated.

For the purpose of purification, the raw product was boiled out with ether and the residue was filtered after cooling. The mother liquor was subsequently concentrated to approx. 20 ml and the residue also filtered.

General Instruction for Producing Aryl-Substituted Benzisoxazol Compounds:

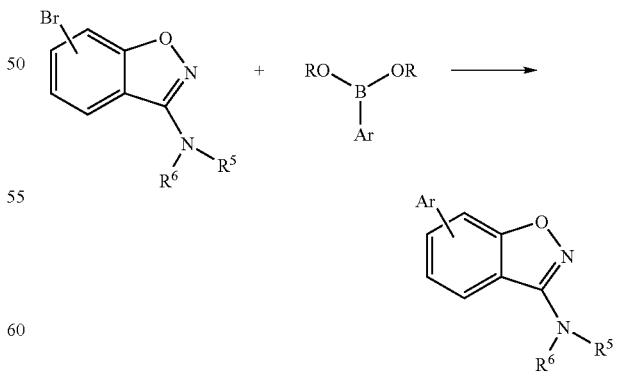

Implementation:

The respective benzisoxazol (0.96 mmol, 1 equiv.) was dissolved in a mixture of dioxane (6.5 ml), water (2.6 ml) and ethanol (1.9 ml) and the corresponding boronic acid derivative (1.34 mmol, 1.4 Equiv.) was added. Sodium carbonate (3.16 mmol, 3.3 equiv.) was then added. The mixture was placed under inert gas and tetrakis(triphenylphosphine)-palladium(0) (0.02 mmol, 0.02 equiv.) was added. Heating was subsequently performed under inert gas for 16 h under reflux. After cooling, the mixture was diluted with water and extracted three times with 20 ml toluene in each case. The combined organic phases were washed three times with in each case 15 ml KOH solution (0.5 N), dried by means of sodium sulphate and concentrated. The obtained raw product was purified by flash chromatography (ether/hexane).

According to this instruction, the following compounds were obtained:

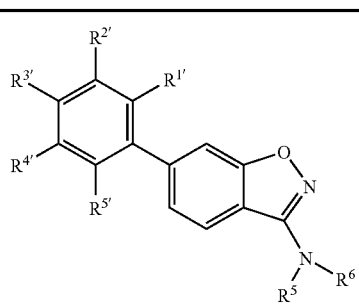

| | $R^{1'}$ | $R^{2'}$ | $R^{3'}$ | $R^{4'}$ | $R^{5'}$ | $R^5$ | $R^6$ |
|---|---|---|---|---|---|---|---|
| 1 | H | H | H | Cl | H | H | Bn |
| 2 | H | H | Cl | H | H | H | Bn |
| 3 | H | H | CH₃ | H | H | H | Bn |
| 4 | H | H | H | H | OCH₃ | H | Bn |
| 5 | H | H | H | Cl | H | H | C(=O)Ph |
| 6 | H | H | Cl | H | H | H | C(=O)Ph |
| 7 | H | H | CH₃ | H | H | H | C(=O)Ph |
| 8 | H | H | H | H | OCH₃ | H | C(=O)Ph | whereby Bn=benzyl and Ph=phenyl

Synthesis of Exemplary Compound 52

3-(3-(neopentylamino)benzo[d]isoxazol-5-yl)benzaldehyde

EtOH (15 mL) was added to a suspension of 5-bromine-N-neopentylbenzo[d]isoxazol-3-amine (1.7 g, 6.0 mmol, 1 equiv.) and 3-formylphenylboronic acid (1.1 g, 7.2 mmol, 1.2 equiv.) in toluene (50 mL), followed by aq. sodium carbonate sol. (2.5 M, 15 mL) and tetrakis(triphenylphosphine)-palladium(0) (0.066 g, 0.057 mmol, 0.01 equiv.). The reaction mixture was subsequently heated for 5 hours under reflux and concentrated after cooling to RT. The residue was absorbed in EE (150 mL) and washed with water (2×20 mL) and sat. aq. sodium chloride solution (1×20 mL), dried (MgSO₄) and the solvent removed in a vacuum. After column chromatographic purification (hexane/EE; 10:1; 5:1; 3:1), the desired product is obtained (1.18 g, 64%).

Synthesis of Exemplary Compound 35

2-(3-(neopentylamino)benzo[d]isoxazol-5-yl)benzoic acid 5-bromine-N-neopentylbenzo[d]isoxazol-3-amine (0.30 g, 1.1 mmol, 1 equiv.) and 2-methoxycarbonylphenylboronic acid (0.23 g, 1.27 mmol, 1.2 equiv.) were dissolved in DMF (9 mL). Aq. Na₂CO₃ solution (0.54 g/3.6 mL H₂O) was added and the mixture stirred for 2 min at RT. Bis(triphenylphosphine)-palladium(II)-chloride (0.041 g, 0.053 mmol, 0.05 equiv.) was subsequently added and the reaction mixture heated in the microwave (CEM Explorer) in a sealed 10 mL tube at 200 Watt for 5 min at 200° C. The reaction mixture cooled to RT was absorbed in EtOAc (100 mL) and washed with water (2×20 mL) and sat. aq. NaCl sol. (1×20 mL), dried (MgSO₄) and subsequently the solvent removed in a vacuum. After column chromatographic purification (hexane/EtOAc; 5:1), the desired product is obtained (0.1 g, 29%).

Exemplary compound 36: Ethyl 4-(3-(neopentylamino)benzo[d]isoxazol-5-yl)benzoate; 56% yield Exemplary compound 37: (N-neopentyl-5-(3-(trifluoromethyl)phenyl)benzo[d]isoxazol-3-amine; 54% yield Exemplary compound 38: (3-(3-(neopentylamino)benzo[d]isoxazol-5-yl)benzonitrile; 62% yield;

Exemplary compound 41: Ethyl 3-(3-(neopentylamino)benzo[d]isoxazol-5-yl)benzoate; 65% yield;

Exemplary compound 48: (2-fluoro-5-(3-(neopentylamino)benzo[d]isoxazol-5-yl)benzaldehyde; 54% yield and exemplary compound 47: 2-methoxy-5-(3-(neopentylamino)benzo[d]isoxazol-5-yl)benzaldehyde; 50% yield were produced in an analogous manner.

Automated Synthesis:

The Production of Aryl-Substituted Benzisoxazol Compounds was also Performed by Automated Synthesis:

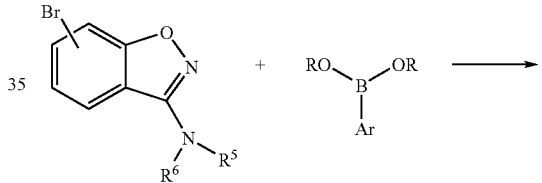

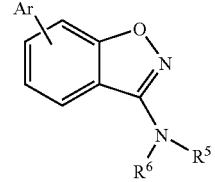

Benzisoxazol solution (2 ml, 0.05 M in dioxane), boronic acid solution (1.25 ml, 0.2 M in ethanol), sodium carbonate solution (0.3 ml, 1.2 M in water) and freshly mixed tetrakis(triphenylphosphine)-palladium(0) solution (0.3 ml, 0.04 M in dioxane) were consecutively pipetted into a dry threaded glass with a septum cap at RT. The reaction solution was heated and shaken under nitrogen and reflux in the Heidolph Synthesis 1 for 16 h at 100° C.

After the end of reaction, 2 ml of water and 3 ml of toluene were added, mixed and the phases separated. The aqueous phase was once again extracted with 3 ml toluene and the combined organic phases washed with 3 ml KOH (0.5 N). The combined organic phases were dried by means of magnesium sulphate and concentrated in the GeneVac.

According to this instruction, the following compounds were obtained:

| | R$^{1'}$ | R$^{2'}$ | R$^{3'}$ | R$^{4'}$ | R$^{5'}$ | R$^5$ | R$^6$ |
|---|---|---|---|---|---|---|---|
| 13 | H | H | Cl | H | H | H | CH$_2$-2-pyridyl |
| 14 | H | H | H | H | H | H | CH$_2$-2-pyridyl |
| 15 | H | H | H | H | CH$_3$ | H | CH$_2$-2-pyridyl |
| 16 | H | H | Cl | H | H | H | CH$_2$-3-pyridyl |
| 17 | H | H | H | H | H | H | CH$_2$-3-pyridyl |
| 18 | H | H | H | H | CH$_3$ | H | CH$_2$-3-pyridyl |
| 19 | H | H | H | H | OH | H | CH$_2$-3-pyridyl |
| 20 | H | H | Cl | H | H | H | CH$_2$-4-pyridyl |
| 21 | H | H | H | H | H | H | CH$_2$-4-pyridyl |
| 22 | H | H | H | H | CH$_3$ | H | CH$_2$-4-pyridyl |
| 23 | H | H | Cl | H | H | H | CH$_2$-(4-CN-phenyl) |
| 24 | H | H | H | H | H | H | CH$_2$-(4-CN-phenyl) |
| 25 | H | H | H | H | CH$_3$ | H | CH$_2$-(4-CN-phenyl) |
| 26 | H | H | H | H | OH | H | CH$_2$-(4-CN-phenyl) |
| 27 | H | H | Cl | H | H | H | CH$_2$-(3-CH$_3$-phenyl) |
| 28 | H | H | H | H | H | H | CH$_2$-(3-CH$_3$-phenyl) |
| 29 | H | H | H | H | CH$_3$ | H | CH$_2$-(3-CH$_3$-phenyl) |
| 30 | H | H | H | H | OH | H | CH$_2$-(3-CH$_3$-phenyl) |
| 31 | H | H | Cl | H | H | H | CH$_2$-(3-Cl-phenyl) |
| 32 | H | H | H | H | H | H | CH$_2$-(3-Cl-phenyl) |
| 33 | H | H | H | H | CH$_3$ | H | CH$_2$-(3-Cl-phenyl) |
| 34 | H | H | H | H | OH | H | CH$_2$-(3-Cl-phenyl) |

General Instruction for Producing Heteroaryl-Substituted Benzisoxazol Compounds:

R$^3$ = poss. subst. aryl; heteroaryl
X = halogen

Implementation

The respective benzisoxazol (0.695 mmol, 1 equiv.) was dissolved in THF (20 ml) and tetrakis(triphenylphosphine)-palladium(0) (0.007 mmol, 0.01 equiv.) was added under inert gas. The organozinc reagent (1.04 mmol, 1.5 equiv.; sol. in THF) was subsequently added slowly. Heating was then performed under inert gas for 2-3 h under reflux. After cooling, the mixture was diluted with water and extracted with ethyl acetate. The combined organic phases were washed with sat. NaCl solution, dried by means of magnesium sulphate and concentrated. The obtained raw product was purified by flash chromatography (diethylether/hexane).

According to this instruction, the following compounds were obtained:

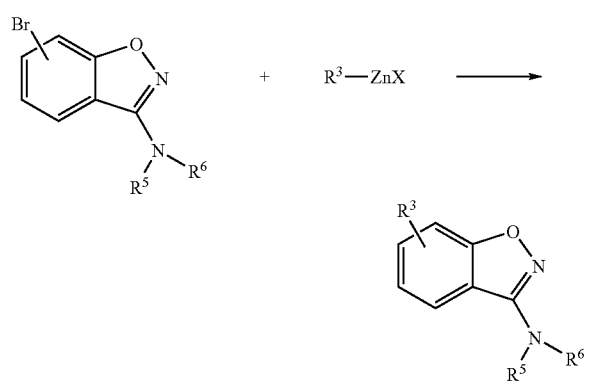

| | R | Yield |
|---|---|---|
| 9 | 2-pyridyl | 55% |
| 10 | 3-methyl-2-pyridyl | 77% |
| 11 | 6-methyl-2-pyridyl | 44% |
| 12 | phenyl | 21% |

Synthesis of Exemplary Compound 51

5-(3-((cyclopropylamino)methyl)phenyl)-N-neopentylbenzo[d]isoxazol-3-amine

Cyclopropylamine (1.04 mL, 14.92 mmol, 5 equiv.) was added to a solution of 3-(3-(neopentylamino)benzo[d]isoxazol-5-yl)benzaldehyde (exemplary compound 52) (0.92 g, 2.98 mmol, 1 equiv.) in THF (50 mL) and sodium cyanoboran hydride (3.16 g, 14.92 mmol, 5 equiv.) was subsequently added to the mixture. The suspension was stirred for 3 days at RT, subsequently hydrolysed by the addition of sat. aq. sodium hydrogen carbonate sol. (approx. 5 mL) and the solvent removed in a vacuum. The residue was absorbed in EtOAc (10 mL) and extracted with sat. aq. sodium hydrogen carbonate sol. (2×15 mL) and sat. aq. NaCl solution (1×15 mL), dried (MgSO$_4$) and the solvent removed in a vacuum. After column-chromatographic purification (EtOAc/MeOH; 20:1), the desired product (0.85 g, 82%) is obtained.

Exemplary compound 46: (5-(3-((cyclopropylamino)methyl)-4-fluorophenyl)-N-neopentylbenzo[d]isoxazol-3-amine; 36% yield and exemplary compound 45: (5-(3-((cyclopropylamino)methyl)-4-methoxyphenyl)-N-neopentylbenzo[d]isoxazol-3-amine; 85% were manufactured in an analogous manner.

Synthesis of Exemplary Compound 42

N-cyclopropyl-N-(2-methoxy-5-(3-(neopentylamino)benzo[d]isoxazol-5-yl)benzyl)methanesulphonamide Triethylamine (0.14 mL, 0.99 mmol, 1.5 equiv.) was added to a solution of 5-(3-((cyclopropylamino)methyl)-4-methoxyphenyl)-N-neopentylbenzo[d]isoxazol-3-amine (exemplary compound 45) (0.25 g, 0.66 mmol, 1 equiv.) in DCM (10 mL) and the mixture was subsequently cooled to −70° C. Methanesulphonic acid chloride (0.06 mL, 0.79 mmol, 1.2 equiv.) was added in drops and the mixture was heated slowly to RT and stirred for 15 hours. The reaction mixture was diluted with DCM (50 mL) and extracted with sat. aq. sodium hydrogen carbonate sol. (1×10 mL) and sat. aq. NaCl solution (1×10 mL), dried (MgSO$_4$) and the solvent removed in a vacuum. After column-chromatographic purification (EtOAc/DCM; 1:1), the desired product (0.21 g, >99%) is obtained.

Synthesis of Exemplary Compound 49

N-cyclopropyl-N-(3-(3-(neopentylamino)benzo[d]isoxazol-5-yl)benzyl)benzamide

Triethylamine (0.18 mL, 1.29 mmol, 1.5 equiv.) was added to a solution of 5-(3-((cyclopropylamino)methyl)phenyl)-N-neopentylbenzo[d]isoxazol-3-amine (exemplary compound 51) (0.30 g, 0.86 mmol, 1 equiv.) in DCM (10 mL) and the mixture was subsequently cooled to −70° C. Benzoylchloride (0.12 mL, 1.03 mmol, 1.2 equiv.) was added in drops and the mixture was slowly heated to RT and stirred for 15 hours. The reaction mixture was diluted with DCM (80 mL) and extracted with sat. aq. sodium hydrogen carbonate sol. (1×15 mL) and sat. aq. NaCl solution (1×15 mL), dried (MgSO$_4$) and the solvent removed in a vacuum. After column-chromatographic purification (EtOAc/hexane; 10:1), the desired product (0.30 g, 77%) is obtained.

Exemplary compound 43: (N-cyclopropyl-N-(2-methoxy-5-(3-(neopentylamino)benzo[d]isoxazol-5-yl)benzyl)acetamide; 70% yield; Exemplary compound 44 (N-cyclopropyl-N-(2-fluoro-5-(3-(neopentylamino)benzo[d]isoxazol-5-yl)benzyl)acetamide; 50% yield and exemplary compound 50 (N-cyclopropyl-N-(3-(3-(neopentylamino)benzo[d]isoxazol-5-yl)benzyl)acetamide; 64% yield were manufactured in an analogous manner.

Synthesis of Exemplary Compound 40

3-(3-(neopentylamino)benzo[d]isoxazol-5-yl)benzoic acid

A solution of ethyl-3-(3-(neopentylamino)benzo[d]isoxazol-5-yl)benzoate (0.38 g, 1.08 mmol, 1 equiv.) in methanol (4 mL) was cooled to 0° C. and an aqueous solution LiOH*H$_2$O (0.16 g, 2.16 mmol, 2 equiv./in H$_2$O (1.5 mL)) added slowly. The reaction mixture was stirred for 15 h at RT and subsequently concentrated in a vacuum. The residue was absorbed in EtOAc (100 mL), washed with 10% aq. citric acid sol. (2×20 mL), dried (MgSO$_4$) and the solvent removed in a vacuum. The desired product (0.34 g, 97%) is obtained in this manner.

Pharmacological Data:

The benzo[d]isoxazol-3-yl-amine compounds studied according to the invention demonstrate an excellent affinity to the vanilloid receptor 1 (VR1/TRPV1 receptor). Determination is performed according to method I described above.

| Compound | rVR1 [10 μM] stimulation | rVR1 [10 μM] inhibition |
|---|---|---|
| 9 | 0 | 65 |
| 10 | 29 | 99 | whereby
compound 9 is (4-tert-butyl-benzyl)-(6-pyridine-2-yl-benzo[d]isoxazol-3-yl)-amine and
compound 10 is (4-tert-butyl-benzyl)-[6-(3-methyl-pyridine-2-yl)-benzo[d]isoxazol-3-yl]-amine.

The invention claimed is:
1. A substituted benzo[d]isoxazol-3-yl-amine compound corresponding to formula I

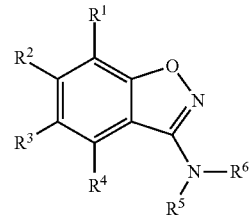

wherein
R$^1$, R$^2$, R$^3$ and R$^4$ each independently denote H, F, Cl, Br, I, —CN, —NC, —NO$_2$; —SF$_5$, —NR$^7$R$^8$, —OR$^9$, —SR$^{10}$, —C(=O)OR$^{11}$, —(C=O)NR$^{12}$R$^{13}$, —S(=O)$_2$R$^{14}$, —C(=O)R$^{15}$, —NR$^{16}$—S(=O)$_2$R$^{17}$; or
a linear or branched, saturated or unsaturated, unsubstituted or mono- or polysubstituted aliphatic group; or
a saturated or unsaturated, unsubstituted or mono- or polysubstituted cycloaliphatic group which optionally may contain one or more heteroatoms as ring members, optionally may be condensed with a monocyclic or polycyclic ring system and/or optionally may be bonded via a linear or branched alkylene, alkenylene or alkinylene group; or
an unsubstituted or substituted aryl or heteroaryl group, which optionally may be condensed with a monocyclic or polycyclic ring system and/or may be bonded via a linear or branched alkylene, alkenylene or alkinylene group;
wherein
at least one of R$^1$, R$^3$ and R$^4$ denotes an unsubstituted or substituted aryl or heteroaryl group, and
the above-mentioned substituted aryl or heteroaryl groups optionally may be substituted with 1, 2, 3, 4 or 5 substituents independently selected from the group consisting of F, Cl, Br, I, —CN, —CF$_3$, —SF$_5$, —OH, —O—C$_{1-5}$-alkyl, —NH$_2$, —NO$_2$, —OCF$_3$, —SCF$_3$, —SH, —SC$_{1-5}$-alkyl, —C$_{1-5}$-alkyl, —C(=O)—OH, —C(=O)—O—C$_{1-5}$-alkyl, —NH—(C$_{1-5}$-alkyl), —N($C_{1-5}$-alkyl)($C_{1-5}$-alkyl), —NH—C(=O)—O—($C_{1-5}$-alkyl), —C(=O)—H, —C(=O)—($C_{1-5}$-alkyl), —C(=O)—N($C_{1-5}$-alkyl)($C_{1-5}$-alkyl), —S(=O)$_2$NH$_2$;
—S(=O)$_2$N(H)($C_{1-5}$-alkyl), —S(=O)$_2$N($C_{1-5}$-alkyl)($C_{1-5}$-alkyl), —S(=O)$_2$phenyl, —S(=O)$_2$—$C_{1-5}$-alkyl, —C(=O)—NH—CH$_3$, —C(=O)—NH—C$_2$H$_5$, —C(=O)—N(cyclopropyl)-$C_{1-5}$-alkyl, —N(cyclopropyl)-S(=O)$_2$—$C_{1-5}$-alkyl, —CH$_2$—NH—S(=O)$_2$—$C_{1-5}$-alkyl, —CH$_2$—N(cyclopropyl)-S(=O)$_2$—$C_{1-5}$-alkyl, —CH$_2$—N(cyclopropyl)-C(=O)—$C_{1-5}$-alkyl, —CH$_2$—N(cyclopropyl)-C(=O)-phenyl, —O-phenyl, —O-benzyl, phenyl, benzyl, thiophenyl (thienyl), furanyl and pyridinyl;

and/or wherein $R^2$ denotes an unsubstituted or substituted aryl or heteroaryl group, and the above-mentioned substituted aryl or heteroaryl groups optionally may be substituted with 1, 2, 3, 4 or 5 substituents independently selected from the group consisting of F, Cl, Br, I, —CN, —CF$_3$, —SF$_5$, —OH, —O—$C_{1-5}$-alkyl, —NH$_2$, —NO$_2$, —OCF$_3$, —SCF$_3$, —SH, —SC$_{1-5}$-alkyl, —$C_{1-5}$-alkyl, —C(=O)—OH, —C(=O)—O—$C_{1-5}$-alkyl, —NH—($C_{1-5}$-alkyl), —N($C_{1-5}$alkyl)($C_{1-5}$-alkyl), —NH—C(=O)—O—($C_{1-5}$-alkyl), —C(=O)—H, —C(=O)—($C_{1-5}$-alkyl), —C(=O)—N($C_{1-5}$alkyl)($C_{1-5}$-alkyl), —S(=O)$_2$NH$_2$;
—S(=O)$_2$N(H)($C_{1-5}$-alkyl), —S(=O)$_2$N($C_{1-5}$-alkyl)($C_{1-5}$-alkyl), —S(=O)$_2$phenyl, —S(=O)$_2$—$C_{1-5}$ alkyl), —C(=O)—NH—CH$_3$, —C(=O)—NH—C$_2$H$_5$, —N(cyclopropyl)-S(=O)$_2$—$C_{1-5}$-alkyl, —CH$_2$—NH—S(=O)$_2$—$C_{1-5}$-alkyl, —CH$_2$—N(cyclopropyl)-S(=O)$_2$—$C_{1-5}$-alkyl, —CH$_2$—N(cyclopropyl)-C(=O)—$C_{1-5}$-alkyl, —CH$_2$—N(cyclopropyl)-C(=O)-phenyl, —O-phenyl, —O-benzyl, phenyl, benzyl, thiophenyl (thienyl), furanyl and pyridinyl;

wherein the cyclic part of any —CH$_2$—N(cyclopropyl)-C(=O)-phenyl, —O-phenyl, —O-benzyl, phenyl, —S(=O)$_2$phenyl, benzyl, thiophenyl (thienyl), furanyl and pyridinyl groups optionally may be substituted with 1, 2, 3, 4 or 5 substituents independently selected from the group consisting of F, Cl, Br, —OH, —CF$_3$, —SF$_5$, —CN, —NO$_2$, —$C_{1-5}$-alkyl, —O—$C_{1-5}$-alkyl, —O—CF$_3$, —S—CF$_3$, phenyl and —O-benzyl;

$R^5$ and $R^6$ each independently denote H, —C(=O)R$^{18}$, —C(=O)NR$^{19}$R$^{20}$, —C(=S)NR$^{21}$R$^{22}$, or —S(=O)$_2$R$^{23}$; or a linear or branched, saturated or unsaturated, unsubstituted or mono- or polysubstituted aliphatic group; or a saturated or unsaturated, unsubstituted or mono- or polysubstituted cycloaliphatic group which optionally contains one or more heteroatoms as ring members, optionally may be condensed with a monocyclic or polycyclic ring system, and/or optionally may be bonded via a linear or branched alkylene group; or an unsubstituted or mono- or polysubstituted aryl or heteroaryl group which optionally may be condensed with a monocyclic or polycyclic ring system and/or optionally may be bonded via a linear or branched alkylene group;

wherein the above-mentioned aryl group optionally may be substituted with 1, 2, 3, 4 or 5 substituents independently selected from the group consisting of F, Cl, Br, I, —CN, —CF$_3$, —SF$_5$, —OH, —O—$C_{1-5}$-alkyl, —O—CF$_3$, —S—CF$_3$, —SH —S—$C_{1-5}$-alkyl, —$C_{1-5}$-alkyl, —C(=O)—OH, —C(=O)—O—$C_{1-5}$-alkyl, —NH—$C_{1-5}$-alkyl, —N($C_{1-5}$-alkyl)$_2$, —NH—C(=O)—O—$C_{1-5}$-alkyl, —C(=O)—H, —C(=O)—$C_{1-5}$-alkyl, —C(=O)—NH$_2$, —C(=O)NH—$C_{1-5}$-alkyl, —C(=O)—N($C_{1-5}$-alkyl)$_2$, —S(=O)$_2$NH$_2$, —S(=O)$_2$N(H)($C_{1-5}$-alkyl), —S(=O)$_2$N($C_{1-5}$-alkyl)($C_{1-5}$-alkyl), —S(=O)$_2$phenyl, —S(=O)$_2$—$C_{1-5}$-alkyl, —CH$_2$—NH-cyclopropyl, —CH$_2$—N($C_{1-5}$-alkyl)—cyclopropyl, —C(=O)—N(cyclopropyl)-$C_{1-5}$-alkyl, —N(cyclopropyl)-S(=O)$_2$—$C_{1-5}$-alkyl, —CH$_2$—NH—S(=O)$_2$—$C_{1-5}$-alkyl, —CH$_2$—N(cyclopropyl)-S(=O)$_2$—$C_{1-5}$-alkyl, —CH$_2$—N(cyclopropyl)-C(=O)—$C_{1-5}$-alkyl, —CH$_2$—N(cyclopropyl)-C(=O)-phenyl, —O-phenyl, —O-benzyl, phenyl, benzyl, thiophenyl (thienyl), furanyl and pyridinyl;

wherein the cyclic part of any —CH$_2$—N(cyclopropyl)-C(=O)-phenyl, —O-phenyl, —O-benzyl, phenyl, —S(=O)$_2$phenyl and benzyl group optionally may be substituted with 1, 2, 3, 4 or 5 substituents independently selected from the group consisting of F, Cl, Br, —OH, —CF$_3$, —SF$_5$, —CN, —NO$_2$, —$C_{1-5}$-alkyl, —O—$C_{1-5}$-alkyl, —OCF$_3$, —SCF$_3$, phenyl and —O-benzyl;

with the proviso that $R^5$ and $R^6$ are not simultaneously hydrogen; or $R^5$ and $R^6$ together with the nitrogen atom to which they are bound form a saturated or unsaturated, unsubstituted or mono- or polysubstituted heterocycloaliphatic ring, which optionally may contain one or more further heteroatoms as ring members;

$R^7$ and $R^8$ each independently denote H, —C(=O)R$^{15}$ or a linear or branched, saturated or unsaturated, unsubstituted or mono- or polysubstituted aliphatic group, or $R^7$ and $R^8$ together with the nitrogen atom to which they are bound form a saturated or unsaturated, unsubstituted or mono- or polysubstituted heterocycloaliphatic group, which optionally may contain one or more further heteroatoms as ring members;

$R^9$, $R^{10}$, $R^{11}$ and $R^{16}$ each independently denote H, or a linear or branched, saturated or unsaturated, unsubstituted or mono- or polysubstituted aliphatic group; or a saturated or unsaturated, unsubstituted or mono- or polysubstituted cycloaliphatic group which optionally may contain one or more heteroatoms as ring members, optionally may be condensed with a monocyclic or polycyclic ring system, and/or optionally can be bonded via a linear or branched alkylene group; or an unsubstituted or mono- or polysubstituted aryl or heteroaryl group which optionally may be condensed with a monocyclic or polycyclic ring system and/or optionally may be bonded via a linear or branched alkylene group;

$R^{12}$ and $R^{13}$ each independently denote H, or a linear or branched, saturated or unsaturated, unsubstituted or mono- or polysubstituted aliphatic group; or $R^{12}$ and $R^{13}$ together with the nitrogen atom to which they are bound form a saturated or unsaturated, unsubstituted or mono- or polysubstituted heterocycloaliphatic ring, which optionally may contain one or more further heteroatoms as ring members;

$R^{14}$ and $R^{23}$ each independently denote —NR$^7$R$^8$; or a linear or branched, saturated or unsaturated, unsubstituted or mono- or polysubstituted aliphatic group;

a saturated or unsaturated, unsubstituted or mono- or polysubstituted cycloaliphatic group which optionally may contain one or more heteroatoms as ring members, optionally is condensed with a monocyclic or polycyclic ring system, and/or optionally may be bonded via a linear or branched alkylene group; or an unsubstituted or mono- or polysubstituted aryl or heteroaryl group which optionally may be condensed with a monocyclic or polycyclic ring system and/or optionally may be bonded via a linear or branched alkylene group;

$R^{15}$, $R^{17}$ and $R^{18}$ each independently denote a linear or branched, saturated or unsaturated, unsubstituted or mono- or polysubstituted aliphatic group; or a saturated or unsaturated, unsubstituted or mono- or polysubstituted cycloaliphatic group which optionally contains one or more heteroatoms as ring members, oprionally may be condensed with a monocyclic or polycyclic ring system and/or optionally may be bonded via a linear or branched alkylene group; or an unsubstituted or mono- or polysubstituted aryl or heteroaryl group which optionally may be condensed with a monocyclic or polycyclic ring system and/or optionally may be bonded via a linear or branched alkylene group;

$R^{19}$ and $R^{20}$ each independently denote H, or a linear or branched, saturated or unsaturated, unsubstituted or mono- or polysubstituted aliphatic group; or $R^{19}$ and $R^{20}$ together with the nitrogen atom to which they are bound form a saturated or unsaturated, unsubstituted or mono- or polysubstituted heterocycloaliphatic ring, which optionally may contain one or more further heteroatoms as ring members;

$R^{21}$ and $R^{22}$ each independently denote H, or a linear or branched, saturated or unsaturated, unsubstituted or mono- or polysubstituted aliphatic group; or $R^{21}$ and $R^{22}$ together with the nitrogen atom to which they are bound form a saturated or unsaturated, unsubstituted or mono- or polysubstituted heterocycloaliphatic ring, which optionally may contain one or more further heteroatoms as ring members;

or a pharmaceutically acceptable salt thereof.

2. A compound according to claim 1, wherein said compound is in the form of an isolated stereoisomer.

3. A compound according to claim 1, wherein said compound is in the form of a mixture of stereoisomers in any mixing ratio.

4. A compound according to claim 3, wherein said compound is in the form of a racemic mixture.

5. A compound according to claim 1, wherein $R^1$, $R^2$, $R^3$ and $R^4$ each independently denote H, F, Cl, Br, I, —CN, —NC, —NO$_2$, —SF$_5$, —NR$^7$R$^8$, —OR$^9$, —SR$^{10}$, —C(=O)OR$^{11}$, —(C=O)NR$^{12}$R$^{13}$, —S(=O)$_2$R$^{14}$, —C(=O)R$^{15}$, —NR$^{16}$—S(=O)$_2$R$^{17}$, C$_{1-10}$-alkyl, C$_{2-10}$-alkenyl, C$_{2-10}$-alkinyl, C$_{3-8}$-cycloalkyl, —C$_{1-5}$-alkylene)-C$_{3-8}$-cycloalkyl, heterocycloalkyl, —(C$_{1-5}$-alkylene)-heterocycloalkyl, aryl, heteroaryl, —(C$_{1-5}$-alkylene)-aryl, or —(C$_{1-5}$-alkylene)-heteroaryl;

wherein at least one of $R^1$, $R^2$, $R^3$ and $R^4$ denotes an aryl or heteroaryl group;

$R^5$ and $R^6$ each independently denote H; —C(=O)R$^{18}$; —C(=O)NR$^{19}$R$^{20}$; —C(=S)NR$^{21}$R$^{22}$; —S(=O)$_2$ R$^{23}$; C$_{1-10}$alkyl, C$_{2-10}$-alkenyl, C$_{2-10}$-alkinyl; C$_{3-8}$-cycloalkyl; —(C$_{1-5}$-alkylene)-C$_{3-8}$-cycloalkyl; heterocycloalkyl; —(C$_{1-5}$-alkylene)-heterocycloalkyl; aryl; heteroaryl; —(C$_{1-5}$-alkylene)-aryl or —(C$_{1-5}$-alkylene)-heteroaryl;

with the proviso that $R^5$ and $R^6$ do not simultaneously denote hydrogen; or $R^5$ and $R^6$ together with the nitrogen atom to which they are bound form a ring selected from the following group H consisting of:

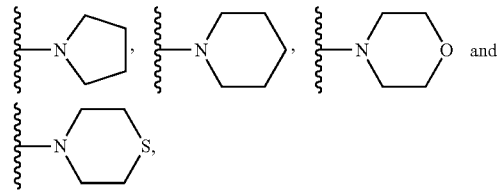

$R^7$ and $R^8$ each independently denote H, —C(=O)R$^{15}$ or C$_{1-10}$-alkyl, or $R^7$ and $R^8$ together with the nitrogen atom to which they are bound form a ring selected from the group H defined above;

$R^9$, $R^{10}$, $R^{11}$ and $R^{16}$ each independently denote H, C$_{1-10}$-alkyl, C$_{2-10}$-alkenyl, C$_{2-10}$-alkinyl, C$_{3-8}$-cycloalkyl, —(C$_{1-5}$-alkylene)-C$_{3-8}$-cycloalkyl, heterocycloalkyl, —(C$_{1-5}$-alkylene)-heterocycloalkyl, aryl, heteroaryl, —(C$_{1-5}$-alkylene)-aryl or —(C$_{1-5}$-alkylene)-heteroaryl;

$R^{12}$ and $R^{13}$ each independently denote H or a C$_{1-10}$-alkyl group, or $R^{12}$ and $R^{13}$ together with the nitrogen atom to which they are bound form a ring selected from the group H defined above;

$R^{14}$ and $R^{23}$ each independently denote —NR$^7$R$^8$; C$_{1-10}$-alkyl, C$_{2-10}$-alkenyl, C$_{2-10}$-alkinyl; C$_{3-8}$-cycloalkyl; —(C$_{1-5}$-alkylene)-C$_{3-8}$-cycloalkyl; heterocycloalkyl; —(C$_{1-5}$-alkylene)-heterocycloalkyl; aryl; heteroaryl; —(C$_{1-5}$-alkylene)-aryl or —(C$_{1-5}$-alkylene)-heteroaryl;

$R^{15}$, $R^{17}$ and $R^{18}$ each independently denote C$_{1-10}$-alkyl, C$_{1-10}$-alkenyl, C$_2$-10-alkinyl, C$_{3-8}$-cycloalkyl, —(C$_{1-5}$-alkylene)-C$_{3-8}$-cycloalkyl, heterocycloalkyl, -(C$_{1-5}$-alkylene)-heterocycloalkyl, aryl, heteroaryl, —(C$_{1-5}$-alkylene)-aryl, or -(C$_{1-5}$-alkylene)-heteroaryl;

$R^{19}$ and $R^{20}$ each independently denote H or C$_{1-10}$-alkyl, or $R^{19}$ and $R^{20}$ together with the nitrogen atom to which they are bound form a ring selected from the group H defined above;

$R^{21}$ and $R^{22}$ each independently denote H or C$_{1-10}$-alkyl, or $R^{21}$ and $R^{22}$ together with the nitrogen atom to which they are bound form a ring selected from the group H defined above;

wherein the above-mentioned C$_{1-10}$-alkyl-, C$_{2-10}$-alkenyl- and C$_{2-10}$-alkinyl groups may be linear or branched and optionally may be substituted with 1, 2, 3, 4 or 5 substituents independently selected from the group consisting of F, Cl, Br, —CN, —OH, —SH, —O—C$_{1-2}$-alkyl, —S—C$_{1-2}$-alkyl and —NH$_2$;

the above-mentioned C$_{3-8}$-cycloalkyl groups optionally may be substituted with 1, 2, 3, 4 or 5 substituents independently selected from the group consisting of F, Cl, Br, —CN, —OH, —SH, —C$_{1-5}$-alkyl, —O—C$_{1-2}$-alkyl, —S—C$_{1-2}$-alkyl and —NH$_2$;

the above-mentioned heterocycloalkyl groups comprise a 4, 5, 6 or 7 membered ring containing 1 or 2 heteroatoms independently selected from the group consisting of oxygen, sulfur and nitrogen, and optionally may be substituted with 1, 2, 3, 4 or 5 substituents independently selected from the group consisting of F, Cl, Br, —CN, —OH, —SH, —C$_{1-5}$-alkyl, —O—C$_{1-2}$-alkyl, —S—C$_{1-2}$-alkyl and —NH$_2$;

the above-mentioned aryl groups for the R groups other than $R^2$ are phenyl or naphthyl groups which optionally may be substituted with 1, 2, 3, 4 or 5 substituents independently selected from the group consisting of F, Cl, Br, I, —$CF_3$, —$OCF_3$, —$SCF_3$, —$SF_5$, —CN, —OH, —SH, —$C_{1-5}$-alkyl, —O—$C_{1-5}$-alkyl, —S—$C_{1-5}$-alkyl, —C(=O)—NH—$CH_3$, —C(=O)—NH—$C_2H_5$, —C(=O)—OH, —C(=O)—$OC_{1-5}$-alkyl, —N(H)($C_{1-5}$-alkyl), —N($C_{1-5}$-alkyl)($C_{1-5}$-alkyl), —C(=O)—H, —C(=O)—$C_{1-5}$-alkyl, —C(=O)N($C_{1-5}$-alkyl)($C_{1-5}$-alkyl), —S(=O)$_2$NH$_2$, —S(=O)$_2$N(H)($C_{1-5}$-alkyl), —S(=O)$_2$N($C_{1-5}$-alkyl)($C_{1-5}$-alkyl), —S(=O)$_2$-phenyl, —S(=O)$_2$—$C_{1-5}$-alkyl, —C(=O)—N(cyclopropyl)-$C_{1-5}$-alkyl, —N(cyclopropyl)-S(=O)$_2$—$C_{1-5}$-alkyl, —CH$_2$—NH—S(=O)$_2$—$C_{1-5}$-alkyl, —CH$_2$—N(cyclopropyl)-S(=O)$_2$—$C_{1-5}$-alkyl, —CH$_2$—N(cyclopropyl)-C(=O)—$C_{1-5}$-alkyl, —CH$_2$—N(cyclopropyl)-C(=O)-phenyl, phenyl, phenoxy, benzyl, thiophenyl (thienyl), furanyl and pyridinyl;

the above-mentioned heteroaryl groups for $R^1$, $R^3$, and $R^4$ are 5 or 6 membered rings containing 1, 2 or 3 heteroatoms independently selected from the group consisting of oxygen, sulfur and nitrogen, and optionally may be substituted with 1, 2, 3, 4 or 5 substituents independently selected from the group consisting of F, Cl, Br, I, —$CF_3$, —$OCF_3$, —$SCF_3$, —$SF_5$, —CN, —OH, —SH, —$C_{1-5}$-alkyl, —O—$C_{1-5}$-alkyl, —S—$C_{1-5}$-alkyl, —C(=O)—OH, —C(=O)—$OC_{1-5}$-alkyl, —NH$_2$, —N(H)($C_{1-5}$-alkyl), —N($C_{1-5}$-alkyl)($C_{1-5}$-alkyl), —C(=O)—NH—$CH_3$, —C(=O)—NH—$C_2H_5$, —C(=O)N($C_{1-5}$-alkyl)($C_{1-5}$-alkyl), —S(=O)$_2$NH$_2$, —S(=O)$_2$N(H)($C_{1-5}$-alkyl), —S(=O)$_2$N($C_{1-5}$-alkyl)($C_{1-5}$-alkyl), —S(=O)$_2$-phenyl, —S(=O)$_2$—$C_{1-5}$-alkyl, —C(=O)—N(cyclopropyl)-$C_{1-5}$-alkyl, —N(cyclopropyl)-S(=O)$_2$—$C_{1-5}$-alkyl, —CH$_2$—NH—S(=O)$_2$—$C_{1-5}$-alkyl, —CH$_2$—N(cyclopropyl)-S(=O)$_2$—$C_{1-5}$-alkyl, —CH$_2$—N(cyclopropyl)-C(=O)—$C_{1-5}$-alkyl, —CH$_2$—N(cyclopropyl)-C(=O)-phenyl, phenyl, phenoxy, benzyl, thiophenyl (thienyl), furanyl and pyridinyl;

the above-mentioned heteroaryl groups for the R groups other than $R^1$, $R^2$, $R^3$, and $R^4$ are 5 or 6 membered rings containing 1, 2 or 3 heteroatoms independently selected from the group consisting of oxygen, sulfur and nitrogen, and optionally may be substituted with 1, 2, 3, 4 or 5 substituents independently selected from the group consisting of F, Cl, Br, I, —$CF_3$, —$OCF_3$, —$SCF_3$, —$SF_5$, —CN, —OH, —SH, —$C_{1-5}$-alkyl, —O—$C_{1-5}$-alkyl, —S—$C_{1-5}$-alkyl, —C(=O)—OH, —C(=O)—$OC_{1-5}$-alkyl, —NH$_2$, —N(H)($C_{1-5}$-alkyl), —N($C_{1-5}$-alkyl)($C_{1-5}$-alkyl), —C(=O)—NH—$CH_3$, —C(=O)—NH—$C_2H_5$, —C(=O)N($C_{1-5}$-alkyl)($C_{1-5}$-alkyl), —S(=O)$_2$NH$_2$, —S(=O)$_2$N(H)($C_{1-5}$-alkyl), —S(=O)$_2$N($C_{1-5}$-alkyl)($C_{1-5}$-alkyl), —S(=O)$_2$—$C_{1-5}$-alkyl, —CH$_2$—NH—cyclopropyl, —CH$_2$—N($C_{1-5}$-alkyl)-cyclopropyl, —C(=O)—N(cyclopropyl)-$C_{1-5}$-alkyl, —N(cyclopropyl)-S(=O)$_2$—$C_{1-5}$-alkyl, —CH$_2$—NH—S(=O)$_2$—$C_{1-5}$-alkyl, —CH$_2$—N(cyclopropyl)-S(=O)$_2$—$C_{1-5}$-alkyl, —CH$_2$—N(cyclopropyl)-C(=O)—$C_{1-5}$alkyl, —CH$_2$—N(cyclopropyl)-C(=O)-phenyl, phenyl, phenoxv, benzyl, thiophenyl (thienyl), furanyl and pyridinyl;

the above-mentioned aryl groups for $R^2$ are phenyl or naphthyl groups which optionally may be substituted with 1, 2, 3, 4 or 5 substituents independently selected from the group consisting of F, Cl, Br, I, —$CF_3$, —$OCF_3$, —$SCF_3$, —$SF_5$, —CN, —OH, —SH, —$C_{1-5}$-alkyl, —O—$C_{1-5}$-alkyl, —S—$C_{1-5}$-alkyl, —C(=O)—NH—$CH_3$, —C(=O)—NH—$C_2H_5$, —C(=O)—OH, —C(=O)—$OC_{1-5}$-alkyl, —N(H)($C_{1-5}$-alkyl), —N($C_{1-5}$-alkyl)($C_{1-5}$-alkyl), —C(=O)—H, —C(=O)—$C_{1-5}$-alkyl, —C(=O)N($C_{1-5}$-alkyl)($C_{1-5}$-alkyl), —S(=O)$_2$NH$_2$, —S(=O)$_2$N(H)($C_{1-5}$-alkyl), —S(=O)$_2$N($C_{1-5}$-alkyl)($C_{1-5}$-alkyl), —S(=O)$_2$-phenyl, —S(=O)$_2$—$C_{1-5}$-alkyl, —N(cyclopropyl)-S(=O)$_2$—$C_{1-5}$-alkyl, —CH$_2$—NH—S(=O)$_2$—$C_{1-5}$-alkyl, —CH$_2$—N(cyclopropyl)-S(=O)$_2$—$C_{1-5}$-alkyl, —CH$_2$—N(cyclopropyl)-C(=O)—$C_{1-5}$-alkyl, —CH$_2$—N(cyclopropyl)-C(=O)-phenyl, phenyl, phenoxy, benzyl, thiophenyl (thienyl), furanyl and pyridinyl; and the above-mentioned heteroaryl groups for $R^2$ are 5 or 6 membered rings containing 1, 2 or 3 heteroatoms independently selected from the group consisting of oxygen, sulfur and nitrogen, and optionally may be substituted with 1, 2, 3, 4 or 5 substituents independently selected from the group consisting of F, Cl, Br, I, —$CF_3$, —$OCF_3$, —$SCF_3$, —$SF_5$, —CN, —OH, —SH, —$C_{1-5}$-alkyl, —O—$C_{1-5}$-alkyl, —S—$C_{1-5}$-alkyl, —C(=O)—OH, —C(=O)—$OC_{1-5}$-alkyl, —NH$_2$, —N(H)($C_{1-5}$-alkyl), —N($C_{1-5}$-alkyl)($C_{1-5}$-alkyl), —C(=O)—NH—$CH_3$, —C(=O)—NH—$C_2H_5$, —C(=O)N($C_{1-5}$-alkyl)($C_{1-5}$-alkyl), —S(=O)$_2$NH$_2$, —S(=O)$_2$N(H)($C_{1-5}$-alkyl), —S(=O)$_2$N($C_{1-5}$-alkyl)($C_{1-5}$-alkyl), —S(=O)$_2$-phenyl, —S(=O)$_2$—$C_{1-5}$-alkyl, —N(cyclopropyl)-S(=O)$_2$—$C_{1-5}$-alkyl, —CH$_2$—NH—S(=O)$_2$—$C_{1-5}$-alkyl, —CH$_2$—N(cyclopropyl)-S(=O)$_2$—$C_{1-5}$-alkyl, —CH$_2$—N(cyclopropyl)-C(=O)—$C_{1-5}$-alkyl, —CH$_2$—N(cyclopropyl)-C(=O)-phenyl, phenyl, phenoxy, benzyl, thiophenyl (thienyl), furanyl and pyridinyl.

6. A compound according to claim 1, wherein $R^1$, $R^2$, $R^3$ and $R^4$ each independently denote H, F, Cl, Br, I, —CN, —$SF_5$, —$NR^7R^8$, —$OR^9$, —$SR^{10}$, —C(=O)$OR^{11}$, —(C=O)$NR^{12}R^{13}$, —S(=O)$_2R^{14}$, —C(=O)$R^{15}$, —$NR^{16}$—S(=O)$_2R^{17}$, $C_{1-4}$-alkyl, $C_{2-4}$-alkenyl, $C_{2-4}$-alkinyl, $C_{3-8}$-cycloalkyl, —($C_{1, 2\ or\ 3}$-alkylene)-$C_{3-8}$-cycloalkyl, heterocycloalkyl, —($C_{1, 2\ or\ 3}$-alkylene)-heterocycloalkyl, aryl, heteroaryl, —($C_{1, 2\ or\ 3}$-alkylene)-aryl or —($C_{1, 2\ or\ 3}$-alkylene)-heteroaryl;

wherein at least one of $R^1$, $R^2$, $R^3$ and $R^4$ denotes an aryl or heteroaryl group;

$R^5$ and $R^6$ each independently denote H, —C(=O)$R^{18}$, —C(=O)$NR^{19}R^{20}$, —C(=S)$NR^{21}R^{22}$, —S(=O)$_2R^{23}$, $C_{1-4}$-alkyl, $C_{2-4}$-alkenyl, $C_{2-4}$-alkinyl, $C_{3-8}$-cycloalkyl, —($C_{1, 2\ or\ 3}$-alkylene)-$C_{3-8}$-cycloalkyl, heterocycloalkyl, —($C_{1, 2\ or\ 3}$-alkylene)-heterocycloalkyl, aryl, heteroaryl, —($C_{1, 2\ or\ 3}$-alkylene)-aryl or —($C_{1, 2\ or\ 3}$-alkylene)-heteroaryl;

with the proviso that $R^5$ and $R^6$ do not simultaneously denote hydrogen; or $R^5$ and $R^6$ together with the nitrogen atom to which they are bound form a ring selected from the group H consisting of:

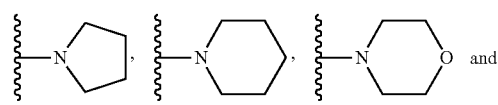

-continued

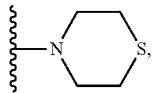

R[7] and R[8] each independently denote H, —C(=O)R[15] or C$_{1-4}$-alkyl, or

R[7] and R[8] together with the nitrogen atom to which they are bound form a ring selected from the group H defined above;

R[9], R[10], R[11] and R[16] each independently denote H; C$_{1-4}$-alkyl, C$_{2-4}$-alkenyl, C$_{2-4}$-alkinyl; C$_{3-8}$-cycloalkyl; —(C$_{1, 2\ or\ 3}$-alkylene)-C$_{3-8}$-cycloalkyl; heterocycloalkyl; —(C$_{1, 2\ or\ 3}$-alkylene)-heterocycloalkyl; aryl; heteroaryl; —(C$_{1, 2\ or\ 3}$-alkylene)-aryl or —(C$_{1, 2\ or\ 3}$-alkylene)-heteroaryl;

R[12] and R[13] each independently denote H or for C$_{1-4}$-alkyl; or

R[12] and R[13] together with the nitrogen atom to which they are bound form a ring selected from the group H defined above;

R[14] and R[23] each independently denote —NR[7]R[8]; C$_{1-4}$-alkyl, C$_{2-4}$-alkenyl, C$_{2-4}$-alkinyl; C$_{3-8}$-cycloalkyl; —(C$_{1, 2\ or\ 3}$-alkylene)-C$_{3-8}$-cycloalkyl; heterocycloalkyl; —(C$_{1, 2\ or\ 3}$-alkylene)-heterocycloalkyl; aryl; heteroaryl; —(C$_{1, 2\ or\ 3}$-alkylene)-aryl or —(C$_{1, 2\ or\ 3}$-alkylene)-heteroaryl;

R[15], R[17] and R[18] each independently denote C$_{1-4}$-alkyl, C$_{2-4}$-alkenyl, C$_{2-4}$-alkinyl; C$_{3-8}$-cycloalkyl; —(C$_{1, 2\ or\ 3}$-alkylene)-C$_{3-8}$-cycloalkyl; heterocycloalkyl; —(C$_{1, 2\ or\ 3}$-alkylene)-heterocycloalkyl; aryl; heteroaryl;

—(C$_{1, 2\ or\ 3}$-alkylene)-aryl or —(C$_{1, 2\ or\ 3}$-alkylene)-heteroaryl;

R[19] and R[20] each independently denote H or for C$_{1-4}$-alkyl, or

R[19] and R[20] together with the nitrogen atom to which they are bound form a ring selected from the group H defined above;

R[21] and R[22] each independently denote H or for C$_{1-4}$-alkyl, or

R[21] and R[22] together with the nitrogen atom to which they are bound form a ring selected from the group H defined above;

wherein the above-mentioned C$_{1-4}$-alkyl-, C$_{2-4}$-alkenyl- and C$_{2-4}$-alkinyl groups may be linear or branched, and optionally may be substituted with 1, 2, 3, 4 or 5 substituents independently selected from the group consisting of F, Cl, Br, —CN, —OH, —OCH$_3$ and —NH$_2$;

the above-mentioned C$_{3-8}$-cycloalkyl groups optionally may be substituted with 1, 2, 3, 4 or 5 substituents independently selected from the group consisting of F, Cl, Br, —CN, —OH, —CH$_3$, —C$_2$H$_5$, —OCH$_3$ and —NH$_2$;

the above-mentioned heterocycloalkyl groups comprise 4, 5, 6 or 7 membered rings containing 1 or 2 heteroatoms independently selected from the group consisting of oxygen, sulfur and nitrogen, and optionally may be substituted with 1, 2, 3, 4 or 5 substituents independently selected from the group consisting of F, Cl, Br, —CN, —OH, —CH$_3$, —C$_2$H$_5$, —OCH$_3$ and —NH$_2$;

the above-mentioned aryl groups for R[1], R[3], and R[4] are phenyl or naphthyl groups which optionally may be substituted with 1, 2, 3, 4 or 5 substituents independently selected from the group consisting of F, Cl, Br, —CF$_3$, —OCF$_3$, —SCF$_3$, —SF$_5$, —CN, —OH, methyl, ethyl, n-propyl, isopropyl, n-butyl, isobutyl, sec-butyl, tert-butyl, methoxy, ethoxy, —N(CH$_3$)$_2$, —N(C$_2$H$_5$)$_2$, phenyl, phenoxy, benzyl, thiophenyl (thienyl), furanyl, pyridinyl, —C(=O)—NH—CH$_3$, —C(=O)—NH—C$_2$H$_5$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—O—CH$_3$, —C(=O)—O—C$_2$H$_5$, —C(=O)—O—C(CH$_3$)$_3$, —C(=O)—O—CH(CH$_3$)$_2$, —C(=O)—OH, —C(=O)—N(cyclopropyl)-CH$_3$, —C(=O)—N(cyclopropyl)-C$_2$H$_5$, —C(=O)—N(cyclopropyl)-CH(CH$_3$)$_2$, —C(=O)—N(cyclopropyl)-C(CH$_3$)$_3$, —CH$_2$—N(cyclopropyl)-S(=O)$_2$—CH$_3$, —CH$_2$—N(cyclopropyl)-S(=O)$_2$—C$_2$H$_5$, —CH$_2$—N(cyclopropyl)-C(=O)—CH$_3$, —CH$_2$—N(cyclopropyl)-C(=O)—C$_2$H$_5$, —CH$_2$—N(cyclopropyl)-C(=O)—CH(CH$_3$)$_2$, —CH$_2$—N(cyclopropyl)-C(=O)—C(CH$_3$)$_3$ and —CH$_2$—N(cyclopropyl)-C(=O)-phenyl;

the above-mentioned aryl groups for the R groups other than R[1], R[2], R[3], and R[4] are phenyl or naphthyl groups which optionally may be substituted with 1, 2, 3, 4 or 5 substituents independently selected from the group consisting of F, Cl, Br, —CF$_3$, —OCF$_3$, —SCF$_3$, —SF$_5$, —CN, —OH, methyl, ethyl, n-propyl, isopropyl, n-butyl, isobutyl, sec-butyl, tert-butyl, methoxy, ethoxy, —N(CH)$_2$, —N(C$_2$H$_5$)$_2$, phenyl, nhenoxv, benzyl, thiophenyl (thienyl), furanyl, pyridinyl, —C(=O)—NH—CH$_3$, —C(=O)—NH—C$_2$H$_5$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—O—CH$_3$, —C(=O)—O—C$_2$H$_5$, —C(=O)—O—C(CH$_3$)$_3$, —C(=O)—O—CH(CH$_3$)$_2$, —C(=O)—OH, —C(=O)—N(cyclopropyl)-CH$_3$, —C(=O)—N(cyclopropyl)-C$_2$H$_5$, —C(=O)—N(cyclopropyl)-CH(CH$_3$)$_2$, —C(=O)—N(cyclopropy1)—C(CH$_3$)$_3$, —CH$_2$—NH-cyclopropyl, —CH$_2$—N(cyclopropyl)-S(=O)$_2$—CH$_3$, —CH$_2$—N(cyclopropyl)-S(=O)$_2$—C$_2$H$_5$, —CH$_2$—N(cyclopropyl)-C(=O)—CH$_3$, —CH$_2$—N(cyclopropyl)-C(=O)—C$_2$H$_5$, —CH$_2$—N(cyclopropyl)-C(=O)—CH(CH$_3$)$_2$, —CH$_2$—N(cyclopropyl)-C(=O)—C(CH$_3$)$_3$ and —CH$_2$—N(cyclopropyl)-C(=O)-phenyl;

the above-mentioned heteroaryl groups for R[1], R[3], and R[4] are furanyl, thienyl (thiophenyl) or pyridinyl groups, and optionally may be substituted with 1, 2, 3, 4 or 5 substituents independently selected from the group consisting of F, Cl, Br, —CF$_3$, —OCF$_3$, —SCF$_3$, —SF$_5$, —CN, —OH, —C(=O)—NH—CH$_3$, —C(=O)—NH—C$_2$H$_5$, methyl, ethyl, n-propyl, isopropyl, n-butyl, isobutyl, sec-butyl, tert-butyl, methoxy, ethoxy, —NH$_2$, —N(CH$_3$)$_2$, —N(C$_2$H$_5$)$_2$, phenyl, phenoxy, benzyl, thiophenyl (thienyl), furanyl, pyridinyl, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—O—CH$_3$, —C(=O)—O—C$_2$H$_5$, —C(=O)—O—C(CH$_3$)$_3$, —C(=O)—O—CH(CH$_3$)$_2$, —C(=O)—OH, —CH$_2$—N(cyclopropyl)-S(=O)$_2$—CH$_3$, —CH$_2$—N(cyclopropyl)-S(=O)$_2$—C$_2$H$_5$, —CH$_2$—N(cyclopropyl)-C(=O)—CH$_3$, —CH$_2$—N(cyclopropyl)-C(=O)—C$_2$H$_5$, —CH$_2$—N(cyclopropyl)-C(=O)—CH(CH$_3$)$_2$, —CH$_2$—N(cyclopropyl)-C(=O)—C(CH$_3$)$_3$ and —CH$_2$—N(cyclopropyl)-C(=O)-phenyl;

the above-mentioned heteroaryl groups for the R groups other than $R^1$, $R^2$, $R^3$, and $R^4$ are furanyl, thienyl (thiophenyl) or pyridinyl groups, and optionally may be substituted with 1, 2, 3, 4 or 5 substituents independently selected from the group consisting of F, Cl, Br, —$CF_3$, —$OCF_3$, —$SCF_3$, —$SF_5$, —CN, —OH, —C(=O)—NH—$CH_3$, —C(=O)—NH—$C_2H_5$ methyl, ethyl, n-propyl, isopropyl, n-butyl, isobutyl, sec-butyl, tert-butyl, methoxy, ethoxy, —$NH_2$, —$N(CH_3)_2$, —$N(C_2H_5)_2$, phenyl, phenoxy, benzyl, thiophenyl (thienyl), furanyl, pyridinyl, —C(=O)—H, —C(=O)—$CH_3$, —C(=O)—$C_2H_5$, —C(=O)—CH($CH_3)_2$, —C(=O)—C($CH_3)_3$, —C(=O)—O—$CH_3$, —C(=O)—O—$C_2H_5$, —C(=O)—O—C($CH_3)_3$, —C(=O)—O—CH($CH_3)_2$, —C(=O)—OH, —$CH_2$—NH-cyclopropyl, —$CH_2$—N(cyclopropyl)-S(=O)$_2$—$CH_3$, —$CH_2$—N(cyclopropyl)-S(=O)$_2$—$C_2H_5$, —$CH_2$—N(cyclopropyl)-C(=O)—$CH_3$, —$CH_2$—N(cyclopropyl)-C(=O)—$C_2H_5$ —$CH_2$—N(cyclopropyl)-C(=O)—CH($CH_3)_2$, —$CH_2$—N(cyclopropyl)-C(=O)—C ($CH_3)_3$ and —$CH_2$—N(cyclopropyl)-C(=O)-phenyl;

the above-mentioned aryl groups for $R^2$ are phenyl or naphthyl groups which optionally may be substituted with 1, 2, 3, 4 or 5 substituents independently selected from the group consisting of F, Cl, Br, —$CF_3$, —$OCF_3$, —$SCF_3$, —$SF_5$, —CN, —OH, methyl, ethyl, n-propyl, isopropyl, n-butyl, isobutyl, sec-butyl, tert-butyl, methoxy, ethoxy, —$N(CH_3)_2$, —$N(C_2H_5)_2$, phenyl, phenoxy, benzyl, thiophenyl (thienyl), furanyl, pyridinyl, —C(=O)—NH—$CH_3$, —C(=O)—NH—$C_2H_5$, —C(=O)—H, —C(=O)—$CH_3$, —C(=O)—$C_2H_5$, —C(=O)—CH($CH_3)_2$, —C(=O)—C($CH_3)_3$, —C(=O)—O—$CH_3$, —C(=O)—O—$C_2H_5$, —C(=O)—O—C($CH_3)_3$, —C(=O)—O—CH($CH_3)_2$, —C(=O)—OH, —$CH_2$—N(cyclopropyl)-S(=O)$_2$—$CH_3$, —$CH_2$—N(cyclopropyl)-S(=O)$_2$—$C_2H_5$, —$CH_2$—N(cyclopropyl)-C(=O)—$CH_3$, —$CH_2$—N(cyclopropyl)-C(=O)—$C_2H_5$, —$CH_2$—N(cyclopropyl)-C(=O)—CH($CH_3)_2$, —$CH_2$—N(cyclopropyl)-C(=O)—C($CH_3)_3$ and —$CH_2$—N(cyclopropyl)-C(=O)-phenyl; and the above-mentioned heteroaryl groups for $R^2$ are furanyl, thienyl (thiophenyl) or pyridinyl groups, and optionally may be substituted with 1, 2, 3, 4 or 5 substituents independently selected from the group consisting of F, Cl, Br, —$CF_3$, -$OCF_3$, —$SCF_3$, —$SF_5$, —CN, —OH, —C(=O)—NH—$CH_3$, —C(=O)—NH—$C_2H_5$, methyl, ethyl, n-propyl, isopropyl, n-butyl, isobutyl, sec-butyl, tert-butyl, methoxy, ethoxy, —$NH_2$, —$N(CH_3)_2$, —$N(C_2H_5)_2$, phenyl, phenoxy, benzyl, thiophenyl (thienyl), furanyl, pyridinyl, —C(=O)—H, —C(=O)—$CH_3$, —C(=O)—$C_2H_5$, —C(=O)—CH($CH_3)_2$, —C(=O)—C($CH_3)_3$, —C(=O)—O—$CH_3$, —C(=O)—O—$C_2H_5$, —C(=O)—O—C($CH_3)_3$, —C(=O)—O—CH($CH_3)_2$, —C(=O)—OH, —$CH_2$—N(cyclopropyl)-S(=O)$_2$—$CH_3$, —$CH_2$—N(cyclopropyl)-S(=O)$_2$—$C_2H_5$, —$CH_2$—N(cyclopropyl)-C(=O)—$CH_3$, —$CH_2$—N(cyclopropyl)-C(=O)—$C_2H_5$, —$CH_2$—N(cyclopropyl)-C(=O)—CH($CH_3)_2$, —$CH_2$—N(cyclopropyl)-C(=O)—C($CH_3)_3$ and —$CH_2$—N(cyclopropyl)-C(=O)-phenyl.

7. A compound according to claim 1, corresponding to formula I'

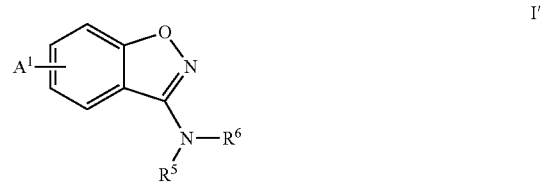

wherein $A^1$ in the $R^1$, $R^3$, or $R^4$ position denotes an aryl or heteroaryl group selected from the group consisting of phenyl, 1-naphthyl, 2-naphthyl, thiophenyl (thienyl), furanyl and pyridinyl, which optionally may be substituted with 1, 2, 3, 4 or 5 substituents independently selected from the group consisting of F, Cl, Br, —$CF_3$, —$OCF_3$, —$SCF_3$, —$SF_5$, —CN, —OH, methyl, ethyl, n-propyl, isopropyl, n-butyl, isobutyl, sec-butyl, tert-butyl, methoxy, ethoxy, —$NH_2$, —$N(CH_3)_2$, —$N(C_2H_5)_2$, phenyl, phenoxy, benzyl, thiophenyl (thienyl), furanyl, pyridinyl, —C(=O)—NH—$CH_3$, —C(=O)—NH—$C_2H_5$, —C(=O)—H, —C(=O)—$CH_3$, —C(=O)—$C_2H_5$, —C(=O)—CH($CH_3)_2$, —C(=O)—C($CH_3)_3$, —C(=O)—O—$CH_3$, —C(=O)—O—$C_2H_5$, —C(=O)—O—C($CH_3)_3$, —C(=O)—O—CH($CH_3)_2$, —C(=O)—OH, —C(=O)—N(cyclopropyl)-$CH_3$, —C(=O)—N(cyclopropyl)-$C_2H_5$, —C(=O)—N(cyclopropyl)-CH($CH_3)_2$, —C(=O)—N(cyclopropyl)-C ($CH_3)_3$, —$CH_2$—N(cyclopropyl)-S(=O)$_2$—$CH_3$, —$CH_2$—N(cyclopropyl)-S(=O)$_2$—$C_2H_5$, —$CH_2$—N(cyclopropyl)-C(=O)—$CH_3$, —$CH_2$—N(cyclopropyl)-C(=O)—$C_2H_5$, —$CH_2$—N(cyclopropyl)-C(=O)—CH($CH_3)_2$, —$CH_2$—N(cyclopropyl)-C(=O)—C($CH_3)_3$ and —$CH_2$—N(cyclopropyl)-C(=O)-phenyl;

$A^1$ in the $R^2$ position denotes an aryl or heteroaryl group selected from the group consisting of phenyl, 1-naphthyl, 2-naphthyl, thiophenyl (thienyl), furanyl and pyridinyl, which optionally may be substituted with 1, 2, 3, 4 or 5 substituents independently selected from the group consisting of F, Cl, Br, —$CF_3$, —$OCF_3$, —$SCF_3$, —$SF_5$, —CN, —OH, methyl, ethyl, n-propyl, isopropyl, n-butyl, isobutyl, sec-butyl, tert-butyl, methoxy, ethoxy, —$NH_2$, —$N(CH_3)_2$, —$N(C_2H_5)_2$, phenyl, phenoxy, benzyl, thiophenyl (thienyl), furanyl, pyridinyl, —C(=O)—NH—$CH_3$, —C(=O)—NH—$C_2H_5$, —C(=O)—H, —C(=O)—$CH_3$, —C(=O)—$C_2H_5$, —C(=O)—CH($CH_3)_2$, —C(=O)—C($CH_3)_3$, —C(=O)—O—$CH_3$, —C(=O)—O—$C_2H_5$, —C(=O)—O—C($CH_3)_3$, —C(=O)—O—CH($CH_3)_2$, —C(=O)—OH, —$CH_2$—N(cyclopropyl)-S(=O)$_2$—$CH_3$, —$CH_2$—N(cyclopropyl)-S(=O)$_2$—$C_2H_5$, —$CH_2$—N(cyclopropyl)-C(=O)—$CH_3$, —$CH_2$—N(cyclopropyl)-C(=O)—$C_2H_5$, —$CH_2$—N(cyclopropyl)-C(=O)—CH($CH_3)_2$, —$CH_2$—N(cyclopropyl)-C(=O)—C($CH_3)_3$ and —$CH_2$—N(cyclopropyl)-C(=O)-phenyl;

$R^5$ and $R^6$ each independently denote H; an alkyl group selected from the group consisting of methyl, ethyl, n-propyl, isopropyl, n-butyl, isobutyl, sec-butyl, tert-butyl, n-pentyl and neopentyl; —C(=O)-phenyl;

—(CH$_2$)-phenyl; —(CH$_2$)$_2$-phenyl; —(CH$_2$)$_3$-phenyl; —(CH$_2$)-pyridinyl; —(CH$_2$)$_2$-pyridinyl; —(CH$_2$)$_3$-pyridinyl;
- wherein the above-mentioned phenyl and pyridinyl groups optionally may be substituted with 1, 2, 3, 4 or 5 substituents independently selected from the group consisting of F, Cl, Br, —CF$_3$, —OCF$_3$, —SCF$_3$, —SF$_5$, —CN, —OH, methyl, ethyl, n-propyl, isopropyl, n-butyl, isobutyl, sec-butyl, tert-butyl, methoxy, ethoxy, —N(CH$_3$)$_2$, —N(C$_2$H$_5$)$_2$, phenyl, phenoxy, benzyl, thiophenyl (thienyl), furanyl and pyridinyl;
  with the proviso that R$^5$ and R$^6$ do not simultaneously denote hydrogen; or
- R$^5$ and R$^6$ together with the nitrogen atom to which they are bound form a ring selected from the group H consisting of:

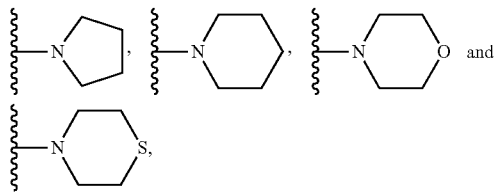

or a pharmaceutically acceptable salt thereof.

8. A compound according to claim 1, corresponding to one of the formulas:

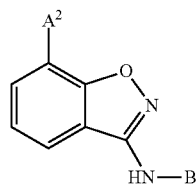

I-A

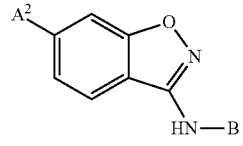

I-B

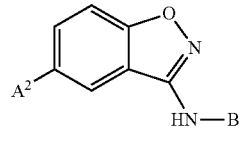

I-C

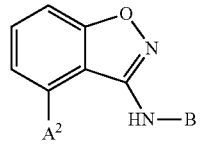

I-D wherein
- A$^2$ in formulas 1-A, 1-C, and 1-D denotes an aryl or heteroaryl group selected from the group consisting of phenyl, 1-naphthyl, 2-naphthyl, thiophenyl (thienyl), furanyl and pyridinyl, which optionally may be substituted with 1, 2, 3, 4 or 5 substituents independently selected from the group consisting of F, Cl, Br, —CF$_3$, —OCF$_3$, —SCF$_3$, —SF$_5$, —CN, —OH, methyl, ethyl, n-propyl, isopropyl, n-butyl, isobutyl, sec-butyl, tert-butyl, methoxy, ethoxy, —NH$_2$, —N(CH$_3$)$_2$, —N(C$_2$H$_5$)$_2$, phenyl, phenoxy, benzyl, thiophenyl (thienyl), furanyl, pyridinyl, —C(=O)—NH—CH$_3$, —C(=O)—NH—C$_2$H$_5$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—O—CH$_3$, —C(=O)—O—C$_2$H$_5$, —C(=O)—O—C(CH$_3$)$_3$, —C(=O)—O—CH(CH$_3$)$_2$, —C(=O)—OH, —C(=O)—N(cyclopropyl)-CH$_3$, —C(=O)—N(cyclopropyl)-C$_2$H$_5$, —C(=O)—N(cyclopropyl)-CH(CH$_3$)$_2$, —C(=O)—N(cyclopropyl)-C(CH$_3$)$_3$, —CH$_2$—N(cyclopropyl)-S(=O)$_2$—CH$_3$, —CH$_2$—N(cyclopropyl)-S(=O)$_2$—C$_2$H$_5$, —CH$_2$—N(cyclopropyl)-C(=O)—CH$_3$, —CH$_2$—N(cyclopropyl)-C(=O)—C$_2$H$_5$, —CH$_2$—N(cyclopropyl)-C(=O)—CH(CH$_3$)$_2$, —CH$_2$—N(cyclopropyl)-C(=O)—C(CH$_3$)$_3$ and —CH$_2$—N(cyclopropyl)-C(=O)-phenyl;
- A$^2$ in formula 1-B denotes an aryl or heteroaryl group selected from the group consisting of phenyl, 1-naphthyl, 2-naphthyl, thiophenyl (thienyl), furanyl and pyridinyl, which optionally may be substituted with 1, 2, 3, 4 or 5 substituents independently selected from the group consisting of F, Cl, Br, —CF$_3$, —OCF$_3$, —SCF$_3$, —SF$_5$, —CN, —OH, methyl, ethyl, n-propyl, isopropyl, n-butyl, isobutyl, sec-butyl, tert-butyl, methoxy, ethoxy, —NH$_2$, —N(CH$_3$)$_2$, —N(C$_2$H$_5$)$_2$, phenyl, phenoxy, benzyl, thiophenyl (thienyl), furanyl, pyridinyl, —C(=O)—NH—CH$_3$, —C(=O)—NH—C$_2$H$_5$, —C(=O)—H, —C(=O)—CH$_3$, —C(=O)—C$_2$H$_5$, —C(=O)—CH(CH$_3$)$_2$, —C(=O)—C(CH$_3$)$_3$, —C(=O)—O—CH$_3$, —C(=O)—O—C$_2$H$_5$, —C(=O)—O—C(CH$_3$)$_3$, —C(=O)—O—CH(CH$_3$)$_2$, —C(=O)—OH, —CH$_2$—N(cyclopropyl)-S(=O)$_2$—CH$_3$, —CH$_2$—N(cyclopropyl)-S(=O)$_2$—C$_2$H$_5$, —CH$_2$—N(cyclopropyl)-C(=O)—CH$_3$, —CH$_2$—N(cyclopropyl)-C(=O)—C$_2$H$_5$, —CH$_2$—N(cyclopropyl)-C(=O)—CH(CH$_3$)$_2$, —CH$_2$—N(cyclopropyl)-C(=O)—C(CH$_3$)$_3$ and —CH$_2$—N(cyclopropyl)-C(=O)-phenyl;
- B denotes an alkyl group selected from the group consisting of methyl, ethyl, n-propyl, isopropyl, n-butyl, isobutyl, sec-butyl, tert-butyl, n-pentyl and neopentyl; —C(=O)-phenyl; —(CH$_2$)-phenyl; —(CH$_2$)$_2$-phenyl; —(CH$_2$)$_3$-phenyl; —(CH$_2$)-pyridinyl; —(CH$_2$)$_2$-pyridinyl and —(CH$_2$)$_3$-pyridinyl;
  wherein the above-mentioned phenyl and pyridinyl groups optionally may be substituted with 1, 2, 3, 4 or 5 substituents independently selected from the group consisting of F, Cl, Br, —CF$_3$, —OCF$_3$, —SCF$_3$, —SF$_5$, —CN, —OH, methyl, ethyl, n-propyl, isopropyl, n-butyl, isobutyl, sec-butyl, tert-butyl, methoxy, ethoxy, —N(CH$_3$)$_2$, —N(C$_2$H$_5$)$_2$, phenyl, phenoxy, benzyl, thiophenyl (thienyl), furanyl and pyridinyl;

or a pharmaceutically acceptable salt thereof.

9. A compound according to claim 8, wherein A$^2$ denotes one of the following groups A$^{21}$ or A$^{22}$:

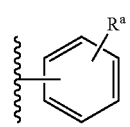

A$^{21}$

-continued

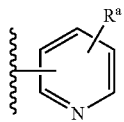
A²² wherein
R^a is selected from the group consisting of H, F, Cl, Br, I, —CN; —CF₃, —OCF₃, —SCF₃, —SF₅, —OH, —SH, methyl, ethyl, n-propyl, isopropyl, n-butyl, isobutyl, sec-butyl, tert-butyl, —OCH₃, —OC₂H₅, —S—CH₃, —S—C₂H₅, —C(=O)—NH—CH₃, —C(=O)—NH—C₂H₅, —C(=O)—H, —C(=O)—O—C₂H₅, —C(=O)—OH, —CH₂—NH-cyclopropyl, —CH₂—N(cyclopropyl)-S(=O)₂—CH₃, —CH₂—N(cyclopropyl)-C(=O)—CH₃ and —CH₂—N(cyclopropyl)-C(=O)-phenyl; and B denotes an alkyl group selected from the group consisting of methyl, ethyl, n-propyl, isopropyl, n-butyl, isobutyl, sec-butyl, tert-butyl, n-pentyl and neopentyl;

or one of the following groups B¹, B² or B³:

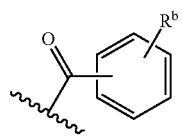
B¹

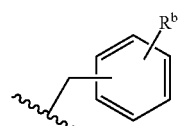
B²

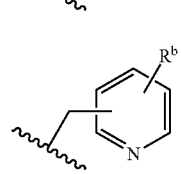
B³ wherein
R^b is selected from the group consisting of H, F, Cl, Br, I, —CN, —CF₃, —OCF₃, —SCF₃, —SF₅, —OH, —SH, methyl, ethyl, n-propyl, isopropyl, n-butyl, isobutyl, sec-butyl, tert-butyl, —OCH₃, —OC₂H₅, —S—CH₃ and —S—C₂H₅.

10. A compound according to claim 1, selected from the group consisting of:

[1] benzyl-[6-(3-chloro-phenyl)-benzo[d]isoxazol-3-yl]-amine,
[2] benzyl-[6-(4-chloro-phenyl)-benzo[d]isoxazol-3-yl]-amine,
[3] benzyl-(6-p-tolyl-benzo[d]isoxazol-3-yl)-amine,
[4] benzyl-[6-(2-methoxy-phenyl)-benzo[d]isoxazol-3-yl]-amine,
[5] N-[6-(3-chloro-phenyl)-benzo[d]isoxazol-3-yl]-benzamide,
[6] N-[6-(4-chloro-phenyl)-benzo[d]isoxazol-3-yl]-benzamide,
[7] N-(6-p-tolyl-benzo[d]isoxazol-3-yl)-benzamide,
[8] N-[6-(2-methoxy-phenyl)-benzo[d]isoxazol-3-yl]-benzamide,
[9] (4-tert-butyl-benzyl)-(6-pyridine-2-yl-benzo[d]isoxazol-3-yl)-amine,
[10] (4-tert-butyl-benzyl)-[6-(3-methyl-pyridine-2-yl)-benzo[d]isoxazol-3-yl]-amine,
[11] (4-tert-butyl-benzyl)-[6-(6-methyl-pyridine-2-yl)-benzo[d]isoxazol-3-yl]-amine,
[12] (4-tert-butyl-benzyl)-(6-phenyl-benzo[d]isoxazol-3-yl)-amine,
[13] [6-(4-chloro-phenyl)-benzo[d]isoxazol-3-yl]-pyridine-2-ylmethyl-amine,
[14] (6-phenyl-benzo[d]isoxazol-3-yl)-pyridine-2-ylmethyl-amine,
[15] pyridine-2-ylmethyl-(6-o-tolyl-benzo[d]isoxazol-3-yl)-amine,
[16] [6-(4-chloro-phenyl)-benzo[d]isoxazol-3-yl]-pyridine-3-ylmethyl-amine,
[17] (6-phenyl-benzo[d]isoxazol-3-yl)-pyridine-3-ylmethyl-amine,
[18] pyridine-3-ylmethyl-(6-o-tolyl-benzo[d]isoxazol-3-yl)-amine,
[19] 2-{3-[(pyridine-3-ylmethyl)-amino]-benzo[d]isoxazol-6-yl}-phenol,
[20] [6-(4-chloro-phenyl)-benzo[d]isoxazol-3-yl]-pyridine-4-ylmethyl-amine,
[21] (6-phenyl-benzo[d]isoxazol-3-yl)-pyridine-4-ylmethyl-amine,
[22] pyridine-4-ylmethyl-(6-o-tolyl-benzo[d]isoxazol-3-yl)-amine,
[23] 4-{[6-(4-chloro-phenyl)-benzo[d]isoxazol-3-ylamino]-methyl}-benzonitrile,
[24] 4-[(6-phenyl-benzo[d]isoxazol-3-ylamino)-methyl]-benzonitrile,
[25] 4-[(6-o-tolyl-benzo[d]isoxazol-3-ylamino)-methyl]-benzonitrile,
[26] 4-{[6-(2-hydroxy-phenyl)-benzo[d]isoxazol-3-ylamino]-methyl}-benzonitrile,
[27] [6-(4-chloro-phenyl)-benzo[d]isoxazol-3-yl]-(3-methyl-benzyl)-amine,
[28] (3-methyl-benzyl)-(6-phenyl-benzo[d]isoxazol-3-yl)-amine,
[29] (3-methyl-benzyl)-(6-o-tolyl-benzo[d]isoxazol-3-yl)-amine,
[30] 2-[3-(3-methyl-benzylamino)-benzo[d]isoxazol-6-yl]-phenol,
[31] (3-chloro-benzyl)-[6-(4-chloro-phenyl)-benzo[d]isoxazol-3-yl]-amine,
[32] (3-chloro-benzyl)-(6-phenyl-benzo[d]isoxazol-3-yl)-amine,
[33] (3-chloro-benzyl)-(6-o-tolyl-benzo[d]isoxazol-3-yl)-amine,
[34] 2-[3-(3-chloro-benzylamino)-benzo[d]isoxazol-6-yl]-phenol,
[35] 2-(3-(neopentylamino)benzo[d]isoxazol-5-yl)benzoic acid,
[36] ethyl 4-(3-(neopentylamino)benzo[d]isoxazol-5-yl)benzoate,
[37] N-neopentyl-5-(3-(trifluoromethyl)phenyl)benzo[d]isoxazol-3-amine,
[38] 3-(3-(neopentylamino)benzo[d]isoxazol-5-yl)benzonitrile,
[39] N-methyl-3-(3-(neopentylamino)benzo[d]isoxazol-5-yl)benzamide,
[40] 3-(3-(neopentylamino)benzo[d]isoxazol-5-yl)benzoic acid,
[41] ethyl 3-(3-(neopentylamino)benzo[d]isoxazol-5-yl)benzoate,

[42] N-cyclopropyl-N-(2-methoxy-5-(3-(neopentylamino)benzo[d]isoxazol-5-yl)-benzyl)methanesulfonamide,
[43] N-cyclopropyl-N-(2-methoxy-5-(3-(neopentylamino)benzo[d]isoxazol-5-yl)-benzyl)acetamide,
[44] N-cyclopropyl-N-(2-fluoro-5-(3-(neopentylamino)benzo[d]isoxazol-5-yl)-benzyl)acetamide,
[45] 5-(3-((cyclopropylamino)methyl)-4-methoxyphenyl)-N-neopentylbenzo[d]-isoxazol-3-amine,
[46] 5-(3-((cyclopropylamino)methyl)-4-fluorophenyl)-N-neopentylbenzo[d]-isoxazol-3-amine,
[47] 2-methoxy-5-(3-(neopentylamino)benzo[d]isoxazol-5-yl)benzaldehyde,
[48] 2-fluoro-5-(3-(neopentylamino)benzo[d]isoxazol-5-yl)benzaldehyde,
[49] N-cyclopropyl-N-(3-(3-(neopentylamino)benzo[d]isoxazol-5-yl)benzyl)-benzamide,
[50] N-cyclopropyl-N-(3-(3-(neopentylamino)benzo[d]isoxazol-5-yl)benzyl)-acetamide,
[51] 5-(3-((cyclopropylamino)methyl)phenyl)-N-neopentylbenzo[d]isoxazol-3-amine and
[52] 3-(3-(neopentylamino)benzo[d]isoxazol-5-yl)benzaldehyde;
and pharmaceutically acceptable salts or solvates thereof.

11. A compound according to claim 1, wherein said compound at a concentration of 10 μM in the FLIPR assay exhibits an inhibition of the $Ca^{2+}$ ion inflow in dorsal root ganglia of rats of at least 10% in comparison to the maximum achievable inhibition of the $Ca^{2+}$ ion inflow with capsaicin at a concentration of 10 μM.

12. A compound according to claim 11, wherein said compound at a concentration of 10 μM in the FLIPR assay exhibits an inhibition of the $Ca^{2+}$ ion inflow in dorsal root ganglia of rats of at least 70%.

13. A compound according to claim 12, wherein said compound at a concentration of 10 μM in the FLIPR assay exhibits an inhibition of the $Ca^{2+}$ ion inflow in dorsal root ganglia of rats of at least 90%.

14. A process for producing a compound according to claim 1, said process comprising:
reacting an optionally substituted 2-fluoro-benzonitrile compound of formula II

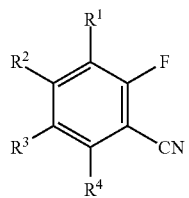

wherein $R^1$, $R^2$, $R^3$ and $R^4$ have the meaning given in claim 1,
in a reaction medium in the presence of a base
with an acetohydroxamic acid of formula III

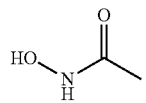

to obtain an initial product compound corresponding to formula I

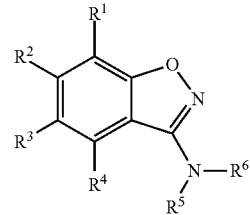

wherein $R^1$ through $R^4$ have the meaning defined above, and
$R^5$ and $R^6$ each denote hydrogen,
and
subsequently reacting the initial product compound in a reaction medium in the presence of a base with an isocyanate of formula

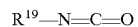

wherein $R^{19}$ has the meaning given in claim 1, to obtain a secondary product compound corresponding to formula I wherein
$R^1$, $R^2$, $R^3$, $R^4$ and $R^5$ have the meanings defined above, and
$R^6$ denotes —C(=O)—$NR^{19}R^{20}$, wherein
$R^{19}$ has the meaning defined above, and
$R^{20}$ denotes hydrogen,
or
subsequently reacting the initial product compound in a reaction medium in the presence of a base with an isothiocyanate of formula

wherein $R^{21}$ has the meaning given in claim 1,
to obtain an alternate secondary product compound corresponding to formula I
wherein $R^1$, $R^2$, $R^3$, $R^4$ and $R^5$ have the meanings defined above, and
$R^6$ denotes —C(=S)—$NR^{21}R^{22}$, wherein
$R^{21}$ has the meaning defined above, and
$R^{22}$ denotes hydrogen,
and
optionally reacting a compound of formula I, wherein
$R^2$, $R^3$, $R^4$ and $R^5$ have the meanings defined above, and
$R^6$ denotes —C(=O)—$NR^{19}R^{20}$ or —C(=S)—$NR^{21}R^{22}$, wherein
$R^{19}$ and $R^{21}$ have the meanings defined above, and
$R^{20}$ and $R^{22}$ each denote hydrogen,
in a reaction medium in the presence of a base,
with at least one compound of formula

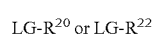

wherein LG denotes a leaving group, and
$R^{20}$ and $R^{22}$ have the meanings given in claim 1 with the exception of hydrogen,
to obtain a compound of formula I, wherein
$R^1$ through $R^6$ have the meanings defined above,
or
optionally reacting a compound of formula I, wherein
$R^1$, $R^2$, $R^3$, $R^4$ have the meaning defined above, and $R^5$ and $R^6$ each denote H,
in a reaction medium, in the presence of a base,
with at least one compound of formula $$LG\text{-}R^5 \text{ or } LG\text{-}R^6$$

wherein LG denotes a leaving group, and
$R^5$ and $R^6$ have the meanings given in claim 1 with the exception of hydrogen,
to obtain a compound of formula I, wherein $R^1$ through $R^6$ have the meanings defined above,
or
reacting a of formula I, wherein
$R^1$ through $R^4$ have the meaning defined above, and
$R^5$ and $R^6$ each denote H,
in a reaction medium, in the presence of an acid and a reducing agent,
with a compound of formula $$R^5\text{—}(C{=}O)\text{—}H$$

wherein $R^5$ has the meaning given in claim 1 with the exception of H, —C(=O)$R^{18}$, —C(=O)—N$R^{19}R^{20}$, —C(=S)—N$R^{21}R^{22}$ and —S(=O)$_2R^{23}$,
to obtain a compound of formula I, wherein
$R^1$ to $R^5$ have the meanings defined above, and
$R^6$ denotes H;
or
reacting a compound of formula I, wherein
$R^1$ through $R^4$ have the meaning defined above, and
$R^5$ and $R^6$ each denote H,
in a reaction medium,
with a compound of formula $$R^{18}\text{—}C({=}O)\text{-}LG$$

wherein $R^{18}$ has the meaning given in claim 1, and
LG denotes a leaving group,
to obtain a compound of formula I, wherein
$R^1$ through $R^4$ have the meaning defined above,
$R^5$ denotes a —C(=O)$R^{18}$ group, and
$R^6$ denotes hydrogen;
or
reacting a compound of formula I, wherein
$R^1$ through $R^4$ have the meanings defined above, and
$R^5$ and $R^6$ each denote H,
in a reaction medium in the presence of a coupling reagent, and optionally in the presence of a base,
with a compound of formula $$R^{18}\text{—}C({=}O)\text{—}OH$$

wherein $R^{18}$ has the meaning given in claim 1,
to obtain a compound of formula I wherein
$R^1$ through $R^4$ have the meaning defined above,
$R^5$ denotes a —C(=O)$R^{18}$ group, and
$R^6$ denotes hydrogen;
or
reacting a compound of formula I, wherein $R^1$ through $R^4$ have the meaning defined above, and
$R^5$ and $R^6$ each denote H,
in a reaction medium, optionally in the presence of a base,
with a compound of formula $$R^{23}\text{—}S({=}O)_2\text{-}LG$$

wherein $R^{23}$ has the meaning given in claim 1, and
LG denotes a leaving group,
to obtain a compound of formula I, wherein
$R^1$ through $R^4$ have the meaning defined above,
$R^5$ denotes a —S(=O)$_2$—$R^{23}$ group, and
$R^6$ is hydrogen;
and optionally isolating or purifying any of the obtained compounds.

15. A process according to claim 14, wherein:

the reaction of the initial product compound with the isocyanate is carried out in the presence of a base selected from the group consisiting of triethylamine, 4,4-dimethylaminopyridine and diisopropylethylamine;

the secondary product or alternate secondary product compound is reacted in the presence of a base which is a metal hydride or a metal alcoholate salt selected from the group consisting of sodium hydride, potassium hydride, potassium t-butoxide, sodium t-butoxide, potassium methoxide, sodium methoxide, sodium methoxide and potassium methoxide;

LG denotes a halogen leaving group;

the compound of formula I wherein is reacted in the presence of a base which is a metal hydride or metal alcoholate salt selected from the group consisting of sodium hydride, potassium hydride, potassium t-butoxide, sodium t-butoxide, potassium methoxide, sodium methoxide, sodium methoxide and potassium methoxide; and the acid is trifluoroacetic acid, and the reducing agent is triethylsilane.

16. A process for producing a compound according to claim 1, comprising:

reacting an optionally substituted 2-fluoro-benzonitrile compound of formula II,

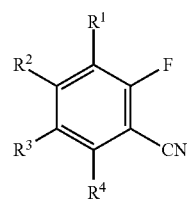

II wherein at least one of groups $R^1$, $R^2$, $R^3$ and $R^4$ denotes a leaving group, and the remaining groups have the meanings given in claim 1 with the exception of an optionally substituted aryl or heteroaryl group, reaction medium in the presence of a base, an acetohydroxamic acid of formula III

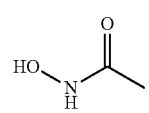

III to obtain an initial product compound of formula I,

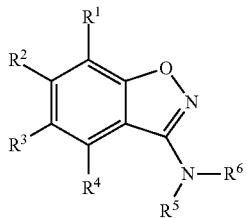

wherein $R^1$ through $R^4$ have the meaning defined above, and
$R^5$ and $R^6$ each denote hydrogen,
and
subsequently reacting the obtained initial product compound in a reaction medium an optionally in the presence of a base,
with an isocyanate of formula

$R^{19}$—N=C=O wherein $R^{19}$ has the meaning given in claim 15,
to obtain a compound of formula I, wherein
$R^1, R^2, R^3, R^4$ and $R^5$ have the meanings defined above, and
$R^6$ denotes —C(=O)—NR$^{19}$R$^{20}$, wherein
$R^{19}$ has the meaning defined above, and
$R^{20}$ denotes hydrogen,
or
subsequently reacting the initial product compound,
in a reaction medium, and optionally in the presence of a base,
with an isothiocyanate of formula

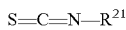
S=C=N—$R^{21}$ wherein $R^{21}$ has the meaning given in claim 15,
to obtain a compound of formula I, wherein
$R^1, R^2, R^3, R^4$ and $R^5$ have the meanings defined above, and
$R^6$ denotes —C(=S)—NR$^{21}$R$^{22}$, wherein
$R^{21}$ has the meaning defined above, and
$R^{22}$ denotes hydrogen;
and
optionally reacting a compound of formula I wherein $R^1$, $R^2$, $R^3$, $R^4$ and $R^5$ have the meaning defined above and $R^6$ denotes —C(=O)—NR$^{19}$R$^{20}$ or —C(=S)—NR$^{21}$$^{R22}$;
wherein $R^{19}$ and $R^{21}$ have the meanings defined above, and $R^{2o}$ and $R^{22}$ each denote hydrogen,
in a reaction medium, in the presence of at least one base,
with a compound of formula LG-$R^{20}$ or LG-$R^{22}$ wherein LG denotes a leaving group, and
$R^{20}$ and $R^{22}$ have the meanings given in claim 15 with the exception of hydrogen, to obtain a compound of formula I, wherein $R^1$ through $R^6$ have the meanings defined above;
or
optionally reacting a compound of formula I, wherein $R^1, R^2, R^3$ and $R^4$ have the meaning defined above, and $R^5$ and $R^6$ each denote H,
in a reaction medium, in the presence of a base,
with a compound of formula LG-$R^5$ or LG-$R^6$ wherein LG denotes a leaving group, and $R^5$ and $R^6$ have the meanings given in claim 1 with the exception of hydrogen,
to obtain a compound of formula I, wherein $R^1$ through $R^6$ have the meanings defined above;
or
reacting a compound of formula I, wherein
$R^1$ through $R^4$ have the meaning defined above, and
$R^5$ and $R^6$ each denote H,
in a reaction medium, in the presence of an acid and a reducing agent,
with a compound of formula

$R^5$—(C=O)—H wherein $R^5$ has the meaning given in claim 1 with the exception of H, —C(=O)R$^{18}$, —C(=O)—NR$^{19}$R$^{20}$, —C(=S)—NR$^{21}$R$^{22}$ and —S(=O)$_2$R$^{23}$,
to obtain a compound of formula I, wherein
$R^1$ through $R^5$ have the meanings defined above, and
$R^6$ denotes H;
or
reacting a compound of formula I, wherein
$R^1$ through $R^4$ have the meaning defined above, and
$R^5$ and $R^6$ each denote H,
in a reaction medium
with a compound of formula

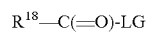
$R^{18}$—C(=O)-LG wherein $R^{18}$ has the meaning given in claim 15, and LG denotes a leaving group,
to obtain a comound of formula I, wherein
$R^1$ through $R^4$ have the meaning defined above,
$R^5$ denotes a —C(=O)R$^{18}$ group, and
$R^6$ denotes hydrogen;
or
reacting a compound of formula I, wherein
$R^1$ through $R^4$ have the meaning defined above, and
$R^5$ and $R^6$ each denote H,
in a reaction medium in the presence of a coupling reagent, and optionally in the presence of a base,
with a compound of formula

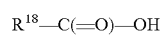
$R^{18}$—C(=O)—OH wherein $R^{18}$ has the meaning given in claim 1,
to obtain a compound of formula I, wherein
$R^1$ through $R^4$ have the meaning defined above,
$R^5$ denotes a —C(=O)R$^{18}$ group, and
$R^6$ denotes hydrogen;
or
reacting a compound of formula I, wherein
$R^1$ through $R^4$ have the meaning defined above, and
$R^5$ and $R^6$ each denote H,
in a reaction medium, and optionally in the presence of a base,
with a compound of formula

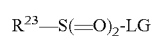
$R^{23}$—S(=O)$_2$-LG wherein $R^{23}$ has the meaning given in claim 15, and LG denotes a leaving group,
to obtain a compound of formula I, wherein
$R^1$ through $R^4$ have the meaning defined above,
$R^5$ denotes a —S(=O)$_2$—R$^{23}$ group, and
$R^6$ denotes hydrogen;
and
reacting a compound of formula I, in which at least one of groups $R^1$ to $R^4$ denotes a leaving group, and the remaining groups have the meaning defined above, optionally in a reaction medium, and optionally in the presence of a base and a catalyst which optionally may be polymer-bonded, and optionally in the presence of a ligand which optionally may be polymer-bonded, and optionally under microwave irradiation,
with a boronic acid compound of the formula,

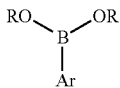

wherein Ar denotes an unsubstituted or mono- or polysubstituted aryl or heteroaryl group as defined in claim 15, and each R denotes hydrogen or an organic group, or the two groups R together with the —O—B—O-group to which they are bound form a heterocycloalkyl ring, to obtain a compound of formula I, in which at least one of groups $R^1$ to $R^4$ denotes an unsubstituted or mono- or polysubstituted aryl or heteroaryl group; and reacting a compound of formula I, in which at least one of groups $R^1$ to $R^4$ denotes a leaving group, and the remaining groups have the meaning defined above, with an organometal compound of formula R'-M-X, wherein
R' denotes an unsubstituted or mono- or polysubstituted aryl or heteroaryl group as defined in claim 1,
M denotes a transition metal ion, and
X denotes a leaving group, optionally in a reaction medium, and optionally in the presence of a catalyst which optionally may be polymer-bonded, to obtain a compound of formula I in which at least one of groups $R^1$ to $R^4$ denotes an unsubstituted or mono- or polysubstituted aryl or heteroaryl group;
and optionally isolating or purifying any of the obtained compounds.

17. A process according to claim 16, wherein
the leaving group is a halogen selected from the group consisting of chlorine, bromine and iodine, or a sulfonic acid ester selcted from the group consisting of triflate, mesylate and tosylate groups;
the initial product compound is reacted in the presence of a base selected from the group consisting of triethylamine, 4,4-dimethylaminopyridine and diisopropylethylamine;

the compound of formula I in which $R^6$ is —C(=O)—$NR^{19}R^{20}$ or —C(=S)—$NR^{21}R^{22}$ is reacted in the presence of a base which is a metal hydride or metal alcoholate salt selected from the group consisting of sodium hydride, potassium hydride, potassium t-butoxide, sodium t-butoxide, potassium methoxide, sodium methoxide, sodium methoxide and potassium methoxide;
the acid is trifluoroacetic acid, and the reducing agent is triethylsilane;
the compound of formula I in which at least one of groups $R^1$ to $R^4$ denotes a leaving group is reacted in the presence of a base selected from the group consisting of potassium carbonate, sodium carbonate, potassium phosphate, sodium hydrogen phosphate, cesium carbonate, triethylamine, [1,4]-diazabicyclo-[2.2.2]-octane, diisopropylamine, diisopropylethylamine and N-methylmorpholine; and in the presence of a catalyst selected from the group consisting of
palladium(II)acetate,
tris(dibenzylidenacetone)dipalladium,
palladium(0)bis(dibenzylidenacetone),
tetrakis(triphenylphosphine)palladium(0),
(1,1'-bis(diphenylphosphino)-ferrocene)dichloropalladium(II),
bis(acetonitrile)dichloropalladium(II),
palladium(II)chloride,
dichlorobis(triphenyl-phosphine)palladium(II),
dichloro(tricyclohexylphosphine)palladium(II),
bis(acetato)bis(triphenylphosphine)-palladium(II),
bistriphenylphosphinepalladium(II)dichloride, and
bistriphenyl-phosphinepalladium(II)acetate, and
iron(III)chloride;
said ligand is selected from the group consisting of 2-dicyclohexylphosphino-2',6'-dimethoxybiphenyl (S-Phos), 2-dicyclohexylphosphino-2',4',6'-triisopropylbiphenyl (X-Phos), tricyclohexylphosphine, tricyclohexylphosphine tetrafluoroborate, tri-tert-butylphosphine tetrafluoroborate, and triphenylphosphine and imidazolium salts;
R denotes hydrogen or an alkyl group; and
M denotes a magnesium or zinc ion.

18. A pharmaceutical composition comprising a compound according to claim 1, and at least one pharmaceutically acceptable excipient.

* * * * *